US008895741B2

(12) United States Patent
Wu et al.

(10) Patent No.: US 8,895,741 B2
(45) Date of Patent: *Nov. 25, 2014

(54) PROCESS FOR THE SYNTHESIS OF BIARYL OXAZOLIDINONES

(75) Inventors: Yusheng Wu, New Haven, CT (US); Shili Chen, Cheshire, CT (US); Yi Chen, Chestnut Hill, MA (US); Roger Hanselmann, Branford, CT (US); Rongliang Lou, Cheshire, CT (US); Jiacheng Zhou, Newark, DE (US)

(73) Assignee: Melinta Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,091

(22) Filed: Sep. 14, 2012

(65) Prior Publication Data

US 2013/0066076 A1 Mar. 14, 2013

Related U.S. Application Data

(63) Continuation of application No. 10/566,150, filed as application No. PCT/US2004/024339 on Jul. 28, 2004, now Pat. No. 8,324,398, which is a continuation-in-part of application No. 10/859,476, filed on Jun. 2, 2004, now Pat. No. 6,969,726.

(60) Provisional application No. 60/530,371, filed on Dec. 17, 2003, provisional application No. 60/576,163, filed on Jun. 2, 2004, provisional application No. 60/490,855, filed on Jul. 29, 2003, provisional application No. 60/529,731, filed on Dec. 15, 2003, provisional application No. 60/531,584, filed on Dec. 19, 2003.

(51) Int. Cl.
| | |
|---|---|
| C07D 263/20 | (2006.01) |
| C07D 263/32 | (2006.01) |
| C07D 413/06 | (2006.01) |
| C07D 417/14 | (2006.01) |
| C07D 453/02 | (2006.01) |
| C07D 413/12 | (2006.01) |
| C07D 417/10 | (2006.01) |
| C07D 487/04 | (2006.01) |
| C07D 417/12 | (2006.01) |
| C07D 473/00 | (2006.01) |
| C07D 413/10 | (2006.01) |
| C07D 413/14 | (2006.01) |

(52) U.S. Cl.
CPC ............ *C07D 263/20* (2013.01); *C07D 417/14* (2013.01); *C07D 413/12* (2013.01); *C07D 417/10* (2013.01); *C07D 413/06* (2013.01); *C07D 487/04* (2013.01); *C07D 263/32* (2013.01); *C07D 417/12* (2013.01); *C07D 473/00* (2013.01); *C07D 413/10* (2013.01); *C07D 413/14* (2013.01); *C07D 453/02* (2013.01)

USPC ........ 544/369; 546/209; 546/271.4; 548/127; 548/131; 548/194; 548/232

(58) Field of Classification Search
None
See application file for complete search history.

(56) References Cited

U.S. PATENT DOCUMENTS

| | | | |
|---|---|---|---|
| 4,348,393 A | 9/1982 | Bourgery et al. |
| 4,948,801 A | 8/1990 | Carlson et al. |
| 5,043,443 A | 8/1991 | Carlson et al. |
| 5,130,316 A | 7/1992 | Carlson et al. |
| 5,254,577 A | 10/1993 | Carlson et al. |
| 5,523,403 A | 6/1996 | Barbachyn |
| 5,565,571 A | 10/1996 | Barbachyn et al. |
| 5,627,181 A | 5/1997 | Riedl et al. |
| 5,654,428 A | 8/1997 | Barbachyn et al. |
| 5,654,435 A | 8/1997 | Barbachyn et al. |
| 5,684,023 A | 11/1997 | Riedl et al. |
| 5,756,732 A | 5/1998 | Barbachyn et al. |
| 5,801,246 A | 9/1998 | Barbachyn et al. |
| 5,843,967 A | 12/1998 | Riedl et al. |
| 5,922,708 A | 7/1999 | Riedl et al. |
| 5,929,248 A | 7/1999 | Barbachyn et al. |
| 5,981,528 A | 11/1999 | Gravestock |
| 6,239,152 B1 | 5/2001 | Gordeev et al. |
| 6,271,383 B1 | 8/2001 | Gravestock |
| 6,365,751 B1 | 4/2002 | Gravestock |
| 6,441,005 B1 | 8/2002 | Gordeev et al. |
| 6,495,551 B1 | 12/2002 | Betts et al. |
| 6,531,470 B1 | 3/2003 | Gordeev et al. |
| 6,562,844 B2 | 5/2003 | Gordeev et al. |
| 6,605,630 B1 | 8/2003 | Gravestock |
| 6,617,339 B1 | 9/2003 | Gravestock |
| 6,638,955 B2 | 10/2003 | Gravestock |
| 6,689,779 B2 | 2/2004 | Lee et al. |
| 6,821,980 B1 | 11/2004 | Guerry et al. |

(Continued)

FOREIGN PATENT DOCUMENTS

| | | |
|---|---|---|
| DE | 10034627 A1 | 1/2002 |
| EP | 0352781 A2 | 1/1990 |

(Continued)

OTHER PUBLICATIONS

Barbachyn et al. "Oxazolidinone Structure-Activity Relationships Leading to Linezolid." *Angew Chem. Int. Ed. Engl.* 42.18(2003):2010-2023.

Brickner. "Oxazolidone Antibacterial Agents." *Curr. Pharm. Des.* 2.2(1996):175-194.

Gleave et al. "Synthesis and Antibacterial Activity of [6,6,5] and [6,6,5] Tricylcic Fused Oxazolidinones." *Bioorg. Med. Chem. Lett.* 8(1998):1231-1236.

Gregory et al. "Antibacterials. Synthesis and Structure-Activity Studies of 3-Aryl-2-Oxazolidinones. 1. The 'B' Group." *J. Med. Chem.* 32.8(1989):1673-1681.

(Continued)

*Primary Examiner* — Kamal Saeed
(74) *Attorney, Agent, or Firm* — Cooley LLP

(57) ABSTRACT

The present invention relates to processes for the preparation of biaryl oxazolidinones. These compounds are useful as anti-infective, anti-proliferative, anti-inflammatory, and pro-kinetic agents.

20 Claims, No Drawings

(56) References Cited

U.S. PATENT DOCUMENTS

| | | |
|---|---|---|
| 2002/0169191 A1 | 11/2002 | Gordeev et al. |
| 2002/0183371 A1 | 12/2002 | Gordeev et al. |
| 2003/0144263 A1 | 7/2003 | Gravestock |
| 2003/0166620 A1 | 9/2003 | Lee et al. |
| 2004/0132764 A1 | 7/2004 | Locher |
| 2005/0038092 A1 | 2/2005 | Fukuda |
| 2005/0043317 A1 | 2/2005 | Zhou et al. |
| 2006/0270637 A1 | 11/2006 | Gravestock et al. |
| 2007/0197541 A1 | 8/2007 | Oyelere et al. |

FOREIGN PATENT DOCUMENTS

| | | |
|---|---|---|
| EP | 0694543 A1 | 1/1996 |
| EP | 1286998 A1 | 3/2003 |
| JP | 8151577 A | 6/1996 |
| JP | 8151578 A | 6/1996 |
| JP | 4777246 B2 | 9/2011 |
| WO | WO-9309103 A1 | 5/1993 |
| WO | WO-9413649 A1 | 6/1994 |
| WO | WO-9730995 A1 | 8/1997 |
| WO | WO-9854161 A1 | 12/1998 |
| WO | WO-9910342 A1 | 3/1999 |
| WO | WO-9928317 A1 | 6/1999 |
| WO | WO-9933839 A1 | 7/1999 |
| WO | WO-9937630 A1 | 7/1999 |
| WO | WO-9964416 A2 | 12/1999 |
| WO | WO-9964417 A2 | 12/1999 |
| WO | WO-0010566 A1 | 3/2000 |
| WO | WO-0021960 A1 | 4/2000 |
| WO | WO-0029396 A1 | 5/2000 |
| WO | WO-0109107 A1 | 2/2001 |
| WO | WO-0132633 A1 | 5/2001 |
| WO | WO-0140236 A2 | 6/2001 |
| WO | WO-0142229 A1 | 6/2001 |
| WO | WO-0181350 A1 | 11/2001 |
| WO | WO-0194342 A1 | 12/2001 |
| WO | WO-02053560 A1 | 7/2002 |
| WO | WO-02080841 A2 | 10/2002 |
| WO | WO-02081468 A1 | 10/2002 |
| WO | WO-02081469 A1 | 10/2002 |
| WO | WO-02081470 A1 | 10/2002 |
| WO | WO-02096890 A2 | 12/2002 |
| WO | WO-02096916 A1 | 12/2002 |
| WO | WO-03022824 A1 | 3/2003 |
| WO | WO-03035648 A1 | 5/2003 |
| WO | WO-03072553 A1 | 9/2003 |
| WO | WO-03072575 A1 | 9/2003 |
| WO | WO-03084534 A1 | 10/2003 |
| WO | WO-2004029066 A2 | 4/2004 |
| WO | WO-2004048392 A1 | 6/2004 |
| WO | WO-2004056817 A1 | 7/2004 |
| WO | WO-2004056818 A1 | 7/2004 |
| WO | WO-2004056819 A1 | 7/2004 |
| WO | WO-2004078753 A1 | 9/2004 |
| WO | WO-2004089943 A1 | 10/2004 |
| WO | WO-2005003087 A2 | 1/2005 |
| WO | WO-2005012270 A2 | 2/2005 |
| WO | WO-2005012271 A2 | 2/2005 |
| WO | WO-2005019211 A2 | 3/2005 |
| WO | WO-2005058886 A1 | 6/2005 |
| WO | WO-2005061468 A1 | 7/2005 |
| WO | WO-2005070904 A2 | 8/2005 |
| WO | WO-2006133397 A2 | 12/2006 |

OTHER PUBLICATIONS

Himo et al. "Copper(1)-Catalyzed Synthesis of Azoles. DFT Study Predicts Unprecedented Reactivity and Intermediates." *J. Am. Chem. Soc.* 127.1(2004):210-216.

Molander et al. "Palladium-Catalyzed Suzuki-Miyaura Cross-Coupling Reactions of Potassium Aryl- and Heteroaryltrifluoroborates." *J. Org. Chem.* 68(2003):4302-4314.

Orgueira et al. "Regioselective synthesis of [1,2,3]-triazoles Catalyzed by C(I) Generated in situ from Cu(O) Nanosize Activated Powder and Amine Hydrochloride Salts." *Tetrahed. Lett.* 46.16(2005):2911-2914.

Park et al. "Antibacterials. Synthesis and Structure -Activity Studies of 3-Aryl-2-Oxazolidinones. 4. Multiply-Substituted Aryl Derivatives." *J. Med. Chem.* 35.6(1992):1156-1165.

Reck et al. "Novel Substituted (Pyridin-3-yl)Phenyloxazolidinones: Antibacterial Agents with Reduced Activity against Monoamine Oxidase A and Increased Solubilit." *J. Med. Chem.* 50(2007):4868-4881.

Rostovtsev et al. "A Stepwise Huisgen Cycloaddition Process: Copper(I)-Catalyzed Regioselective Ligation of Azides and Terinal Alkynes." *Angew. Chemie Int. Ed.* 41.14(2002):2596-2599.

Verkhozina et al. "Synthesis of Polynuclear Nonfused Azoles." *Russian J. Org. Chem.* 39.12(2003):1863-1867.

Wu et al. "Efficiency and Fidelity in a Click-Chemistry Route to Triazole Dendrimers by the Copper(I)-Catalyzed Ligation of Azides and Alkynes." *Angew. Chemie Int. Ed.* 43.30(2004):3928-3932.

Zurenko et al. "Oxazolidinone Antibacterial Agents: Development of the Clinical Candidates Eperezolid and Linezolid." *Exp. Opin. Invest. Drugs.* 6.2(1997):151-158.

PROCESS FOR THE SYNTHESIS OF BIARYL OXAZOLIDINONES

RELATED APPLICATIONS

This application is a continuation of U.S. patent application Ser. No. 10/566,150, filed Oct. 7, 2009, which is a national stage application filed under 35 U.S.C. §371 of International Application No. PCT/US2004/024339, filed Jul. 28, 2004, which claims the benefit of and priority to U.S. Patent Application Ser. Nos. 60/530,371, filed Dec. 17, 2003 and 60/576,163, filed Jun. 2, 2004; International Application No. PCT/US2004/024339 is a continuation-in-part of U.S. patent application Ser. No. 10/859,476 (now U.S. Pat. No. 6,969,726), filed Jun. 2, 2004, which claims the benefit of and priority to U.S. Patent Application Ser. Nos. 60/490,855, filed Jul. 29, 2003; 60/529,731, filed Dec. 15, 2003; and 60/531,584, filed Dec. 19, 2003; the entire enclosures of which are incorporated by reference herein.

FIELD OF THE INVENTION

The present invention relates generally to a process for synthesizing anti-infective, anti-proliferative, anti-inflammatory, and prokinetic agents. More particularly, the invention relates to a process for synthesizing biaryl oxazolidinone compounds that are useful as therapeutic agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken by the fact that strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylocci, penicillin-resistant streptococci, and vancomycin-resistant enterococci have developed, which can cause serious and even fatal results for patients infected with such resistant bacteria. Bacteria that are resistant to macrolide antibiotics, i.e., antibiotics based on a 14- to 16-membered lactone ring, have developed. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, 2003, 111(9), 1265-1273; and Gold, H. S. and Moellering, R. C., Jr., "Antimicrobial-Drug Resistance," *N. Engl. J. Med.*, 1996, 335, 1445-53.

The problem of resistance is not limited to the area of anti-infective agents, because resistance has also been encountered with anti-proliferative agents used in cancer chemotherapy. Therefore, there exists a need for new anti-infective and anti-proliferative agents that are both effective against resistant bacteria and resistant strains of cancer cells.

In the antibiotic area, despite the problem of increasing antibiotic resistance, no new major classes of antibiotics have been developed for clinical use since the approval in the United States in 2000 of the oxazolidinone ring-containing antibiotic, N-[[(5S)-3-[3-fluoro-4-(4-morpholinyl)phenyl]-2-oxo-5-oxazolidinyl]methyl acetamide, which is known as linezolid and is sold under the tradename Zyvox® (see compound A). See, R. C. Moellering, Jr., "Linezolid: The First Oxazolidinone Antimicrobial," *Annals of Internal Medicine*, 2003, 138(2), 135-142.

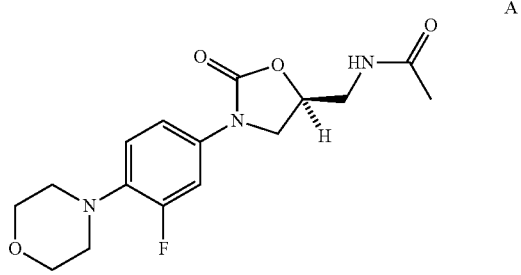 [SMILES: CC(=O)NC[C@H]1CN(c2ccc(N3CCOCC3)c(F)c2)C(=O)O1]

A

Linezolid was approved for use as an anti-bacterial agent active against Gram-positive organisms. Unfortunately, linezolid-resistant strains of organisms are already being reported. See, Tsiodras et al., *Lancet*, 2001, 358, 207; Gonzales et al., *Lancet*, 2001, 357, 1179; Zurenko et al., *Proceedings Of The 39th Annual Interscience Conference On Antibacterial Agents And Chemotherapy (ICAAC)*; San Francisco, Calif., USA, (Sep. 26-29, 1999). Because linezolid is both a clinically effective and commercially significant anti-microbial agent, investigators have been working to develop other effective linezolid derivatives.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents, as well as methods for making such compounds.

SUMMARY OF THE INVENTION

The present invention provides processes for preparing biaryl oxazolidinone compounds having the formula:

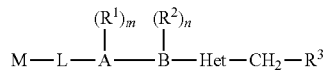

by combining a compound of formula (I):

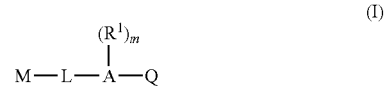

(I)

with a compound of formula (II):

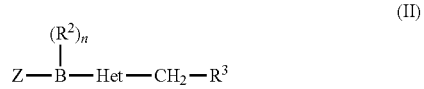

(II)

in a solvent in the presence of a base and a palladium catalyst, wherein Het-CH$_2$—R$^3$ is selected from the group consisting of:

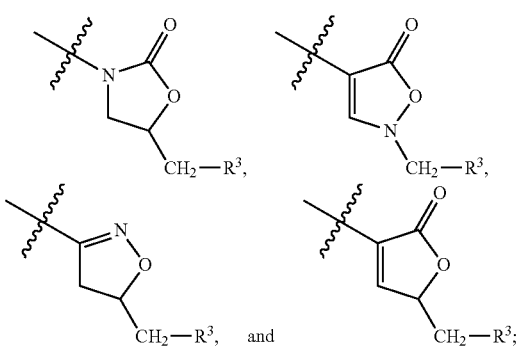

A and B independently are selected from the group consisting of phenyl, pyridyl, pyrazinyl, pyrimidinyl, and pyridazinyl; Q is a borane having the formula $-BY^2$ or a $BF_3$ alkali metal salt; Z is an electronegative substituent (e.g., a halogen or sulfonate); and L, M, $R^1$, $R^2$, $R^3$, Y, m, and n and are defined as described below.

In another approach, the method includes the step of combining a compound of formula (III):

(III)

with a compound of formula (IV):

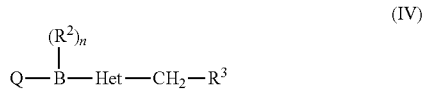

(IV)

in a solvent in the presence of a base and a palladium catalyst, wherein A, B, Het, L, M, $R^1$, $R^2$, $R^3$, Q, Z, m, and n, are defined as described above.

The processes of the invention can tolerate a wide variety of functional groups, so various substituted aryl moieties can be used. In addition, the alternate processes allow for the borane (i.e., Q) and the electronegative substituent (i.e., Z) to be present on either aryl group, which provides synthetic flexibility. The processes generally provide the desired biaryl oxazolidinone compound at or near the end of the overall process, and further synthetic manipulation of the biaryl system or its substituents is generally not necessary.

The foregoing and other aspects and embodiments of the invention can be more fully understood by reference to the following detailed description and claims.

DETAILED DESCRIPTION OF THE INVENTION

The present invention relates to processes for preparing biaryl oxazolidinone compounds useful as anti-proliferative agents and/or anti-infective agents. The compounds may be used without limitation, for example, as anti-cancer, anti-microbial, anti-bacterial, anti-fungal, anti-parasitic and/or anti-viral agents. Further, compounds produced by the processes of the invention can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation.

Compounds synthesized according to the methods of the invention may be used to treat a disorder in a mammal by administering to the mammal an effective amount of one or more compounds of the invention thereby to ameliorate a symptom of a particular disorder. Such a disorder can be selected from the group consisting of a skin infection, nosocomial pneumonia, post-viral pneumonia, an abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant *Enterococci* infection, a linezolid-resistant organism infection, and tuberculosis.

1. Definitions

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R^1$) occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., 3-chloroperoxybenzoic acid (m-CPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_{3-14}$ carbocycle, or 3-14-membered heterocycle) derivatives.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, benzyl, t-butyldimethylsilyl, t-butdyldiphenylsilyl, t-butyloxycarbonyl, p-methoxybenzyl, methoxymethyl, tosyl, trifluoroacetyl, trimethylsilyl, fluorenylmethyloxycarbonyl, 2-trimethylsilyl-ethyoxycarbonyl, 1-methyl-1-(4-biphenylyl)ethoxycarbonyl, allyloxycarbonyl, and benzyloxycarbonyl. Other suitable amine protecting groups are straightforwardly identified by those of skill in the art, e.g., by reference to Green & Wuts, *Protective Groups in Organic Synthesis*, 3d Ed. (1999, John Wiley & Sons, Inc.).

"Stable compound" and "stable structure" are meant to indicate a compound that is sufficiently robust to survive isolation to a useful degree of purity from a reaction mixture, and formulation into an efficacious therapeutic agent.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

2. Processes of the Invention

The processes of the invention involve a Suzuki-type coupling reaction between an aryl borane compound (e.g., an aryl boronic acid, aryl boronic ester, aryl boronic halide, or organoborane) and an aryl compound having an electronegative substituent (e.g., an aryl halide or aryl sulfonate) in a solvent in the presence of a base and a palladium catalyst. See, e.g., Miyaura et al., *Tetrahedron Letters*, 3437 (1979), and Miyaura & Suzuki, *Chem. Comm.*, 866 (1979).

In one aspect, the invention provides processes for synthesizing compounds having the formula:

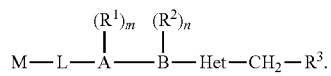

In one approach, the process includes the step of combining a compound of formula (I):

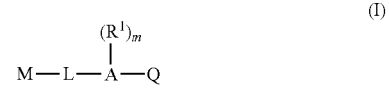

with a compound of formula (II):

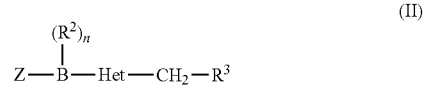

in a solvent in the presence of a base and a palladium catalyst, wherein

A is selected from the group consisting of:

phenyl, pyridyl, pyrazinyl, pyrimidinyl, and pyridazinyl;

B is selected from the group consisting of:

phenyl, pyridyl, pyrazinyl, pyrimidinyl, and pyridazinyl;

Het-CH$_2$—R$^3$ is selected from the group consisting of:

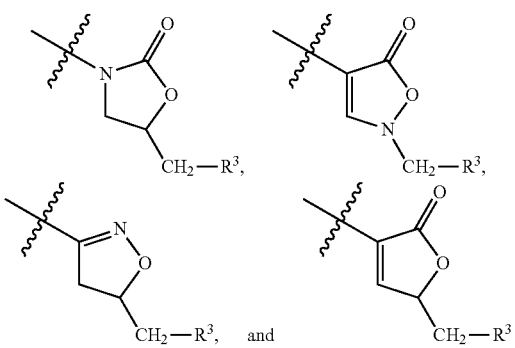

M-L is selected from the group consisting of:

a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X—X—, i) M-L$^1$-X—X—, j) M-X—X-L$^2$, and k) M-L$^1$-X—X-L$^2$, wherein X, at each occurrence, independently is selected from the group consisting of:

a) —O—, b) —NR$^4$, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s)

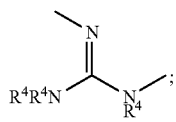

$L^1$ is selected from the group consisting of:
  a) $C_{1-6}$ alkyl, b) $C_{2-6}$ alkenyl, and c) $C_{2-6}$ alkynyl, wherein any of a)-c) optionally is substituted with one or more $R^5$ groups; and $L^2$ is selected from the group consisting of:
  a) $C_{1-6}$ alkyl, b) $C_{2-6}$ alkenyl, and c) $C_{2-6}$ alkynyl, wherein any of a)-c) optionally is substituted with one or more $R^5$ groups;

alternatively, L in M-L is a bond;

M is selected from the group consisting of:
  a) $C_{3-14}$ saturated, unsaturated, or aromatic carbocycle, b) 3-14 membered saturated, unsaturated, or aromatic heterocycle containing one or more heteroatoms selected from the group consisting of nitrogen, oxygen, and sulfur, c) $C_{1-6}$ alkyl, d) $C_{2-6}$ alkenyl, e) $C_{2-6}$ alkynyl, and f) —CN,
    wherein any of a)-e) optionally is substituted with one or more $R^5$ groups;

Q is a borane having the formula —$BY_2$, wherein
Y, at each occurrence, independently is selected from the group consisting of:
  a) —OH, b) —$OC_{1-6}$ alkyl, c) —$OC_{2-6}$ alkenyl, d) —$OC_{2-6}$ alkynyl, e) —$OC_{1-14}$ saturated, unsaturated, or aromatic carbocycle, f) $C_{1-6}$ alkyl, g) $C_{2-6}$ alkenyl, h) $C_{2-6}$ alkynyl, and i) $C_{1-14}$ saturated, unsaturated, or aromatic carbocycle,
    wherein any of b)-i) optionally is substituted with one or more halogens;

alternatively, two Y groups taken together comprise a chemical moiety selected from the group consisting of:
  a) —OC($R^4$)($R^4$)C($R^4$)($R^4$)O—, and b) —OC($R^4$)($R^4$)$CH_2$C($R^4$)($R^4$)O—;

alternatively, Q is a $BF_3$ alkali metal salt or 9-borabicyclo[3.3.1]nonane;

Z is selected from the group consisting of:
  a) I, b) Br, c) Cl, and d) $R^9OSO_3$—;

$R^1$, at each occurrence, independently is selected from the group consisting of:
  a) F, b) Cl, c) Br, d) I, e) —$CF_3$, f) —$OR^4$, g) —CN, h) —$NO_2$, i) —$NR^4R^4$, j) —C(O)$R^4$, k) —C(O)O$R^4$, l) —OC(O)$R^4$, m) —C(O)N$R^4R^4$, n) —$NR^4$C(O)$R^4$, o) —OC(O)N$R^4R^4$, p) —$NR^4$C(O)O$R^4$, q) —$NR^4$C(O)N$R^4R^4$, r) —C(S)$R^4$, s) —C(S)O$R^4$, t) —OC(S)$R^4$, u) —C(S)N$R^4R^4$, v) —$NR^4$C(S)$R^4$, w) —OC(S)N$R^4R^4$, x) —$NR^4$C(S)O$R^4$, y) —$NR^4$C(S)N$R^4R^4$, z) —C($NR^4$)$R^4$, aa) —C($NR^4$)O$R^4$, bb) —OC($NR^4$)$R^4$, cc) —C($NR^4$)N$R^4R^4$, dd) —$NR^4$C($NR^4$)$R^4$, ee) —OC($NR^4$)N$R^4R^4$, ff) —$NR^4$C($NR^4$)O$R^4$, gg) —$NR^4$C($NR^4$)N$R^4R^4$, hh) —S(O)$_pR^4$, ii) —$SO_2$N$R^4R^4$, and jj) $R^4$;

$R^2$, at each occurrence, independently is selected from the group consisting of:
  a) F, b) Cl, c) Br, d) I, e) —$CF_3$, f) —$OR^4$, g) —CN, h) —$NO_2$, i) —$NR^4R^4$, j) —C(O)$R^4$, k) —C(O)O$R^4$, l) —OC(O)$R^4$, m) —C(O)N$R^4R^4$, n) —$NR^4$C(O)$R^4$, o) —OC(O)N$R^4R^4$, p) —$NR^4$C(O)O$R^4$, q) —$NR^4$C(O)N$R^4R^4$, r) —C(S)$R^4$, s) —C(S)O$R^4$, t) —OC(S)$R^4$, u) —C(S)N$R^4R^4$, v) —$NR^4$C(S)$R^4$, w) —OC(S)N$R^4R^4$, x) —$NR^4$C(S)O$R^4$, y) —$NR^4$C(S)N$R^4R^4$, z) —C($NR^4$)$R^4$, aa) —C($NR^4$)O$R^4$, bb) —OC($NR^4$)$R^4$, cc) —C($NR^4$)N$R^4R^4$, dd) —$NR^4$C($NR^4$)$R^4$, ee) —OC($NR^4$)N$R^4R^4$, ff) —$NR^4$C($NR^4$)O$R^4$, gg) —$NR^4$C($NR^4$)N$R^4R^4$, hh) —S(O)$_pR^4$, ii) —$SO_2$N$R^4R^4$, and jj) $R^4$;

$R^3$ is selected from the group consisting of:
  a) —$OR^4$, b) —$NR^4R^4$, c) —C(O)$R^4$, d) —C(O)O$R^4$, e) —OC(O)$R^4$, f) —C(O)N$R^4R^4$, g) —$NR^4$C(O)$R^4$, h) —OC(O)N$R^4R^4$, i) —$NR^4$C(O)O$R^4$, j) —$NR^4$C(O)N$R^4R^4$, k) —C(S)$R^4$, l) —C(S)O$R^4$, m) —OC(S)$R^4$, n) —C(S)N$R^4R^4$, o) —$NR^4$C(S)$R^4$, p) —OC(S)N$R^4R^4$, q) —$NR^4$C(S)O$R^4$, r) —$NR^4$C(S)N$R^4R^4$, s) —C($NR^4$)$R^4$, t) —C($NR^4$)O$R^4$, u) —OC($NR^4$)$R^4$, v) —C($NR^4$)N$R^4R^4$, w) —$NR^4$C($NR^4$)$R^4$, x) —OC($NR^4$)N$R^4R^4$, y) —$NR^4$C($NR^4$)O$R^4$, z) —$NR^4$C($NR^4$)N$R^4R^4$, aa) —S(O)$_pR^4$, bb) —$SO_2$N$R^4R^4$, and cc) $R^4$;

$R^4$, at each occurrence, independently is selected from the group consisting of:
  a) H, b) —$OR^6$, c) an amine protecting group, d) $C_{1-6}$ alkyl, e) $C_{2-6}$ alkenyl, f) $C_{2-6}$ alkynyl, g) $C_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—$C_{1-6}$ alkyl, j) —C(O)—$C_{2-6}$ alkenyl, k) —C(O)—$C_{2-6}$ alkynyl, l) —C(O)—$C_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—$C_{1-6}$ alkyl, o) —C(O)O—$C_{2-6}$ alkenyl, p) —C(O)O—$C_{2-6}$ alkynyl, q) —C(O)O—$C_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur,
    wherein any of d)-r) optionally is substituted with one or more $R^5$ groups;

$R^5$, at each occurrence, is independently selected from the group consisting of:
  a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —C(O)$R^6$, p) —C(O)O$R^6$, q) —OC(O)$R^6$, r) —C(O)N$R^6R^6$, s) —$NR^6$C(O)$R^6$, t) —OC(O)N$R^6R^6$, u) —$NR^6$C(O)O$R^6$, v) —$NR^6$C(O)N$R^6R^6$, w) —C(S)$R^6$, x) —C(S)O$R^6$, y) —OC(S)$R^6$, z) —C(S)N$R^6R^6$, aa) —$NR^6$C(S)$R^6$, bb) —OC(S)N$R^6R^6$, cc) —$NR^6$C(S)O$R^6$, dd) —$NR^6$C(S)N$R^6R^6$, ee) —C($NR^6$)$R^6$, ff) —C($NR^6$)O$R^6$, gg) —OC($NR^6$)$R^6$, hh) —C($NR^6$)N$R^6R^6$, ii) —$NR^6$C($NR^6$)$R^6$, jj) —OC($NR^6$)N$R^6R^6$, kk) —$NR^6$C($NR^6$)O$R^6$, ll) —$NR^6$C($NR^6$)N$R^6R^6$, mm) —S(O)$_pR^6$, nn) —$SO_2$N$R^6R^6$, and oo) $R^6$;

$R^6$, at each occurrence, independently is selected from the group consisting of:
  a) H, b) —$OR^8$, c) an amine protecting group, d) $C_{1-6}$ alkyl, e) $C_{2-6}$ alkenyl, f) $C_{2-6}$ alkynyl, g) $C_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—$C_{1-6}$ alkyl, j) —C(O)—$C_{2-6}$ alkenyl, k) —C(O)—$C_{2-6}$ alkynyl, l) —C(O)—$C_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—$C_{1-6}$ alkyl, o) —C(O)O—C$_{2-6}$ alkenyl, p) —C(O)O—C$_{2-6}$ alkynyl, q) —C(O)O—C$_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur, wherein any of d)-r) optionally is substituted with one or more R$^7$ groups;

R$^7$, at each occurrence, independently is selected from the group consisting of:

a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —C(NR$^8$)R$^8$, ff) —C(NR$^8$)OR$^8$, gg) —OC(NR$^8$)R$^8$, hh) —C(NR$^8$)NR$^8$R$^8$, ii) —NR$^8$C(NR$^8$)R$^8$, jj) —OC(NR$^8$)NR$^8$R$^8$, kk) —NR$^8$C(NR$^8$)OR$^8$, ll) —NR$^8$C(NR$^8$)NR$^8$R$^8$, mm) —S(O)$_p$R$^8$, nn) —SO$_2$NR$^8$R$^8$, oo) C$_{1-6}$ alkyl, pp) C$_{2-6}$ alkenyl, qq) C$_{2-6}$ alkynyl, rr) C$_{3-14}$ saturated, unsaturated, or aromatic carbocycle, and ss) 3-14 membered saturated, unsaturated, or aromatic heterocycle comprising one or more heteroatoms selected from the group consisting of nitrogen, oxygen, and sulfur, wherein any of oo)-ss) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S)NR$^8$R$^8$, —C(NR$^8$)R$^8$, —C(NR$^8$)OR$^8$, —OC(NR$^8$)R$^8$, —C(NR$^8$)NR$^8$R$^8$, —NR$^8$C(NR$^8$)R$^8$, —OC(NR$^8$)NR$^8$R$^8$, —NR$^8$C(NR$^8$)OR$^8$, —NR$^8$C(NR$^8$)NR$^8$R$^8$, —SO$_2$NR$^8$R$^8$, and —S(O)$_p$R$^8$;

R$^8$, at each occurrence, independently is selected from the group consisting of:

a) H, b) an amine protecting group, c) C$_{1-6}$ alkyl, d) C$_{2-6}$ alkenyl, e) C$_{2-6}$ alkynyl, f) C$_{3-14}$ saturated, unsaturated, or aromatic carbocycle, g) 3-14 membered saturated, unsaturated, or aromatic heterocycle comprising one or more heteroatoms selected from the group consisting of nitrogen, oxygen, and sulfur, h) —C(O)—C$_{1-6}$ alkyl, i) —C(O)—C$_{2-6}$ alkenyl, j) —C(O)—C$_{2-6}$ alkynyl, k) —C(O)—C$_{3-14}$ saturated, unsaturated, or aromatic carbocycle, l) —C(O)-3-14 membered saturated, unsaturated, or aromatic heterocycle comprising one or more heteroatoms selected from the group consisting of nitrogen, oxygen, and sulfur, m) —C(O)O—C$_{1-6}$ alkyl, n) —C(O)O—C$_{2-6}$ alkenyl, o) —C(O)O—C$_{2-6}$ alkynyl, p) —C(O)O—C$_{3-14}$ saturated, unsaturated, or aromatic carbocycle, and q) —C(O)O-3-14 membered saturated, unsaturated, or aromatic heterocycle comprising one or more heteroatoms selected from the group consisting of nitrogen, oxygen, and sulfur, wherein any of c)-q) optionally is substituted with one or more moieties selected from the group consisting of F, Cl, Br, I, —CF$_3$, —OH, —OC$_{1-6}$ alkyl, —SH, —SC$_{1-6}$ alkyl, —CN, —NO$_2$, —NH$_2$, —NHC$_{1-6}$ alkyl, —N(C$_{1-6}$ alkyl)$_2$, —C(O)C$_{1-6}$ alkyl, —C(O) OC$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —SO$_2$NH$_2$—, —SO$_2$NHC$_{1-6}$ alkyl, —SO$_2$N(C$_{1-6}$ alkyl)$_2$, and —S(O)$_p$C$_{1-6}$ alkyl;

R$^9$ is selected from the group consisting of:

a) C$_{1-6}$ alkyl, b) phenyl, and c) toluoyl;

wherein any of a)-c) optionally is substituted with one or more moieties selected from the group consisting of F, Cl, Br, and I;

m is 0, 1, 2, 3, or 4;

n is 0, 1, 2, 3, or 4; and p, at each occurrence, independently is 0, 1, or 2.

In an alternative approach, the method includes the step of combining a compound of formula (III):

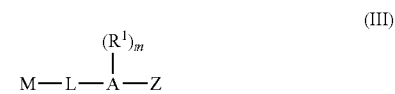

with a compound of formula (IV):

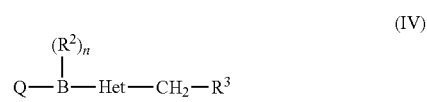

in a solvent in the presence of a base and a palladium catalyst, wherein A, B, Het, L, M, R$^1$, R$^2$, R$^3$, R$^4$, Q, Z, m, and n are defined as described above.

In another aspect, the invention provides processes for preparing a compound having the formula:

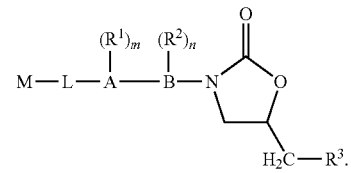

In one approach, the process includes the step of combining a compound of formula (V):

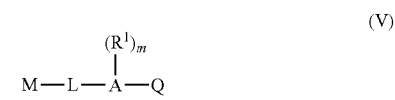

with a compound of formula (VI):

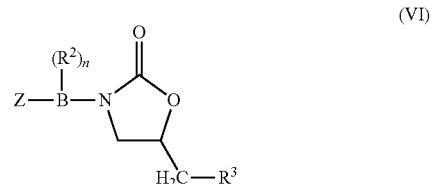

in a solvent in the presence of a base and a palladium catalyst. In an alternative approach, the method includes the step of combining a compound of formula (VII):

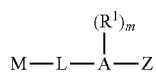
(VII)

with a compound of formula (VIII):

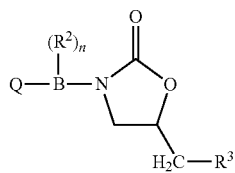
(VIII)

in a solvent in the presence of a base and a palladium catalyst. In either approach, A, B, L, M, $R^1$, $R^2$, $R^3$, Q, Z, m, and n are defined as described above.

In yet another aspect, the invention provides processes for preparing a compound having the formula:

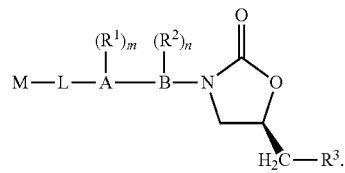

In one approach, the process includes the step of combining a compound of formula (IX):

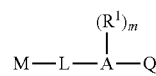
(IX)

with a compound of formula (X):

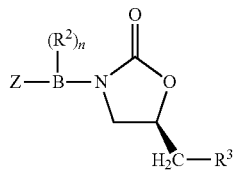
(X)

in a solvent in the presence of a base and a palladium catalyst. Alternatively, the compound can be prepared by combining a compound of formula (XI):

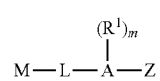
(XI)

with a compound of formula (XII):

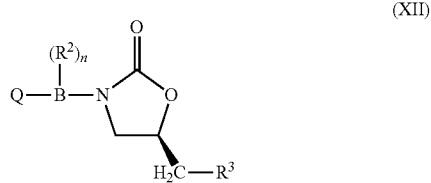
(XII)

in a solvent in the presence of a base and a palladium catalyst. In either approach, A, B, L, M, $R^1$, $R^2$, $R^3$, Q, Z, m, and n are defined as described above.

Embodiments of any of the above processes can include the following:

In preferred compounds, A and B independently are selected from the group consisting of phenyl and pyridyl, and m and n independently are 0, 1, or 2. $R^3$ can be triazole, tetrazole, oxazole, or isoxazole, and particularly [1,2,3]triazol-1-yl. Alternatively, $R^3$ can be —NHC(O)$R^4$, and particularly —NHC(O)CH$_3$.

In various embodiments, compounds (II), (VI), or (X) can have a formula selected from:

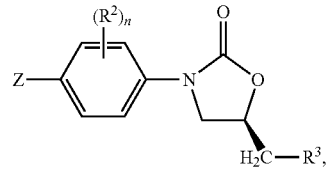

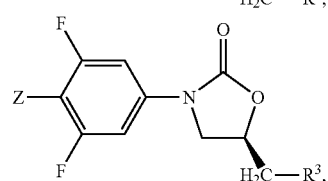

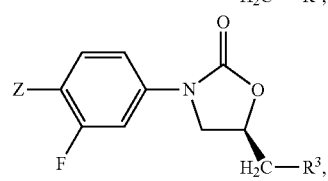

-continued

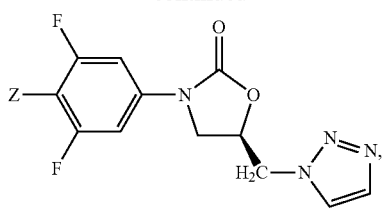

wherein R², R³, Z, and n are defined as described above.

In addition, compounds (I), (V), or (IX) can have a formula selected from:

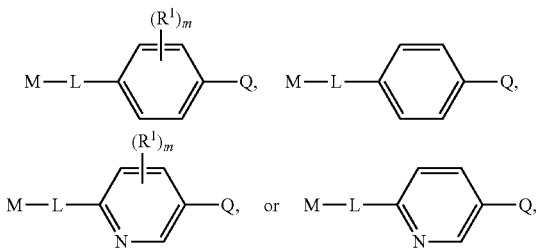

wherein L, M, Q, R¹, and m are defined as described above.

In other embodiments, compounds (IV), (VIII), or (XII) can have a formula selected from:

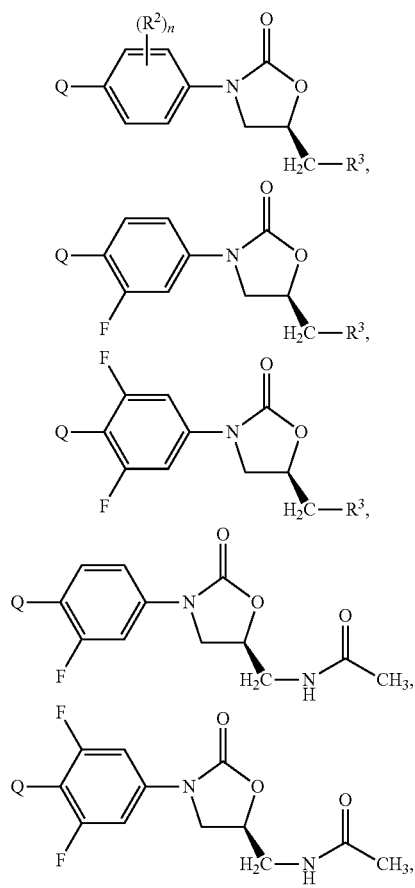

-continued

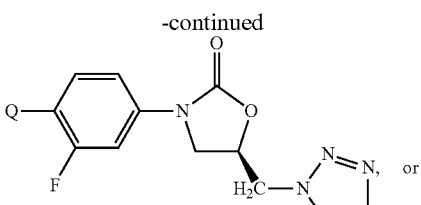

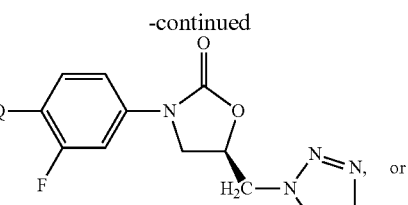

wherein R², R³, Q, and n are defined as described above.

Additionally, compounds (III), (VII), or (XI) can have one of the following formulas:

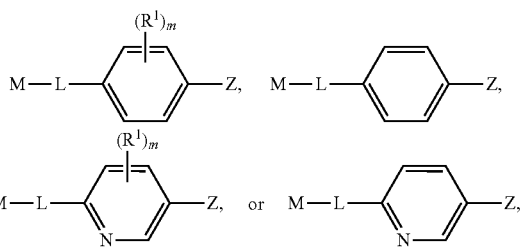

wherein L, M, R¹, Z, and m are defined as described above.

In any of these embodiments, M-L can be M-CH$_2$—X—CH$_2$—. In some embodiments, X is —NR⁴—, where R⁴ can be, for example, H or an amine protecting group. Examples of suitable amine protecting groups include benzyl, t-butyldimethylsilyl, t-butdyldiphenylsilyl, t-butyloxycarbonyl, p-methoxybenzyl, methoxymethyl, tosyl, trifluoroacetyl, trimethylsilyl, fluorenyl-methyloxycarbonyl, 2-trimethylsilyl-ethyoxycarbonyl, 1-methyl-1-(4-biphenylyl)ethoxycarbonyl, allyloxycarbonyl, and benzyloxycarbonyl. In embodiments where R⁴ is an amine protecting group, the processes can include the step of removing the amine protecting group.

In alternative embodiments, M-L is M-S-L¹-NR⁴-L², wherein L¹ and L² are C$_{1-6}$ alkyl. Particularly, M-L can be M-S—CH$_2$CH$_2$—NH—CH$_2$—. In still other embodiments, L is C$_{1-6}$ alkyl, and particularly —CH$_2$—.

In the above embodiments, M can be a 5-6 membered saturated, unsaturated, or aromatic heterocycle comprising one or more heteroatoms selected from the group consisting of nitrogen, oxygen, and sulfur. Examples of suitable heterocycles include triazole, tetrazole, oxazole, and isoxazole, and particularly isoxazol-4-yl, [1,2,3]triazol-1-yl, and [1,2,3]triazol-4-yl.

Alternatively, M-L can be M-X—CH$_2$—. In some embodiments, X is —NR⁴—, where R⁴ can be, for example, H or an amine protecting group, as described above. In embodiments where R⁴ is an amine protecting group, the processes can include the step of removing the amine protecting group. In other embodiments, M-L is

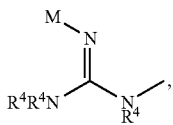

or, more particularly,

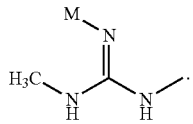

In the above embodiments, M can be a halogenated $C_{1-6}$ alkyl, $C_{2-6}$ alkenyl, or $C_{1-6}$ alkynyl group, optionally substituted with one or more $R^5$ groups, as defined above. Alternatively, M can be a —CN group. In particular embodiments, M is a $C_{1-6}$ alkyl substituted with one or more atoms selected from the group consisting of F, Cl, Br, and I, for example, —$CH_2CH_2CH_2F$. M can also be a $C_{1-6}$ alkyl substituted with one or more —CN groups, for example, —$CH_2CH_2CN$. Other examples of suitable M groups include, but are not limited to, —$CH_2CH(OH)CH_2F$ and —$CH_2C(O)NH_2$.

In alternative embodiments, M is $C_{1-6}$ alkyl, $C_{2-6}$ alkenyl, or $C_{2-6}$ alkynyl, wherein one or more carbons is replaced with $S(O)_p$ and one or more of the remaining carbons optionally is substituted with one or more $R^5$ groups.

Other embodiments include compounds wherein M has the formula:

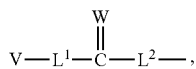

wherein V is H, $NR^4R^4$, —$OR^4$, or $C_{1-6}$ alkyl optionally substituted with one or more $R^5$ groups; W is O or S; and $L^1$ and $L^2$ are defined as described above.

The Z group can be a halogen or a sulfonate. Examples of suitable sulfonates include, but are not limited to, methanesulfonate ("mesylate"), trifluoromethanesulfonate ("triflate"), and p-toluenesulfonate ("tosylate"). In preferred embodiments, the Z group is I. Preferred Q groups include —$B(OH)_2$, —$BF_2.KF$, and

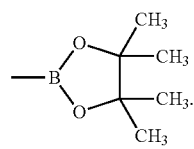

In any of the above processes, the base can be selected from the group consisting of alkali metal hydroxides, alkali metal carbonates, alkali metal fluorides, trialkyl amines, and mixtures thereof. Examples of suitable bases include potassium carbonate, sodium carbonate, sodium methoxide, sodium ethoxide, potassium fluoride, triethylamine, diisopropylethylamine, and mixtures thereof. In certain embodiments, the ratio of equivalents of base to equivalents of compound (I), (IV), (V), (VIII), (a), or (XII) is about 3:1.

The catalyst can be a palladium catalyst, for example, a ligand coordinated palladium(0) catalyst (e.g., a tetrakis(trialkylphosphine)palladium(0) or a tetrakis(triarylphosphine)palladium(0) catalyst) or a ligand coordinated palladium(II) catalyst. Suitable catalysts include, for example, tetrakis(triphenylphosphine)palladium(0), dichloro[1,1'-bis(diphenylphosphino) ferrocene]palladium(II), dichlorobis(triphenylphosphine)palladium(II), palladium(II) acetate, and palladium(II) chloride. In particular embodiments, the catalyst is tetrakis(triphenylphosphine) palladium(0), and the ratio of the equivalents of the catalyst to the equivalents of compound (I), (IV), (V), (VIII), (IX), or (XII) is about 1:20.

The solvent can be an aqueous solvent, or a mixture of water and an organic solvent, wherein the organic solvent is selected from the group consisting of methanol, ethanol, propanol, isopropanol, butanol, isobutanol, secondary butanol, tertiary butanol, benzene, toluene, tetrahydrofuran, dimethylformamide, 1,2-diethyl ether, dimethoxyethane, diisopropyl ether, methyltertiarybutyl ether, methoxymethyl ether, 2-methoxyethyl ether, 1,4-dioxane, 1,3-dioxolane, and mixtures thereof. In particular embodiments, the solvent is a mixture of water, toluene, and ethanol, for example, in a ratio of about 1:3:1 by volume.

The process can be carried out at a temperature of about 20° C. to about 100° C. In some embodiments, the process is carried out at the reflux temperature of the solvent.

Other reaction conditions for the Suzuki-type coupling reactions of the invention are straightforwardly identified by those of skill in the art, e.g., by reference to Suzuki & Brown, *Organic Synthesis Via Boranes Volume 3: Suzuki Coupling*, (Aldrich, 2003).

Table 1 includes exemplary compounds that can be synthesized according to the processes of the invention.

TABLE 1

| Compound Number | Structure |
|---|---|
| 1 | ![structure] |

(5S)N-[3-(2-Fluoro-4'-{[(quinolin-4-ylmethyl)-amino]-methyl}-biphenyl-4-yl)-2-oxo-oxazolidin-5-ylmethyl]-acetamide TABLE 1-continued

| Compound Number | Structure |
|---|---|
| 2 | (5S)N-[3-(2-Fluoro-4'-{[([1,2,3]thiadiazol-4-ylmethyl)-amino]-methyl}-biphenyl-4-yl)-2-oxo-oxazolidin-5-ylmethyl]-acetamide |
| 3 | (5S)N-{3-[3-Fluoro-4-(6-tetrazol-1-ylmethyl-pyridin-3-yl)-phenyl]-2-oxo-oxazolidin-5-ylmethyl}-acetamide |
| 4 | (5S)N-[3-(2-Fluoro-4'-[1,2,3]triazol-1-ylmethyl-biphenyl-4-yl)-2-oxo-oxazolidin-5-ylmethyl]-acetamide |
| 5 | (5S)N-[3-(2-Fluoro-4'-{[(isoxazol-4-ylmethyl)-amino]-methyl}-biphenyl-4-yl)-2-oxo-oxazolidin-5-ylmethyl]-acetamide |
| 6 | (5S)N-[3-(2-Fluoro-4'-{[(3H-[1,2,3]triazol-4-ylmethyl)-amino]-methyl}-biphenyl-4-yl)-2-oxo-oxazolidin-5-ylmethyl]-acetamide |

TABLE 1-continued

| Compound Number | Structure |
|---|---|
| 7 | 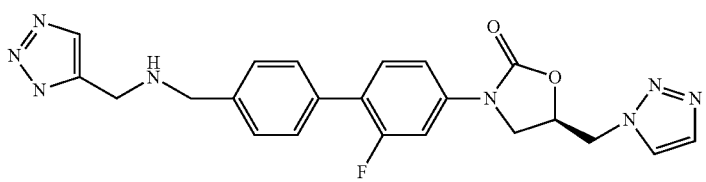<br>(5R)3-(2-Fluoro-4'-{[(3H-[1,2,3]triazol-4-ylmethyl)-amino]-methyl}-biphenyl-4-yl)-5-[1,2,3]triazol-1-ylmethyl-oxazolidin-2-one |
| 8 | 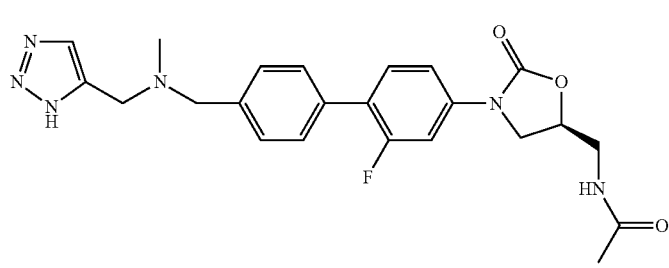 [SMILES: CC(=O)NC[C@H]1CN(c2ccc(-c3ccc(CNCc4cnn[nH]4)cc3)c(F)c2)C(=O)O1]<br>(5S)N-[3-(2-Fluoro-4'-{[methyl-(3H-[1,2,3]triazol-4-ylmethyl)-amino]-methyl}-biphenyl-4-yl)-2-oxo-oxazolidin-5-ylmethyl]-acetamide |
| 9 | 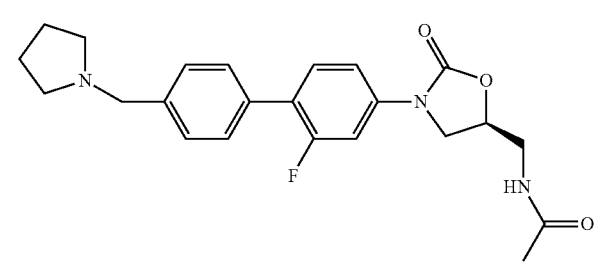 [SMILES: CC(=O)NC[C@H]1CN(c2ccc(-c3ccc(CN4CCCC4)cc3)c(F)c2)C(=O)O1]<br>(5S)N-[3-(2-Fluoro-4'-pyrrolidin-1-ylmethyl-biphenyl-4-yl)-2-oxo-oxazolidin-5-ylmethyl]-acetamide |
| 10 | 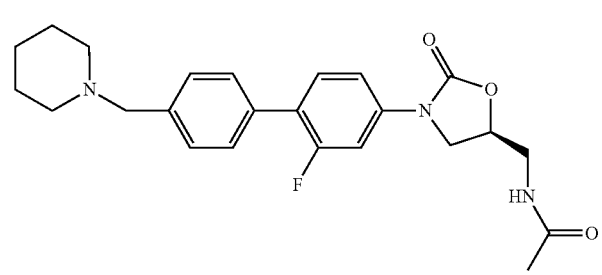 [SMILES: CC(=O)NC[C@H]1CN(c2ccc(-c3ccc(CN4CCCCC4)cc3)c(F)c2)C(=O)O1]<br>(5S)N-[3-(2-Fluoro-4'-piperidin-1-ylmethyl-biphenyl-4-yl)-2-oxo-oxazolidin-5-ylmethyl]-acetamide |
| 11 | 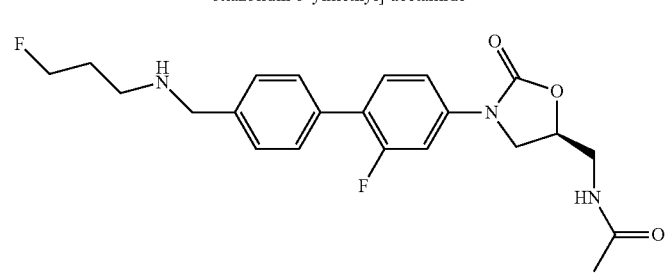<br>(5S)N-(3-{2-Fluoro-4'-[(3-fluoro-propylamino)-methyl]-biphenyl-4-yl}-2-oxo-oxazolidin-5-ylmethyl)-acetamide |

TABLE 1-continued

| Compound Number | Structure |
|---|---|
| 12 | (5S)N-(3-{4'-[(2-Cyano-ethylamino)-methyl]-2-fluoro-biphenyl-4-yl}-2-oxo-oxazolidin-5-ylmethyl)-acetamide |
| 13 | (5S)N-{3-[4-(4-N-(N-methyl-N'-cyano)guanylaminomethyl-phenyl-4-yl)-3-fluorophenyl]-2-oxo-oxazolidin-5-ylmethyl}-acetamide |
| 14 | (5R)2-{[2'-Fluoro-4'-(2-oxo-5-[1,2,3]triazol-1-ylmethyl-oxazolidin-3-yl)-biphenyl-4-ylmethyl]-amino}-acetamide |
| 15 | (5S)N-(3-{2-Fluoro-4'-[(3-fluoro-2-hydroxy-propylamino)-methyl]-biphenyl-4-yl}-2-oxo-oxazolidin-5-ylmethyl)-acetamide |
| 16 | (5R)3-{2-Fluoro-4'-[(3-fluoro-propylamino)-methyl]-biphenyl-4-yl}-5-[1,2,3]triazol-1-ylmethyl-oxazolidin-2-one |

TABLE 1-continued

| Compound Number | Structure |
|---|---|
| 17 | 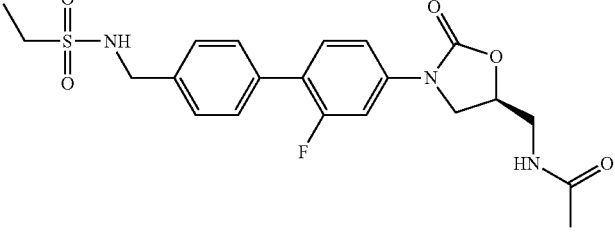<br>(5S)N-{3-[4'-(Ethanesulfonylamino-methyl)-2-fluoro-biphenyl-4-yl]-2-oxo-oxazolidin-5-ylmethyl}-acetamide |
| 18 | 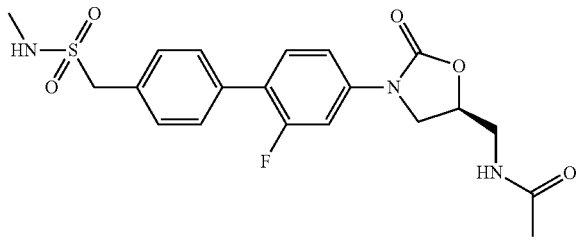 [SMILES: CNS(=O)(=O)Cc1ccc(-c2ccc(N3C[C@H](CNC(C)=O)OC3=O)cc2F)cc1]<br>(5S)N-[3-(2-Fluoro-4'-methylsulfamoylmethyl-biphenyl-4-yl)-2-oxo-oxazolidin-5-ylmethyl]-acetamide |
| 19 | 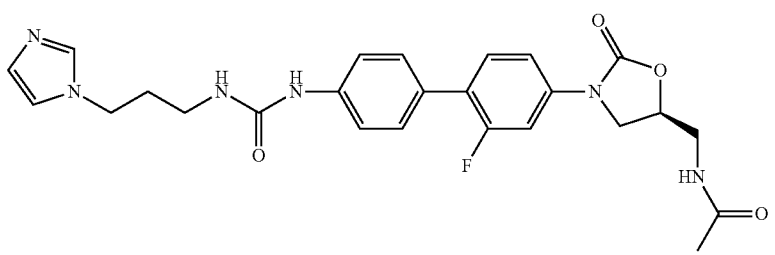 [SMILES: CC(=O)NC[C@H]1CN(c2ccc(-c3ccc(NC(=O)NCCCn4ccnc4)cc3)c(F)c2)C(=O)O1]<br>(5S)N-(3-{2-Fluoro-4'-[3-(3-imidazol-1-yl-propyl)-ureido]-biphenyl-4-yl}-2-oxo-oxazolidin-5-ylmethyl)-acetamide |
| 20 | 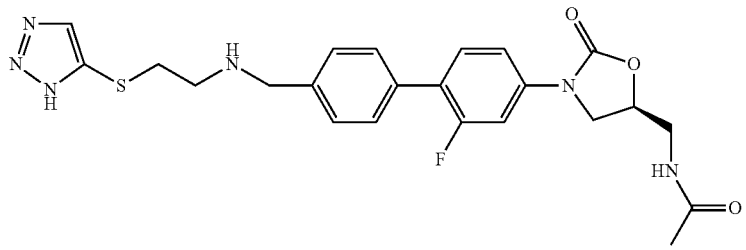 [SMILES: CC(=O)NC[C@H]1CN(c2ccc(-c3ccc(CNCCSc4cnn[nH]4)cc3)c(F)c2)C(=O)O1]<br>(5S)N-[3-(2-Fluoro-4'-{[2-(3H-[1,2,3]triazol-4-ylsulfanyl)-ethylamino]-methyl}-biphenyl-4-yl)-2-oxo-oxazolidin-5-ylmethyl]-acetamide |
| 21 | 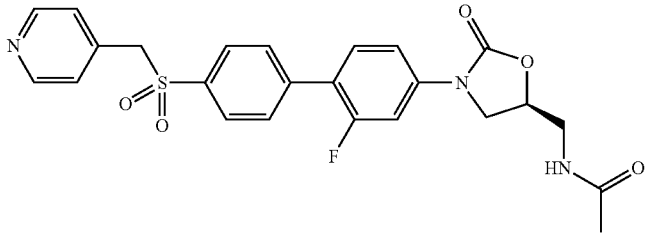 [SMILES: CC(=O)NC[C@H]1CN(c2ccc(-c3ccc(S(=O)(=O)Cc4ccncc4)cc3)c(F)c2)C(=O)O1]<br>(5S)N-{3-[2-Fluoro-4'-(pyridin-4-ylmethanesulfonyl)-biphenyl-4-yl]-2-oxo-oxazolidin-5-ylmethyl}-acetamide |

TABLE 1-continued

| Compound Number | Structure |
|---|---|
| 22 | 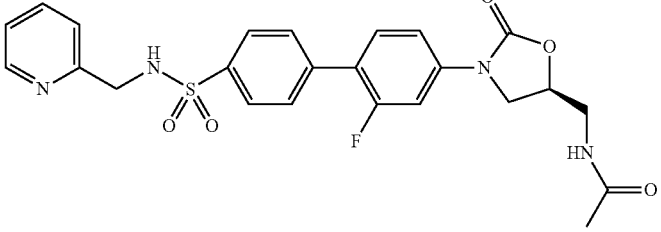
(5S)N-(3-{2-Fluoro-4'-[(pyridin-2-ylmethyl)-sulfamoyl]-biphenyl-4-yl}-2-oxo-oxazolidin-5-ylmethyl)-acetamide |
| 23 | 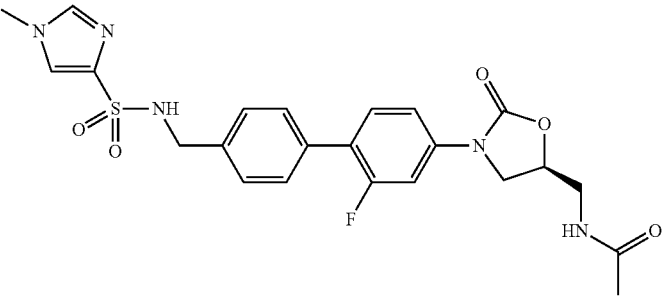 [SMILES: CC(=O)NC[C@H]1CN(c2ccc(-c3ccc(CNS(=O)(=O)c4cn(C)cn4)cc3)c(F)c2)C(=O)O1]
(5S)N-(3-{2-Fluoro-4'-[(1-methyl-1H-imidazole-4-sulfonylamino)-methyl]-biphenyl-4-yl}-2-oxo-oxazolidin-5-ylmethyl)-acetamide |
| 24 | 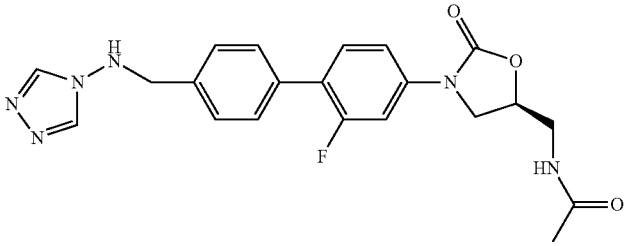 [SMILES: CC(=O)NC[C@H]1CN(c2ccc(-c3ccc(CNn4cnnc4)cc3)c(F)c2)C(=O)O1]
(5S)N-{3-[2-Fluoro-4'-([1,2,4]triazol-4-ylaminomethyl)-biphenyl-4-yl]-2-oxo-oxazolidin-5-ylmethyl}-acetamide |
| 25 | 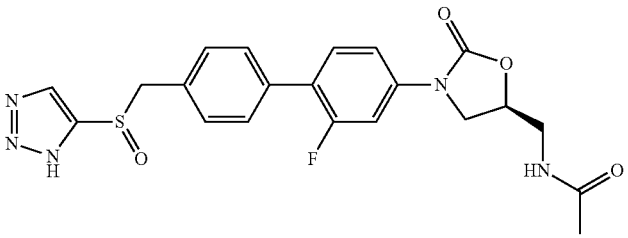 [SMILES: CC(=O)NC[C@H]1CN(c2ccc(-c3ccc(CS(=O)c4cnn[nH]4)cc3)c(F)c2)C(=O)O1]
(5S)N-{3-[2-Fluoro-4'-(3H-[1,2,3]triazole-4-sulfonylmethyl)-biphenyl-4-yl]-2-oxo-oxazolidin-5-ylmethyl}-acetamide |
| 26 | 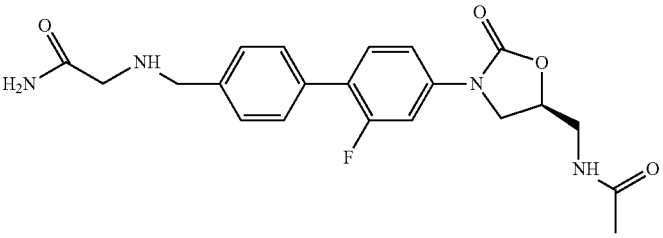 [SMILES: CC(=O)NC[C@H]1CN(c2ccc(-c3ccc(CNCC(N)=O)cc3)c(F)c2)C(=O)O1]
(5S)2-({4'-[5-(Acetylamino-methyl)-2-oxo-oxazolidin-3-yl]-2'-fluoro-biphenyl-4-ylmethyl}-amino)-acetamide |

TABLE 1-continued

| Compound Number | Structure |
|---|---|
| 27 | 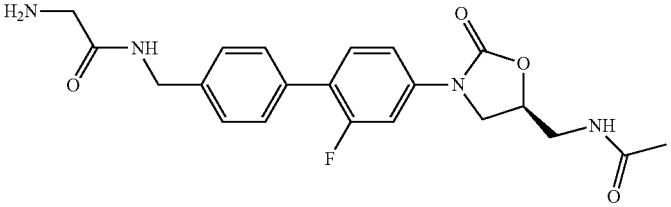 [SMILES: CC(=O)NC[C@H]1CN(c2ccc(-c3ccc(CNC(=O)CN)cc3)c(F)c2)C(=O)O1]<br>(5S)N-{4'-[5-(Acetylamino-methyl)-2-oxo-oxazolidin-3-yl]-2'-fluoro-biphenyl-4-ylmethyl}-2-amino-acetamide |
| 28 | 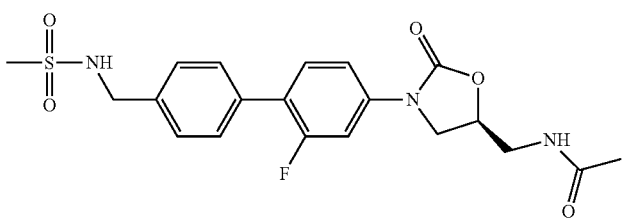 [SMILES: CC(=O)NC[C@H]1CN(c2ccc(-c3ccc(CNS(C)(=O)=O)cc3)c(F)c2)C(=O)O1]<br>(5S)N-{3-[2-Fluoro-4'-(methanesulfonylamino-methyl)-biphenyl-4-yl]-2-oxo-oxazolidin-5-ylmethyl}-acetamide |
| 29 | 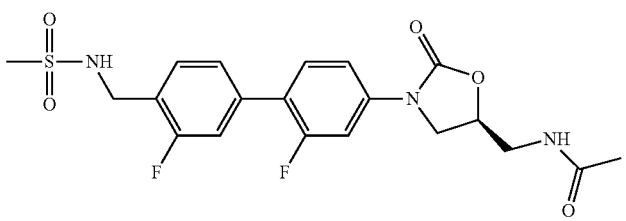 [SMILES: CC(=O)NC[C@H]1CN(c2ccc(-c3ccc(CNS(C)(=O)=O)c(F)c3)c(F)c2)C(=O)O1]<br>(5S)N-{3-[2,3'-Difluoro-4'-(methanesulfonylamino-methyl)-biphenyl-4-yl]-2-oxo-oxazolidin-5-ylmethyl}-acetamide |
| 30 | 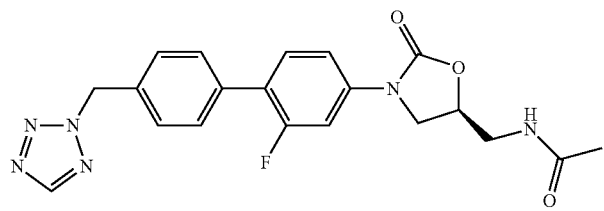 [SMILES: CC(=O)NC[C@H]1CN(c2ccc(-c3ccc(Cn4ncnn4)cc3)c(F)c2)C(=O)O1]<br>(5S)N-[3-(2-Fluoro-4'-tetrazol-2-ylmethyl-biphenyl-4-yl)-2-oxo-oxazolidin-5-ylmethyl]-acetamide |
| 31 | 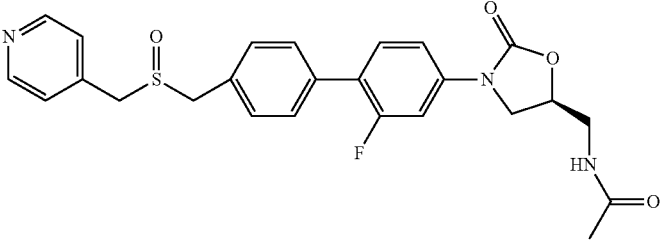 [SMILES: CC(=O)NC[C@H]1CN(c2ccc(-c3ccc(CS(=O)Cc4ccncc4)cc3)c(F)c2)C(=O)O1]<br>(5S)N-{3-[2-Fluoro-4'-(pyridin-4-ylmethanesulfinylmethyl)-biphenyl-4-yl]-2-oxo-oxazolidin-5-ylmethyl}-acetamide |

TABLE 1-continued

| Compound Number | Structure |
|---|---|
| 32 | (5S)N-{3-[3-Fluoro-4-(6-tetrazol-1-ylmethyl-pyridin-3-yl)-phenyl]-2-oxo-oxazolidin-5-ylmethyl}-acetamide |
| 33 | (5S)N-{3-[3-Fluoro-4-(6-[1,2,3]triazol-1-ylmethyl-pyridin-3-yl)-phenyl]-2-oxo-oxazolidin-5-ylmethyl}-acetamide |
| 34 | (5S)N-{3-[2-Fluoro-4'-([1,3,4]thiadiazole-2-sulfinylmethyl)-biphenyl-4-yl]-2-oxo-oxazolidin-5-ylmethyl}-acetamide |
| 35 | (5S)N-[3-(2-Fluoro-4'-[1,2,4]triazol-1-ylmethyl-biphenyl-4-yl)-2-oxo-oxazolidin-5-ylmethyl]-acetamide |
| 36 | (5S)N-{3-[2-Fluoro-4'-(5-methyl-tetrazol-1-ylmethyl)-biphenyl-4-yl]-2-oxo-oxazolidin-5-ylmethyl}-acetamide |

TABLE 1-continued

| Compound Number | Structure |
|---|---|
| 37 | (5S)N-{3-[2-Fluoro-4'-(5-methyl-tetrazol-2-ylmethyl)-biphenyl-4-yl]-2-oxo-oxazolidin-5-ylmethyl}-acetamide |
| 38 | (S,S)N-{3-[2-Fluoro-4'-(1-hydroxy-2-[1,2,3]triazol-1-yl-ethyl)-biphenyl-4-yl]-2-oxo-oxazolidin-5-ylmethyl}-acetamide |
| 39 | (5S)N-(3-{2-Fluoro-4'-[(2-methylsulfanyl-ethylamino)-methyl]-biphenyl-4-yl}-2-oxo-oxazolidin-5-ylmethyl)-acetamide |
| 40 | (5S)N-{3-[3-Fluoro-4-(6-[1,2,4]triazol-1-ylmethyl-pyridin-3-yl)-phenyl]-2-oxo-oxazolidin-5-ylmethyl}-acetamide |
| 41 | (5S)N-(3-{4'-[(Acetyl-cyanomethyl-amino)-methyl]-2-fluoro-biphenyl-4-yl}-2-oxo-oxazolidin-5-ylmethyl)-acetamide |

TABLE 1-continued

| Compound Number | Structure |
|---|---|
| 42 | (5S)N-{3-[3-Fluoro-4-(6-pyrazol-1-ylmethyl-pyridin-3-yl)-phenyl]-2-oxo-oxazolidin-5-ylmethyl}-acetamide |
| 43 | (5S)N-{3-[4'-(5-Chloro-tetrazol-1-ylmethyl)-2-fluoro-biphenyl-4-yl]-2-oxo-oxazolidin-5-ylmethyl}-acetamide |
| 44 | (5R)3-(2-Fluoro-4'-imidazol-1-ylmethyl-biphenyl-4-yl)-5-[1,2,3]triazol-1-ylmethyl-oxazolidin-2-one |
| 45 | (5S)N-[3-(2-Fluoro-4'-prop-2-ynylaminomethyl-biphenyl-4-yl)-2-oxo-oxazolidin-5-ylmethyl]-acetamide |
| 46 | (5S)N-[3-(4'-Allylaminomethyl-2-fluoro-biphenyl-4-yl)-2-oxo-oxazolidin-5-ylmethyl]-acetamide |

TABLE 1-continued

| Compound Number | Structure |
|---|---|
| 47 | (5S)N-[3-(4'-But-3-enylaminomethyl-2-fluoro-biphenyl-4-yl)-2-oxo-oxazolidin-5-ylmethyl]-acetamide |
| 48 | (5S)N-[3-(4'-But-3-ynylaminomethyl-2-fluoro-biphenyl-4-yl)-2-oxo-oxazolidin-5-ylmethyl]-acetamide |
| 49 | (5S)N-[3-(2-Fluoro-4'-pent-4-ynylaminomethyl-biphenyl-4-yl)-2-oxo-oxazolidin-5-ylmethyl]-acetamide |
| 50 | (5S)N-[3-(4'-But-2-ynylaminomethyl-2-fluoro-biphenyl-4-yl)-2-oxo-oxazolidin-5-ylmethyl]-acetamide |
| 51 | (5S)N-{3-[2-Fluoro-4'-(3-fluoro-piperidin-1-ylmethyl)-biphenyl-4-yl]-2-oxo-oxazolidin-5-ylmethyl}-acetamide |

TABLE 1-continued

| Compound Number | Structure |
|---|---|
| 52 | (5S)N-[3-(2-Fluoro-4'-{[3-(3H-[1,2,3]triazol-4-yl)-propylamino]-methyl}-biphenyl-4-yl)-2-oxo-oxazolidin-5-ylmethyl]-acetamide |
| 53 | (5S)N-(3-{4'-[(2,2-Difluoro-ethylamino)-methyl]-2-fluoro-biphenyl-4-yl}-2-oxo-oxazolidin-5-ylmethyl)-acetamide |
| 54 | (5R)3-(2-Fluoro-4'-prop-2-ynylaminomethyl-biphenyl-4-yl)-5-[1,2,3]triazol-1-ylmethyl-oxazolidin-2-one |
| 55 | (5S)N-[3-(2-Fluoro-4'-isoxazolidin-2-ylmethyl-biphenyl-4-yl)-2-oxo-oxazolidin-5-ylmethyl]-acetamide |
| 56 | (5S) N-{3-[4-(6-Cyano-pyridin-3-yl)-3-fluoro-phenyl]-2-oxo-oxazolidin-5-ylmethyl}-acetamide |

TABLE 1-continued

| Compound Number | Structure |
|---|---|
| 57 | (5S)N-(3-{2-Fluoro-4'-[(1-methyl-prop-2-ynylamino)-methyl]-biphenyl-4-yl}-2-oxo-oxazolidin-5-ylmethyl)-acetamide |
| 58 | (5S)N-{3-[3-Fluoro-4-(6-{[(3H-[1,2,3]triazol-4-ylmethyl)-amino]-methyl}-pyridin-3-yl)-phenyl]-2-oxo-oxazolidin-5-ylmethyl}-acetamide |
| 59 | (5S)N-[3-(2-Fluoro-4'-{[(1-methyl-1H-tetrazol-5-ylmethyl)-amino]-methyl}-biphenyl-4-yl)-2-oxo-oxazolidin-5-ylmethyl]-acetamide |
| 60 | (5S)N-[3-(2-Fluoro-4'-{[(2-methyl-2H-tetrazol-5-ylmethyl)-amino]-methyl}-biphenyl-4-yl)-2-oxo-oxazolidin-5-ylmethyl]-acetamide |
| 61 | (5S)N-(3-{2-Fluoro-4'-[(2-fluoro-allylamino)-methyl]-biphenyl-4-yl}-2-oxo-oxazolidin-5-ylmethyl)-acetamide |

TABLE 1-continued

| Compound Number | Structure |
|---|---|
| 62 | 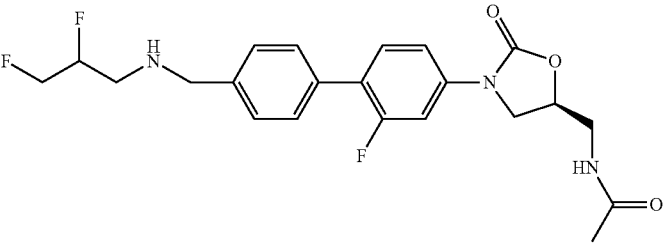 [SMILES: CC(=O)NC[C@H]1CN(c2ccc(-c3ccc(CNCC(F)CF)cc3)c(F)c2)C(=O)O1]<br>(5S)N-(3-{4'-[(2,3Difluoropropylamino)-methyl]-2-fluoro-biphenyl-4-yl}-2-oxo-oxazolidin-5-ylmethyl)-acetamide |
| 63 | 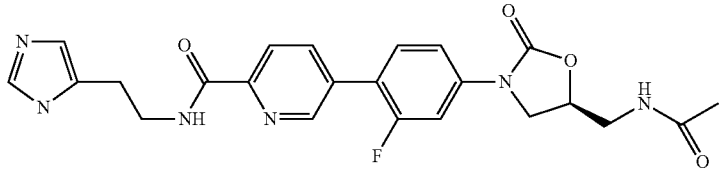 [SMILES: CC(=O)NC[C@H]1CN(c2ccc(-c3ccc(C(=O)NCCc4cnc[nH]4)nc3)c(F)c2)C(=O)O1]<br>(5S)5-{4-[5-(Acetylamino-methyl)-2-oxo-oxazolidin-3-yl]-2-fluoro-phenyl}-pyridine-2-carboxylic acid [2-(3H-imidazol-4-yl)-ethyl]-amide |
| 64 | 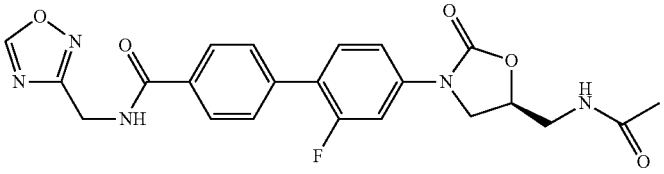<br>(5S)4'-[5-(Acetylamino-methyl)-2-oxo-oxazolidin-3-yl]-2'-fluoro-biphenyl-4-carboxylic acid ([1,2,4]oxadiazol-3-ylmethyl)-amide |
| 65 | 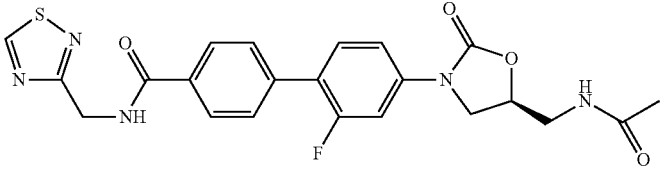 [SMILES: CC(=O)NC[C@H]1CN(c2ccc(-c3ccc(C(=O)NCc4ncon4)cc3)c(F)c2)C(=O)O1]<br>(5S)4'-[5-(Acetylamino-methyl)-2-oxo-oxazolidin-3-yl]-2'-fluoro-biphenyl-4-carboxylic acid ([1,2,4]thiadiazol-3-ylmethyl)-amide |
| 66 | 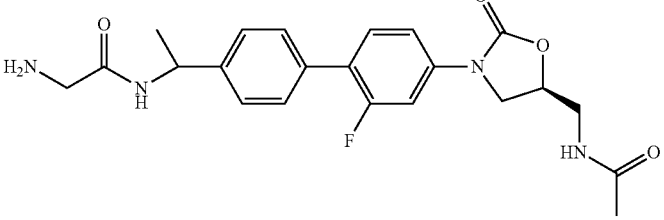<br>(5S)N-(1-{4'-[5-(Acetylamino-methyl)-2-oxo-oxazolidin-3-yl]-2'-fluoro-biphenyl-4-yl}-ethyl)-2-amino-acetamide |

TABLE 1-continued

| Compound Number | Structure |
|---|---|
| 67 | (5S)2-(1-{4'-[5-(Acetylamino-methyl)-2-oxo-oxazolidin-3-yl]-2'-fluoro-biphenyl-4-yl}-ethylamino)-acetamide |
| 68 | (5S)N-{3-[2-Fluoro-4'-(pyridin-4-ylmethylsulfanyl)-biphenyl-4-yl]-2-oxo-oxazolidin-5-ylmethyl}-acetamide |
| 69 | (5S)N-(3-{2-Fluoro-4'-[(pyridin-4-ylmethyl)-sulfamoyl]-biphenyl-4-yl}-2-oxo-oxazolidin-5-ylmethyl)-acetamide |
| 70 | (S,S)N-(3-{2-Fluoro-4'-[2-(3-fluoro-propylamino)-1-hydroxy-ethyl]-biphenyl-4-yl}-2-oxo-oxazolidin-5-ylmethyl)-acetamide |
| 71 | (5S)N-{3-[2-Fluoro-4'-(5-oxo-2,5-dihydro-[1,2,4]oxadiazol-3-ylmethyl)-biphenyl-4-yl]-2-oxo-oxazolidin-5-ylmethyl}-acetamide |

TABLE 1-continued

| Compound Number | Structure |
|---|---|
| 72 | (5S)N-{3-[2-Fluoro-4'-(5-methyl-[1,2,4]oxadiazol-3-ylmethyl)-biphenyl-4-yl]-2-oxo-oxazolidin-5-ylmethyl}-acetamide |
| 73 | (5S)N-[3-(2-Fluoro-4'-{2-[(tetrahydro-furan-2-ylmethyl)-amino]-thiazol-4-ylmethyl}-biphenyl-4-yl)-2-oxo-oxazolidin-5-ylmethyl]-acetamide |
| 74 | (5S)N-(3-{2-Fluoro-4'-[2-(3-methoxy-benzylamino)-thiazol-4-ylmethyl]-biphenyl-4-yl}-2-oxo-oxazolidin-5-ylmethyl)-acetamide |
| 75 | (S,S)N-{3-[4'-(1-Amino-2-imidazol-1-yl-ethyl)-2-fluoro-biphenyl-4-yl]-2-oxo-oxazolidin-5-ylmethyl}-acetamide |

TABLE 1-continued

| Compound Number | Structure |
|---|---|
| 76 | (5S)5-Aminomethyl-3-(2-fluoro-4'-tetrazol-1-ylmethyl-biphenyl-4-yl)-oxazolidin-2-one |
| 77 | (S,S)N-(3-{2-Fluoro-4'-[2-(4-formyl-piperazin-1-yl)-1-hydroxy-ethyl]-biphenyl-4-yl}-2-oxo-oxazolidin-5-ylmethyl)-acetamide |
| 78 | (R,S)N-(3-{2-Fluoro-4'-[1-(4-formyl-piperazin-1-yl)-2-hydroxy-ethyl]-biphenyl-4-yl}-2-oxo-oxazolidin-5-ylmethyl)-acetamide |
| 79 | (S,S)N-{3-[2-Fluoro-4'-(1-hydroxy-2-imidazol-1-yl-ethyl)-biphenyl-4-yl]-2-oxo-oxazolidin-5-ylmethyl}-acetamide |
| 80 | (5S)2,2-Difluoro-N-(3-{2-fluoro-4'-[(3-fluoro-propylamino)-methyl]-biphenyl-4-yl}-2-oxo-oxazolidin-5-ylmethyl)-acetamide |

TABLE 1-continued

| Compound Number | Structure |
|---|---|
| 81 | 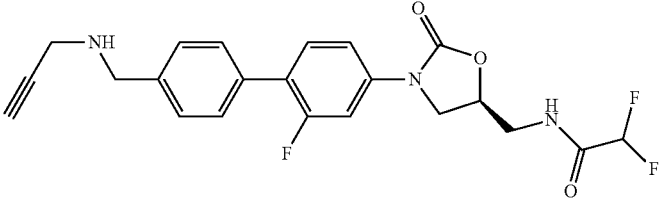 [SMILES: C#CCNCc1ccc(-c2ccc(N3C[C@H](CNC(=O)C(F)F)OC3=O)cc2F)cc1]<br>(5S)2,2-Difluoro-N-[3-(2-fluoro-4'-prop-2-ynylaminomethyl-biphenyl-4-yl)-2-oxo-oxazolidin-5-ylmethyl]-acetamide |

The exemplary compounds in Table 1 can be synthesized by the process depicted in Scheme A using, for example, the aryl boronic acids and aryl iodides listed in Table 2, below.

Scheme A

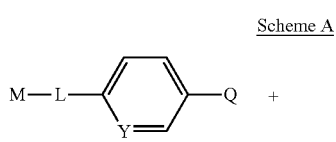
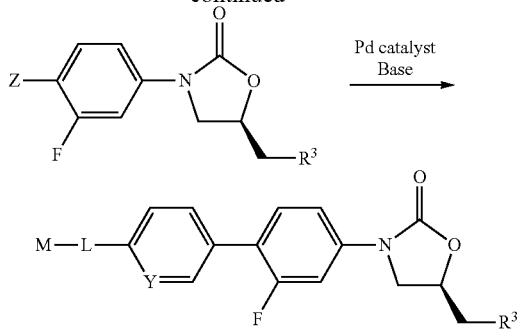

TABLE 2

| M | L | Y | Q | Z | R³ | Product |
|---|---|---|---|---|---|---|
| quinolin-4-yl | —CH₂NHCH₂—* | CH | B(OH)₂ | I | —NHAc | 1 |
| 1,2,3-thiadiazol-4-yl | —CH₂NHCH₂—* | CH | B(OH)₂ | I | —NHAc | 2 |
| tetrazol-1-yl | —CH₂— | CH | B(OH)₂ | I | —NHAc | 3 |
| 1,2,3-triazol-1-yl | —CH₂— | CH | B(OH)₂ | I | —NHAc | 4 |
| isoxazol-4-yl | —CH₂NHCH₂—* | CH | B(OH)₂ | I | —NHAc | 5 |

TABLE 2-continued

| M | L | Y | Q | Z | R³ | Product |
|---|---|---|---|---|----|---------|
| 1H-1,2,3-triazol-5-yl | —CH₂NHCH₂—* | CH | B(OH)₂ | I | —NHAc | 6 |
| 1H-1,2,3-triazol-5-yl | —CH₂NHCH₂—* | CH | B(OH)₂ | I | 1H-1,2,3-triazol-1-yl | 7 |
| 1H-1,2,3-triazol-5-yl | —CH₂N(CH₃)CH₂— | CH | B(OH)₂ | I | —NHAc | 8 |
| pyrrolidin-1-yl | —CH₂— | CH | B(OH)₂ | I | —NHAc | 9 |
| piperidin-1-yl | —CH₂— | CH | B(OH)₂ | I | —NHAc | 10 |
| FCH₂CH₂CH₂— | —NHCH₂—* | CH | B(OH)₂ | I | —NHAc | 11 |
| NCCH₂CH₂— | —NHCH₂—* | CH | B(OH)₂ | I | —NHAc | 12 |
| H₃C-NH-C(=N-CN)-NH— | —CH₂— | CH | B(OH)₂ | I | —NHAc | 13 |
| H₂NC(O)CH₂— | —NHCH₂—* | CH | B(OH)₂ | I | 1H-1,2,3-triazol-1-yl | 14 |
| FCH₂CH(OH)CH₂— | —NHCH₂—* | CH | B(OH)₂ | I | —NHAc | 15 |
| FCH₂CH₂CH₂— | —NHCH₂—* | CH | B(OH)₂ | I | 1H-1,2,3-triazol-1-yl | 16 |
| CH₃CH₂— | —SO₂NHCH₂—* | CH | B(OH)₂ | I | —NHAc | 17 |
| CH₃— | —NHSO₂CH₂—* | CH | B(OH)₂ | I | —NHAc | 18 |
| 1H-imidazol-1-yl | —(CH₂)₃NHC(O)NH—* | CH | B(OH)₂ | I | —NHAc | 19 |
| 1H-1,2,3-triazol-5-yl | —SCH₂CH₂NHCH₂—* | CH | B(OH)₂ | I | —NHAc | 20 |
| pyridin-4-yl | —CH₂SO₂— | CH | B(OH)₂ | I | —NHAc | 21 |
| pyridin-2-yl | —CH₂NHSO₂—* | CH | B(OH)₂ | I | —NHAc | 22 |

TABLE 2-continued

| M | L | Y | Q | Z | R³ | Product |
|---|---|---|---|---|---|---|
| 1-methylimidazol-4-yl | —SO₂NHCH₂—* | CH | B(OH)₂ | I | —NHAc | 23 |
| 1,2,4-triazol-4-yl | —NHCH—* | CH | B(OH)₂ | I | —NHAc | 24 |
| 1H-1,2,3-triazol-5-yl | —S(O)CH₂— | CH | B(OH)₂ | I | —NHAc | 25 |
| H₂NC(O)CH₂— | —NHCH₂—* | CH | B(OH)₂ | I | —NHAc | 26 |
| H₂NCH₂C(O)— | —NHCH₂—* | CH | B(OH)₂ | I | —NHAc | 27 |
| CH₃— | —SO₂NHCH₂—* | CH | B(OH)₂ | I | —NHAc | 28 |
| CH₃— | —SO₂NHCH₂—* | CF | B(OH)₂ | I | —NHAc | 29 |
| 2H-tetrazol-2-yl | —CH₂— | CH | B(OH)₂ | I | —NHAc | 30 |
| pyridin-4-yl | —CH₂S(O)CH₂— | CH | B(OH)₂ | I | —NHAc | 31 |
| 1H-tetrazol-1-yl | —CH₂— | N | B(OH)₂ | I | —NHAc | 32 |
| 1H-1,2,3-triazol-1-yl | —CH₂— | N | B(OH)₂ | I | —NHAc | 33 |
| 1,3,4-thiadiazol-2-yl | —S(O)CH₂— | CH | B(OH)₂ | I | —NHAc | 34 |
| 1H-1,2,4-triazol-1-yl | —CH₂— | CH | B(OH)₂ | I | —NHAc | 35 |
| 5-methyl-1H-tetrazol-1-yl | —CH₂— | CH | B(OH)₂ | I | —NHAc | 36 |
| 5-methyl-2H-tetrazol-2-yl | —CH₂— | CH | B(OH)₂ | I | —NHAc | 37 |
| 1H-1,2,3-triazol-1-yl | —CH₂CH(OH)— | CH | B(OH)₂ | I | —NHAc | 38 |
| CH₃— | —SCH₂CH₂NHCH₂—* | CH | B(OH)₂ | I | —NHAc | 39 |

TABLE 2-continued

| M | L | Y | Q | Z | R³ | Product |
|---|---|---|---|---|----|---------|
| 1,2,4-triazol-1-yl | —CH₂— | N | B(OH)₂ | I | —NHAc | 40 |
| NCCH₂— | —N(Ac)—CH₂— | CH | B(OH)₂ | I | —NHAc | 41 |
| pyrazol-1-yl | —CH₂— | N | B(OH)₂ | I | —NHAc | 42 |
| 5-chloro-tetrazol-1-yl | —CH₂— | CH | B(OH)₂ | I | —NHAc | 43 |
| imidazol-1-yl | —CH₂— | CH | B(OH)₂ | I | 1,2,3-triazol-1-yl | 44 |
| HC≡CCH₂— | —NHCH₂—* | CH | B(OH)₂ | I | —NHAc | 45 |
| H₂C=CHCH₂— | —NHCH₂—* | CH | B(OH)₂ | I | —NHAc | 46 |
| H₂C=CHCH₂CH₂— | —NHCH₂—* | CH | B(OH)₂ | I | —NHAc | 47 |
| HC≡CCH₂CH₂— | —NHCH₂—* | CH | B(OH)₂ | I | —NHAc | 48 |
| HC≡C(CH₂)₃— | —NHCH₂—* | CH | B(OH)₂ | I | —NHAc | 49 |
| CH₃C≡CCH₂— | —NHCH₂—* | CH | B(OH)₂ | I | —NHAc | 50 |
| 3-fluoropiperidin-1-yl | —CH₂— | CH | B(OH)₂ | I | —NHAc | 51 |
| 1H-1,2,3-triazol-5-yl | —(CH₂)₃NHCH₂—* | CH | B(OH)₂ | I | —NHAc | 52 |
| F₂HCCH₂— | —NHCH₂—* | CH | B(OH)₂ | I | —NHAc | 53 |
| HC≡CCH₂— | —NHCH₂—* | CH | B(OH)₂ | I | 1,2,3-triazol-1-yl | 54 |
| isoxazolidin-2-yl | —CH₂— | CH | B(OH)₂ | I | —NHAc | 55 |
| NC— | (bond) | N | B(OH)₂ | I | —NHAc | 56 |
| HC≡C—CH(CH₃)— | —NHCH₂—* | CH | B(OH)₂ | I | —NHAc | 57 |
| 1H-1,2,3-triazol-5-yl | —CH₂NHCH₂—* | N | B(OH)₂ | I | —NHAc | 58 |

TABLE 2-continued

| M | L | Y | Q | Z | R³ | Product |
|---|---|---|---|---|----|---------|
| 1-methyl-tetrazol-5-yl | —CH₂NHCH₂—* | CH | B(OH)₂ | I | —NHAc | 59 |
| 2-methyl-tetrazol-5-yl | —CH₂NHCH₂—* | CH | B(OH)₂ | I | —NHAc | 60 |
| HC≡CFCH₂— | —NHCH₂—* | CH | B(OH)₂ | I | —NHAc | 61 |
| FH₂CCHFCH₂— | —NHCH₂—* | CH | B(OH)₂ | I | —NHAc | 62 |
| 1H-imidazol-5-yl | —CH₂CH₂NHC(O)—* | N | B(OH)₂ | I | —NHAc | 63 |
| 1,2,4-oxadiazol-3-yl | —CH₂NHC(O)—* | CH | B(OH)₂ | I | —NHAc | 64 |
| 1,3,4-thiadiazol-2-yl | —CH₂NHC(O)—* | CH | B(OH)₂ | I | —NHAc | 65 |
| H₂NCH₂C(O)— | —NH—CH(CH₃)—* | CH | B(OH)₂ | I | —NHAc | 66 |
| H₂NC(O)CH₂— | —NH—CH(CH₃)—* | CH | B(OH)₂ | I | —NHAc | 67 |
| pyridin-4-yl | —CH₂S— | CH | B(OH)₂ | I | —NHAc | 68 |
| pyridin-4-yl | —CH₂NHSO₂—* | CH | B(OH)₂ | I | —NHAc | 69 |
| FCH₂CH₂CH₂— | —NHCH₂CH(OH)—* | CH | B(OH)₂ | I | —NHAc | 70 |
| 5-oxo-1,2,4-oxadiazol-3-yl | —CH₂— | CH | B(OH)₂ | I | —NHAc | 71 |
| 5-methyl-1,2,4-oxadiazol-3-yl | —CH₂— | CH | B(OH)₂ | I | —NHAc | 72 |
| 2-(((tetrahydrofuran-2-yl)methyl)amino)thiazol-4-yl | —CH₂— | CH | B(OH)₂ | I | —NHAc | 73 |

TABLE 2-continued

| M | L | Y | Q | Z | R³ | Product |
|---|---|---|---|---|----|---------|
| [thiazole-NH-CH2-(3-methoxyphenyl)] | —CH₂— | CH | B(OH)₂ | I | —NHAc | 74 |
| [imidazol-1-yl] | —CH₂—CH(NH₂)—  * | CH | B(OH)₂ | I | —NHAc | 75 |
| [tetrazol-1-yl] | —CH₂— | CH | B(OH)₂ | I | —NH₂ | 76 |
| [4-formylpiperazin-1-yl] | —CH₂CH(OH)— | CH | B(OH)₂ | I | —NHAc | 77 |
| [4-formylpiperazin-1-yl] | —CH(CH₂OH)— | CH | B(OH)₂ | I | —NHAc | 78 |
| [imidazol-1-yl] | —CH₂CH(OH)— | CH | B(OH)₂ | I | —NHAc | 79 |
| FCH₂CH₂CH₂— | —NHCH₂—* | CH | B(OH)₂ | I | —NHC(O)CHF₂ | 80 |
| HC≡CCH₂— | —NHCH₂—* | CH | B(OH)₂ | I | —NHC(O)CHF₂ | 81 |

Compounds containing L groups having free amines (e.g., compounds derived from the reagents having L groups marked with * in Table 2) alternatively may be synthesized from the corresponding protected amine (e.g., —CH₂N(BOC)CH₂— or —N(BOC)CH₂—) followed by amine deprotection.

Alternatively, the exemplary compounds in Table 1 can be synthesized by the process depicted in Scheme B using, for example, the aryl boronic acids and aryl iodides listed in Table 3, below.

Scheme B

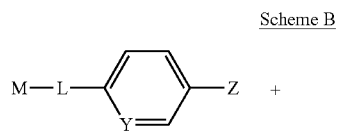
+
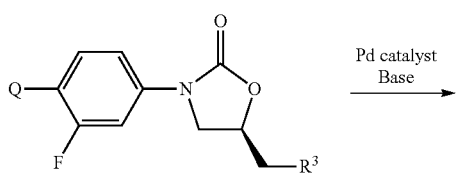
Pd catalyst, Base →
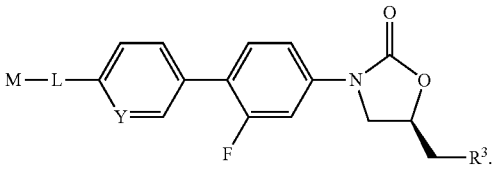

TABLE 3

| M | L | Y | Z | Q | R³ | Product |
|---|---|---|---|---|----|---------|
| quinolin-4-yl | —CH₂NHCH₂—* | CH | I | B(OH)₂ | —NHAc | 1 |
| 1,2,3-thiadiazol-4-yl | —CH₂NHCH₂—* | CH | I | B(OH)₂ | —NHAc | 2 |
| tetrazol-1-yl | —CH₂— | CH | I | B(OH)₂ | —NHAc | 3 |
| 1,2,3-triazol-1-yl | —CH₂— | CH | I | B(OH)₂ | —NHAc | 4 |
| isoxazol-4-yl | —CH₂NHCH₂—* | CH | I | B(OH)₂ | —NHAc | 5 |
| 2H-1,2,3-triazol-4-yl | —CH₂NHCH₂—* | CH | I | B(OH)₂ | —NHAc | 6 |
| 2H-1,2,3-triazol-4-yl | —CH₂NHCH₂—* | CH | I | B(OH)₂ | 1,2,3-triazol-1-yl | 7 |
| 2H-1,2,3-triazol-4-yl | —CH₂N(CH₃)CH₂— | CH | I | B(OH)₂ | —NHAc | 8 |
| pyrrolidin-1-yl | —CH₂— | CH | I | B(OH)₂ | —NHAc | 9 |
| piperidin-1-yl | —CH₂— | CH | I | B(OH)₂ | —NHAc | 10 |
| FCH₂CH₂CH₂— | —NHCH₂—* | CH | I | B(OH)₂ | —NHAc | 11 |
| NCCH₂CH₂— | —NHCH₂—* | CH | I | B(OH)₂ | —NHAc | 12 |
| N-cyano-N'-methylguanidinyl | —CH₂— | CH | I | B(OH)₂ | —NHAc | 13 |
| H₂NC(O)CH₂— | —NHCH₂—* | CH | I | B(OH)₂ | 1,2,3-triazol-1-yl | 14 |
| FCH₂CH(OH)CH₂— | —NHCH₂—* | CH | I | B(OH)₂ | —NHAc | 15 |

TABLE 3-continued

| M | L | Y | Z | Q | R³ | Product |
|---|---|---|---|---|---|---|
| FCH₂CH₂CH₂— | —NHCH₂—* | CH | I | B(OH)₂ | 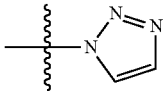 [SMILES: *n1ccnn1] | 16 |
| CH₃CH₂— | —SO₂NHCH₂—* | CH | I | B(OH)₂ | —NHAc | 17 |
| CH₃— | —NHSO₂CH₂— | CH | I | B(OH)₂ | —NHAc | 18 |
| 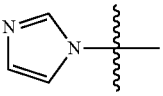 [SMILES: *n1ccnc1] | —(CH₂)₃NHC(O)NH—* | CH | I | B(OH)₂ | —NHAc | 19 |
| 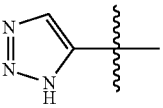 | —SCH₂CH₂NHCH₂—* | CH | I | B(OH)₂ | —NHAc | 20 |
| 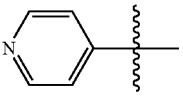 | —CH₂SO₂— | CH | I | B(OH)₂ | —NHAc | 21 |
| 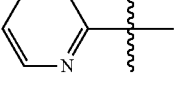 | —CH₂NHSO₂—* | CH | I | B(OH)₂ | —NHAc | 22 |
| 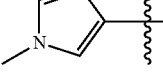 | —SO₂NHCH₂—* | CH | I | B(OH)₂ | —NHAc | 23 |
| 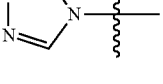 | —NHCH₂—* | CH | I | B(OH)₂ | —NHAc | 24 |
| 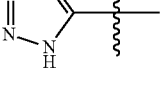 | —S(O)CH₂— | CH | I | B(OH)₂ | —NHAc | 25 |
| H₂NC(O)CH₂— | —NHCH₂—* | CH | I | B(OH)₂ | —NHAc | 26 |
| H₂NCH₂C(O)— | —NHCH₂—* | CH | I | B(OH)₂ | —NHAc | 27 |
| CH₃— | —SO₂NHCH₂—* | CH | I | B(OH)₂ | —NHAc | 28 |
| CH₃— | —SO₂NHCH₂—* | CF | I | B(OH)₂ | —NHAc | 29 |
| 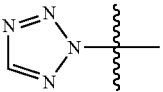 [SMILES: *n1ncnn1] | —CH₂— | CH | I | B(OH)₂ | —NHAc | 30 |
| 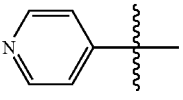 | —CH₂S(O)CH₂— | CH | I | B(OH)₂ | —NHAc | 31 |
| 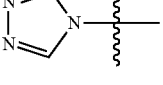 | —CH₂— | N | I | B(OH)₂ | —NHAc | 32 |
| 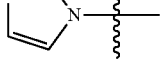 | —CH₂— | N | I | B(OH)₂ | —NHAc | 33 |

TABLE 3-continued

| M | L | Y | Z | Q | R³ | Product |
|---|---|---|---|---|---|---|
| 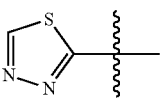 [SMILES: *c1nncs1] | —S(O)CH₂— | CH | I | B(OH)₂ | —NHAc | 34 |
| 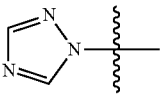 | —CH₂— | CH | I | B(OH)₂ | —NHAc | 35 |
| 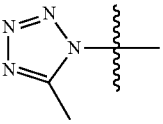 [SMILES: *n1nnnc1C] | —CH₂— | CH | I | B(OH)₂ | —NHAc | 36 |
| 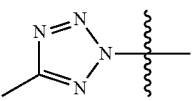 | —CH₂— | CH | I | B(OH)₂ | —NHAc | 37 |
| 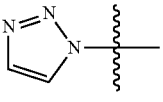 | —CH₂CH(OH)— | CH | I | B(OH)₂ | —NHAc | 38 |
| CH₃— | —SCH₂CH₂NHCH₂—* | CH | I | B(OH)₂ | —NHAc | 39 |
| 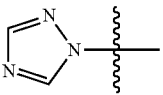 [SMILES: *n1cncn1] | —CH₂— | N | I | B(OH)₂ | —NHAc | 40 |
| NCCH₂— | —N(Ac)—CH₂— | CH | I | B(OH)₂ | —NHAc | 41 |
| 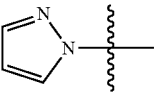 | —CH₂— | N | I | B(OH)₂ | —NHAc | 42 |
| 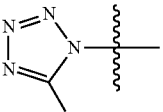 | —CH₂— | CH | I | B(OH)₂ | —NHAc | 43 |
| 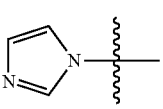 [SMILES: *n1ccnc1] | —CH₂— | CH | I | B(OH)₂ | 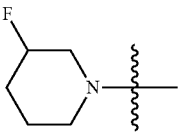 | 44 |
| HC≡CCH₂— | —NHCH₂—* | CH | I | B(OH)₂ | —NHAc | 45 |
| H₂C=CHCH₂— | —NHCH₂—* | CH | I | B(OH)₂ | —NHAc | 46 |
| H₂C=CHCH₂CH₂— | —NHCH₂—* | CH | I | B(OH)₂ | —NHAc | 47 |
| HC≡CCH₂CH₂— | —NHCH₂—* | CH | I | B(OH)₂ | —NHAc | 48 |
| HC≡C(CH₂)₃— | —NHCH₂—* | CH | I | B(OH)₂ | —NHAc | 49 |
| CH₃C≡CCH₂— | —NHCH₂—* | CH | I | B(OH)₂ | —NHAc | 50 |
| 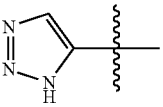 | —CH₂— | CH | I | B(OH)₂ | —NHAc | 51 |
|  | —(CH₂)₃NHCH₂—* | CH | I | B(OH)₂ | —NHAc | 52 |

TABLE 3-continued

| M | L | Y | Z | Q | R³ | Product |
|---|---|---|---|---|----|---------|
| F₂HCCH₂— | —NHCH₂—* | CH | I | B(OH)₂ | —NHAc | 53 |
| HC≡CCH₂— | —NHCH₂—* | CH | I | B(OH)₂ | 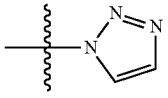 | 54 |
| 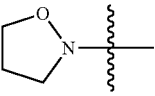 | —CH₂— | CH | I | B(OH)₂ | —NHAc | 55 |
| NC— | (bond) | N | I | B(OH)₂ | —NHAc | 56 |
| 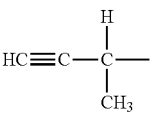 | —NHCH₂—* | CH | I | B(OH)₂ | —NHAc | 57 |
| 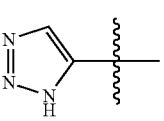 | —CH₂NHCH₂—* | N | I | B(OH)₂ | —NHAc | 58 |
| 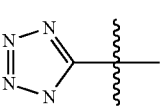 | —CH₂NHCH₂—* | CH | I | B(OH)₂ | —NHAc | 59 |
| 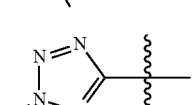 | —CH₂NHCH₂—* | CH | I | B(OH)₂ | —NHAc | 60 |
| HC=CFCH₂— | —NHCH₂—* | CH | I | B(OH)₂ | —NHAc | 61 |
| FH₂CCHFCH₂— | —NHCH₂—* | CH | I | B(OH)₂ | —NHAc | 62 |
| 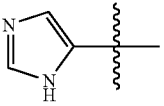 | —CH₂CH₂NHC(O)—* | N | I | B(OH)₂ | —NHAc | 63 |
| 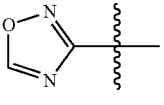 | —CH₂NHC(O)—* | CH | I | B(OH)₂ | —NHAc | 64 |
| 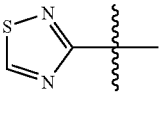 | —CH₂NHC(O)—* | CH | I | B(OH)₂ | —NHAc | 65 |
| H₂NCH₂C(O)— | 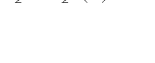 | CH | I | B(OH)₂ | —NHAc | 66 |
| H₂NC(O)CH₂— | 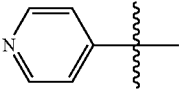 | CH | I | B(OH)₂ | —NHAc | 67 |
| 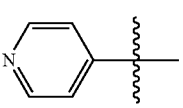 | —CH₂S— | CH | I | B(OH)₂ | —NHAc | 68 |
|  | —CH₂NHSO₂—* | CH | I | B(OH)₂ | —NHAc | 69 |

TABLE 3-continued

| M | L | Y | Z | Q | R³ | Product |
|---|---|---|---|---|-----|---------|
| FCH₂CH₂CH₂— | —NHCH₂CH(OH)—* | CH | I | B(OH)₂ | —NHAc | 70 |
| 3-(1,2,4-oxadiazol-5(4H)-on-3-yl) group | —CH₂— | CH | I | B(OH)₂ | —NHAc | 71 |
| 5-methyl-1,2,4-oxadiazol-3-yl group | —CH₂— | CH | I | B(OH)₂ | —NHAc | 72 |
| 2-((tetrahydrofuran-2-ylmethyl)amino)thiazol-4-yl group | —CH₂— | CH | I | B(OH)₂ | —NHAc | 73 |
| 2-((3-methoxybenzyl)amino)thiazol-4-yl group | —CH₂— | CH | I | B(OH)₂ | —NHAc | 74 |
| 1H-imidazol-1-yl group | —CH₂—CH(NH₂)—* | CH | I | B(OH)₂ | —NHAc | 75 |
| 1H-tetrazol-1-yl group | —CH₂— | CH | I | B(OH)₂ | —NH₂ | 76 |
| 4-formylpiperazin-1-yl group | —CH₂CH(OH)— | CH | I | B(OH)₂ | —NHAc | 77 |
| 4-formylpiperazin-1-yl group | —CH(CH₂OH)— | CH | I | B(OH)₂ | —NHAc | 78 |
| 1H-imidazol-1-yl group | —CH₂CH(OH)— | CH | I | B(OH)₂ | —NHAc | 79 |
| FCH₂CH₂CH₂— | —NHCH₂—* | CH | I | B(OH)₂ | —NHC(O)CHF₂ | 80 |
| HC≡CCH₂— | —NHCH₂—* | CH | I | B(OH)₂ | —NHC(O)CHF₂ | 81 |

As discussed above, compounds containing L groups having free amines (e.g., compounds derived from the reagents having L groups marked with * in Table 3) alternatively may be synthesized from the corresponding protected amine (e.g., —CH₂N(BOC)CH₂— or —N(BOC)CH₂—) followed by amine deprotection.

In addition to the reagents listed in Tables 2 and 3, reagents containing other Q groups (e.g., boronic esters, boronic halides, or organoboranes) and/or reagents containing other Z groups (e.g., other halogens or sulfonates) may be used to synthesize the exemplary compounds in Table 1 according to the processes of the invention.

3. EXAMPLES

Embodiments of the present invention are described in the following examples, which are meant to illustrate, not to limit, the scope and nature of the invention.

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Example 1

Scheme 1 depicts the synthesis of compound 11 from aryl iodide 108 and aryl boronic acid 120.

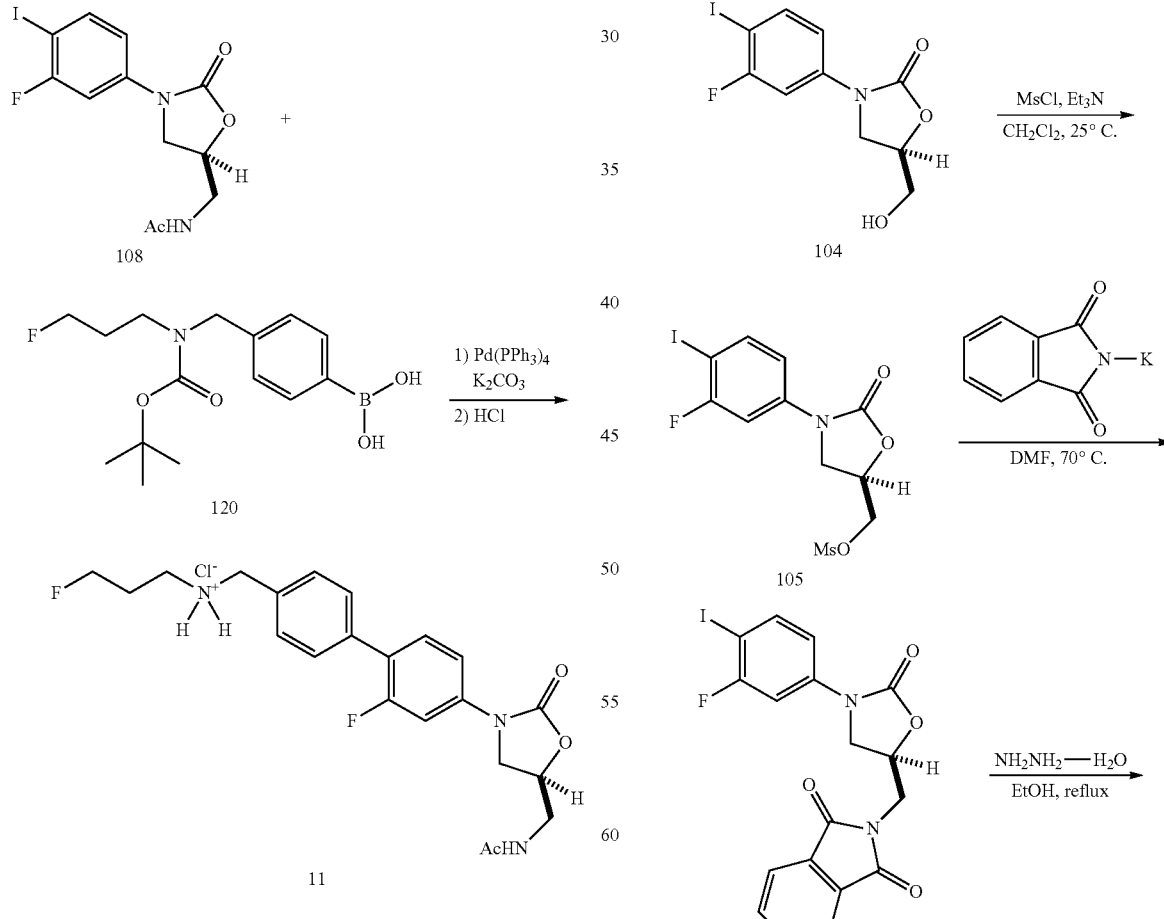

a. Synthesis of Aryl Iodide 108—Method A

Scheme 2 depicts the synthesis of aryl iodide 108 from 3-fluoroanaline 101.

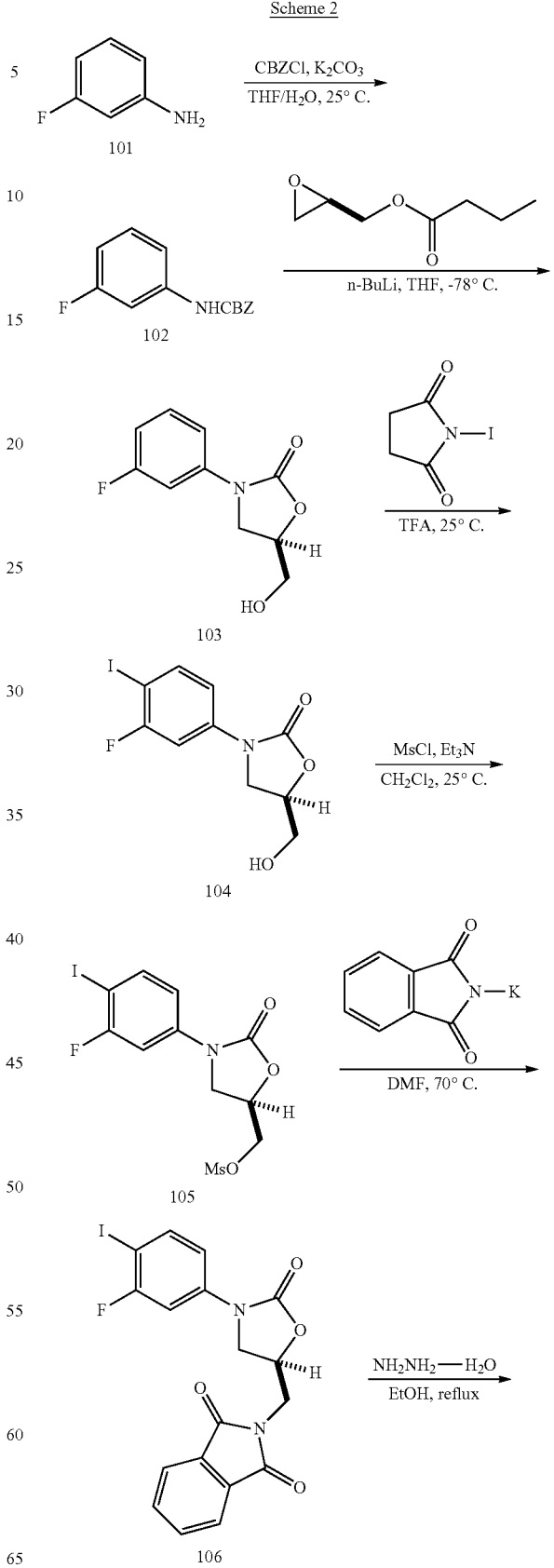

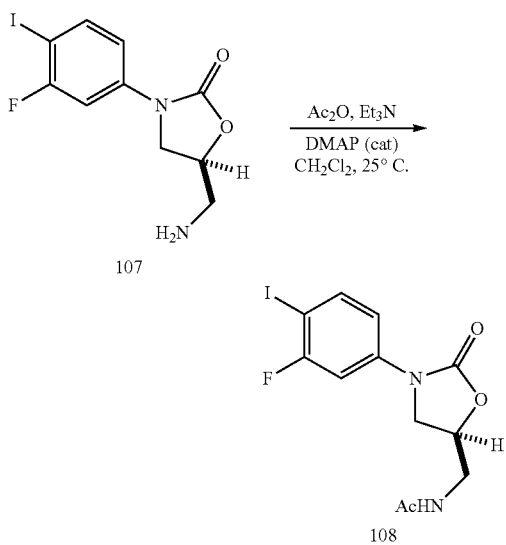

A solution of 3-fluoroanaline 101 (18.7 g, 168.3 mmol) in tetrahydrofuran (THF, 150 mL) was treated with potassium carbonate ($K_2CO_3$, 46.45 g, 336.6 mmol, 2.0 equiv) and $H_2O$ (150 mL) before a solution of benzyl chloroformate (CBZCl, 31.58 g, 185.1 mmol, 26.1 mL, 1.1 equiv) in THF (50 mL) was dropwise added into the reaction mixture at room temperature under $N_2$. The resulting reaction mixture was stirred at room temperature for 2 h. When TLC showed the reaction was complete, the reaction mixture was treated with $H_2O$ (100 mL) and ethyl acetate (EtOAc, 100 mL). The two layers were separated, and the aqueous layer was extracted with EtOAc (2×100 mL). The combined organic extracts were washed with $H_2O$ (2×100 mL) and saturated aqueous sodium chloride (NaCl, 100 mL), dried over magnesium sulfate ($MgSO_4$), and concentrated in vacuo. The residue was further dried in vacuo to afford the desired (3-fluoro-phenyl)-carbamic acid benzyl ester 102 (39.2 g, 95% yield) as pale-yellow oil. This product was directly used in subsequent reactions without further purification. $^1$H NMR (300 MHz, $CDCl_3$) δ 5.23 (s, 2H, $OCH_2Ph$), 6.75-6.82 (m, 2H), 7.05 (dd, 1H, J=1.4, 8.2 Hz), 7.22-7.45 (m, 6H). $C_{14}H_{12}FNO_2$, LCMS (EI) m/e 246 ($M^++H$).

A solution of amine 102 (39.2 g, 160.0 mmol) in anhydrous THF (300 mL) was cooled to −78° C. in a dry-ice/acetone bath before a solution of n-butyl lithium (n-BuLi, 2.5 M solution in hexane, 70.4 mL, 176 mmol, 1.1 equiv) was dropwise added under $N_2$. The resulting reaction mixture was subsequently stirred at −78° C. for 1 h before a solution of (R)-(−)-glycidyl butyrate (25.37 g, 24.6 mL, 176 mmol, 1.1 equiv) in anhydrous THF (100 mL) was dropwise added into the reaction mixture at −78° C. under $N_2$. The resulting reaction mixture was stirred at −78° C. for 30 min before being gradually warmed to room temperature for 12 h under $N_2$. When TLC and HPLC/MS showed the reaction was complete, the reaction mixture was quenched with $H_2O$ (200 mL), and the resulting mixture was stirred at room temperature for 1 h before EtOAc (200 mL) was added. The two layers were separated, and the aqueous layer was extracted with EtOAc (2×100 mL). The combined organic extracts were washed with $H_2O$ (2×100 mL) and saturated aqueous NaCl (100 mL), dried over $MgSO_4$, and concentrated in vacuo. White crystals precipitated from the concentrated solution when most of the solvent was evaporated. The residue was then treated with 20% EtOAc/hexane (100 mL) and the resulting slurry was stirred at room temperature for 30 min. The solids were collected by filtration and washed with 20% EtOAc/hexane (2×50 mL) to afford the desired (5R)-(3-(3-fluoro-phenyl)-5-hydroxymethyl-oxazolidin-2-one 103 (24.4 g, 72.3% yield) as white crystals. This product was directly used in subsequent reactions without further purification. $^1$H NMR (300 MHz, DMSO-$d_6$) δ 3.34-3.72 (m, 2H), 3.83 (dd, 1H, J=6.2, 9.0 Hz), 4.09 (t, 1H, J=12.0 Hz), 4.68-4.75 (m, 1H), 5.23 (t, 1H, J=5.6 Hz, OH), 6.96 (m, 1H), 7.32-7.56 (m, 3H). $C_{10}H_{10}FNO_3$, LCMS (EI) m/e 212 ($M^++H$).

A solution of alcohol 103 (10.74 g, 50.9 mmol) in trifluoroacetic acid (TFA, 50 mL) was treated with N-iodosuccinimide (12.03 g, 53.45 mmol, 1.05 equiv) at 25° C. and stirred for 2 h. When TLC and HPLC/MS showed the reaction was complete, the reaction mixture was concentrated in vacuo. The residue was then treated with $H_2O$ (100 mL) and 20% EtOAc/hexane (100 mL) at 25° C., and the resulting mixture was stirred at 25° C. for 30 min before being cooled to 0-5° C. for 2 h. The white solids were collected by filtration, washed with $H_2O$ (2×25 mL) and 20% EtOAc/hexane (2×25 mL), and dried in vacuo to afford the desired (5R)-3-(3-fluoro-4-iodo-phenyl)-5-hydroxymethyl-oxazolidin-2-one 104 (15.1 g, 88% yield) as an off-white powder. This product was directly used in subsequent reactions without further purification. $^1$H NMR (300 MHz, DMSO-$d_6$) δ 3.58 (dd, 1H, J=4.2, 12.6 Hz), 3.67 (dd, 1H, J=3.0, 12.6 Hz), 3.67 (dd, 1H, J=6.3, 9.0 Hz), 4.07 (t, 1H, J=9.0 Hz), 4.72 (m, 1H), 5.21 (br. s, 1H, OH), 7.22 (dd, 1H, J=2.4, 8.4 Hz), 7.58 (dd, 1H, J=2.4, 11.1 Hz), 7.81 (dd, 1H, J=7.8, 8.7 Hz). $C_{10}H_9FINO_3$, LCMS (EI) m/e 338 ($M^++H$).

A solution of iodo-alcohol 104 (25.2 g, 74.8 mmol) in methylene chloride ($CH_2Cl_2$, 150 mL) was treated with triethylamine (TEA, 15.15 g, 20.9 mL, 150 mmol, 2.0 equiv) at 25° C., and the resulting mixture was cooled to 0-5° C. before methanesulfonyl chloride (MsCl, 10.28 g, 6.95 mL, 89.7 mmol, 1.2 equiv) was dropwise introduced into the reaction mixture at 0-5° C. under $N_2$. The resulting reaction mixture was subsequently stirred at 0-5° C. for 1 h under $N_2$. When TLC and HPLC/MS showed the reaction was complete, the reaction mixture was quenched with $H_2O$ (100 mL) and $CH_2Cl_2$ (100 mL). The two layers were separated, and the aqueous layer was extracted with $CH_2Cl_2$ (100 mL). The combined organic extracts were washed with $H_2O$ (2×100 mL) and saturated aqueous NaCl (100 mL), dried over $MgSO_4$, and concentrated in vacuo. The residue was further dried in vacuo to afford the desired (5R)-methanesulfonic acid 3-(3-fluoro-4-iodo-phenyl)-2-oxo-oxazolidin-5-ylmethyl ester 105 (30.71 g, 98.9% yield) as an off-white powder. This product was directly used in subsequent reactions without further purification. $C_{11}H_{11}FINO_5S$, LCMS (EI) m/e 416 ($M^++H$).

A solution of mesylate 105 (26.38 g, 63.57 mmol) in anhydrous N,N-dimethylformamide (DMF, 120 mL) was treated with solid potassium phthalimide (12.95 g, 70.0 mmol, 1.1 equiv) at 25° C., and the resulting reaction mixture was warmed to 70° C. for 2 h. When TLC and HPLC showed the reaction was complete, the reaction mixture was cooled to room temperature before being quenched with $H_2O$ (400 mL). The resulting mixture was stirred at room temperature for 10 min before being cooled to 0-5° C. for 1 h. The white precipitate was collected by filtration, washed with water (3×100 mL), and dried in vacuo to afford the desired (5R)-2-[3-(3-fluoro-4-iodo-phenyl)-2-oxo-oxazolidin-5-ylmethyl]- isoindole-1,3-dione 106 (27.85 g, 94%) as an off-white powder. This product was directly used in subsequent reactions without further purification. $C_{18}H_{12}FIN_2O_4$, LCMS (EI) m/e 467 ($M^+$+H).

A solution of phthalimide 106 (23.3 g, 50.0 mmol) in ethanol (EtOH, 150 mL) was treated with hydrazine monohydrate (12.52 g, 12.1 mL, 250 mmol, 5.0 equiv) at 25° C., and the resulting reaction mixture was warmed to reflux for 2 h. A white precipitate formed as the reaction mixture refluxed. When TLC and HPLC showed that the reaction was complete, the reaction mixture was cooled to room temperature before being quenched with $H_2O$ (100 mL). The aqueous solution was then extracted with $CH_2Cl_2$ (3×200 mL), and the combined organic extracts were washed with $H_2O$ (2×100 mL) and saturated aqueous NaCl (100 mL), dried over $MgSO_4$, and concentrated in vacuo. The residue was further dried in vacuo to afford the desired (5S)-5-aminomethyl-3-(3-fluoro-4-iodo-phenyl)-oxazolidin-2-one 107 (16.0 g, 95.2% yield) as a white powder. This product was directly used in the subsequent reactions without further purification. $C_{10}H_{10}FIN_2O_2$, LCMS (EI) m/e 337 ($M^+$+H).

A suspension of amine 107 (16.0 g, 47.6 mmol) in $CH_2Cl_2$ (150 mL) was treated with TEA (9.62 g, 13.2 mL, 95.2 mmol, 2.0 equiv) at 25° C., and the resulting reaction mixture was cooled to 0-5° C. before being treated with acetic anhydride ($Ac_2O$, 7.29 g, 6.75 mL, 71.4 mmol, 1.5 equiv) and 4-N,N-dimethylaminopyridine (DMAP, 58 mg, 0.5 mmol, 0.01 equiv) at 0-5° C. under $N_2$. The resulting reaction mixture was subsequently stirred at 0-5° C. for 2 h. When TLC and HPLC showed the reaction was complete, the reaction mixture was quenched with $H_2O$ (100 mL). The two layers were separated, and the aqueous layer was extracted with $CH_2Cl_2$ (2×50 mL). The combined organic extracts were washed with $H_2O$ (2×100 mL) and saturated aqueous NaCl (100 mL), dried over $MgSO_4$, and concentrated in vacuo. The residue was further dried in vacuo to afford the desired (5S)—N-[3-(3-fluoro-4-iodo-phenyl)-2-oxo-oxazolidin-5-ylmethyl]-acetamide 108 (17.36 g, 96.5% yield) as a white powder. This product was directly used in subsequent reactions without further purification. $^1H$ NMR (300 MHz, DMSO-$d_6$) δ 1.63 (s, 3H, NHCOCH$_3$), 3.25 (t, 2H, J=5.4 Hz), 3.56 (dd, 1H, J=6.4, 9.2 Hz), 3.95 (t, 1H, J=9.1 Hz), 4.58 (m, 1H), 5.16 (t, 1H, J=5.7 Hz, OH), 7.02 (dd, 1H, J=2.4, 8.2 Hz), 7.38 (dd, 1H, J=2.4, 10.8 Hz), 7.66 (t, 1H, J=7.5, 8.4 Hz), 8.08 (t, 1H, J=5.8 Hz, NHCOCH$_3$). $C_{12}H_{12}FIN_2O_3$, LCMS (EI) m/e 379 ($M^+$+H).

b. Synthesis of Aryl Iodide 108—Method B

Scheme 3 depicts an alternate synthesis of aryl iodide 108 from alcohol 103.

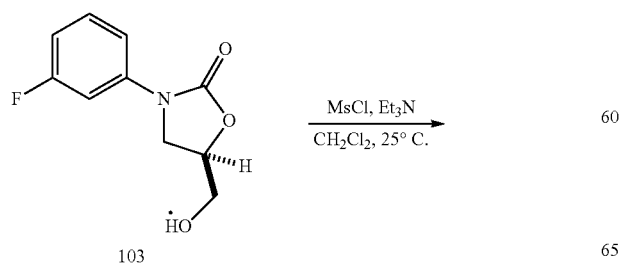

Scheme 3

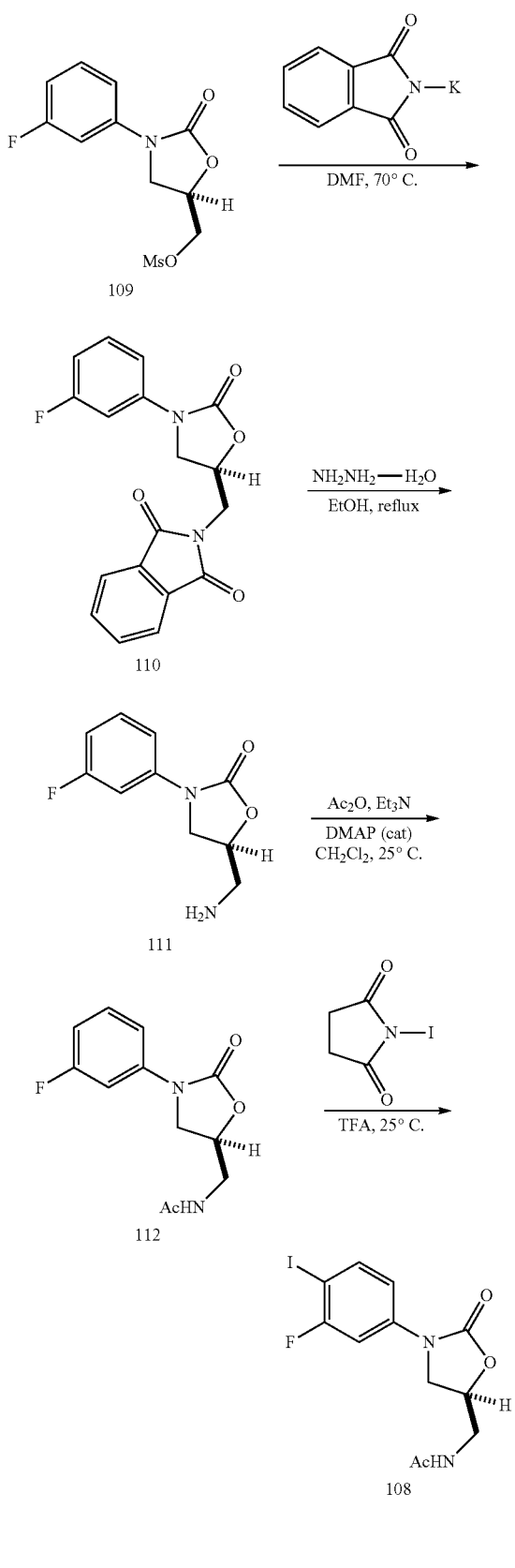

A solution of alcohol 103 (6.33 g, 30.0 mmol) in $CH_2Cl_2$ (60 mL) was treated with TEA (6.07 g, 8.36 mL, 60 mmol, 2.0 equiv) at 25° C., and the resulting mixture was cooled to 0-5° C. before MsCl (3.78 g, 2.55 mL, 33.0 mmol, 1.1 equiv) was dropwise introduced into the reaction mixture at 0-5° C. under N2. The resulting reaction mixture was subsequently stirred at 0-5° C. for 1 h under $N_2$. When TLC and HPLC/MS showed the reaction was complete, the reaction mixture was quenched with $H_2O$ (40 mL) and $CH_2Cl_2$ (40 mL). The two layers were separated, and the aqueous layer was extracted with $CH_2Cl_2$ (40 mL). The combined organic extracts were washed with $H_2O$ (2×40 mL) and saturated aqueous NaCl (40 mL), dried over $MgSO_4$, and concentrated in vacuo. The residue was further dried in vacuo to afford the desired (5R)-methanesulfonic acid 3-(3-fluoro-phenyl)-2-oxo-oxazolidin-5-ylmethyl ester 109 (7.69 g, 88.7% yield) as an off-white powder. This product was directly used in subsequent reactions without further purification. $C_{11}H_{12}FNO_5S$, LCMS (EI) m/e 290 ($M^+$+H).

A solution of mesylate 109 (2.89 g, 10.0 mmol) in anhydrous DMF (20 mL) was treated with solid potassium phthalimide (2.22 g, 70.0 mmol, 1.2 equiv) at 25° C., and the resulting reaction mixture was warmed to 70° C. for 4 h. When TLC and HPLC showed the reaction was complete, the reaction mixture was cooled to room temperature before being quenched with $H_2O$ (60 mL). The resulting mixture was stirred at room temperature for 10 min before being cooled to 0-5° C. for 1 h. The white precipitate was collected by filtration, washed with water (2×40 mL), and dried in vacuo to afford the desired (5R)-2-[3-(3-fluoro-phenyl)-2-oxo-oxazolidin-5-ylmethyl]-isoindole-1,3-dione 110 (3.12 g, 91.8% yield) as an off-white powder. This product was directly used in subsequent reactions without further purification. $C_{18}H_{13}FN_2O_4$, LCMS (EI) m/e 341 ($M^+$+H).

A solution of phthalimide 110 (3.0 g, 8.82 mmol) in ethanol (EtOH, 30 mL) was treated with hydrazine monohydrate (2.20 g, 2.2 mL, 44.12 mmol, 5.0 equiv) at 25° C., and the resulting reaction mixture was warmed to reflux for 2 h. White precipitates formed as the reaction mixture was refluxed. When TLC and HPLC showed the reaction was complete, the reaction mixture was cooled to room temperature before being quenched with $H_2O$ (20 mL). The aqueous solution was then extracted with $CH_2Cl_2$ (3×40 mL), and the combined organic extracts were washed with $H_2O$ (2×20 mL) and saturated aqueous NaCl (20 mL), dried over $MgSO_4$, and concentrated in vacuo. The residue was further dried in vacuo to afford the desired (5S)-5-aminomethyl-3-(3-fluoro-phenyl)-oxazolidin-2-one 111 (1.79 g, 96.6% yield) as a white powder. This product was directly used in the subsequent reactions without further purification. $C_{10}H_{11}FN_2O_2$, LCMS (EI) m/e 211 ($M^+$+H).

A suspension of amine 111 (2.60 g, 12.38 mmol) in $CH_2Cl_2$ (40 mL) was treated with TEA (2.50 g, 3.4 mL, 24.76 mmol, 2.0 equiv) at 25° C., and the resulting reaction mixture was cooled to 0-5° C. before being treated with acetic anhydride ($Ac_2O$, 1.90 g, 1.75 mL, 18.75 mmol, 1.5 equiv) and DMAP (15 mg, 0.12 mmol, 0.01 equiv) at 0-5° C. under $N_2$. The resulting reaction mixture was subsequently stirred at 0-5° C. for 2 h. When TLC and HPLC showed the reaction was complete, the reaction mixture was quenched with $H_2O$ (20 mL). The two layers were separated, and the aqueous layer was then extracted with $CH_2Cl_2$ (2×20 mL). The combined organic extracts were washed with $H_2O$ (2×20 mL) and saturated aqueous NaCl (20 mL), dried over $MgSO_4$, and concentrated in vacuo. The residue was further dried in vacuo to afford the desired (5S)—N-[3-(3-fluoro-4-phenyl)-2-oxo-oxazolidin-5-ylmethyl]-acetamide 112 (2.93 g, 94% yield) as a white powder. This product was directly used in the subsequent reactions without further purification. $C_{12}H_{13}FN_2O_3$, LCMS (EI) m/e 253 ($M^+$+H).

A solution of acetamide 112 (2.3 g, 9.1 mmol) in TFA (20 mL) was treated with N-iodosuccinimide (2.3 g, 10.0 mmol, 1.1 equiv) at 25° C., and the resulting reaction mixture was stirred at 25° C. for 2 h. When TLC and HPLC/MS showed the reaction was complete, the reaction mixture was concentrated in vacuo. The residue was treated with $H_2O$ (20 mL) and 20% EtOAc/hexane (20 mL) at 25° C., and the resulting mixture was stirred at 25° C. for 30 min before being cooled to 0-5° C. for 2 h. The white solids were collected by filtration, washed with $H_2O$ (2×20 mL) and 20% EtOAc/hexane (2×20 mL), and dried in vacuo to afford the desired (5S)—N-[3-(3-fluoro-4-iodo-phenyl)-2-oxo-oxazolidin-5-ylmethyl]-acetamide 108 (3.34 g, 96.8% yield) as an off-white powder. This product was found to be identical with the material obtained from Method A and was directly used in subsequent reactions without further purification.

c. Synthesis of Aryl Boronic Acid 120

Scheme 4 depicts three synthetic routes to aryl boronic acid 115.

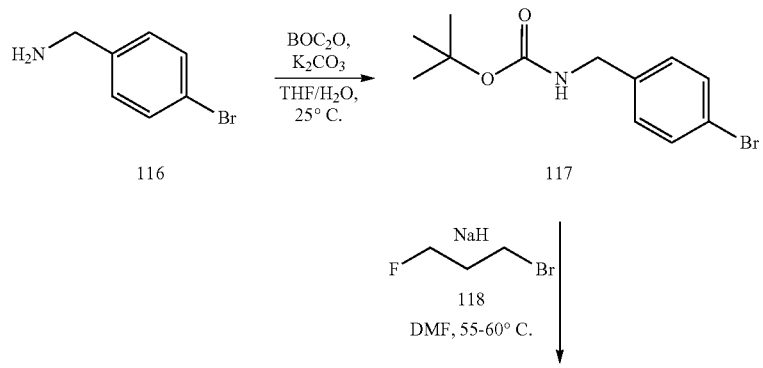

Scheme 4

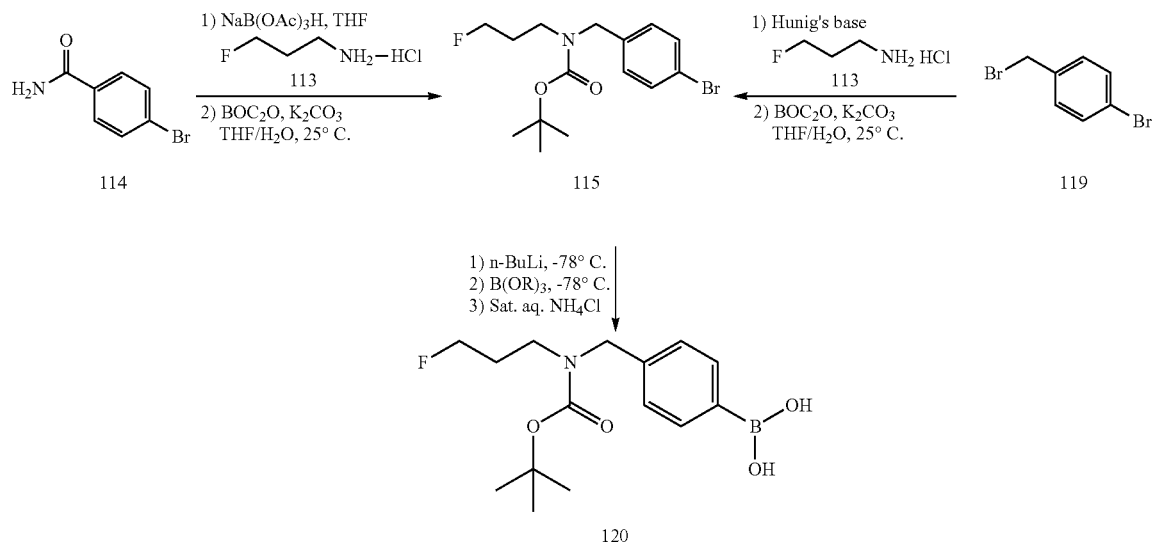

i. Synthesis of Amine 113

A solution of 3-fluoro-propan-1-ol (31.2 g, 400 mmol) in 300 mL of $CH_2Cl_2$ was treated with methanesulfonyl chloride (55 g, 38 mL, 480 mmol, 1.2 equiv) at 0° C. The resulting reaction mixture was gradually warmed to room temperature and stirred for 1-2 hours. When $^1H$ NMR showed the reaction was complete, the reaction mixture was treated with $H_2O$ (100 mL), and the two layers were separated. The aqueous layer was extracted with $CH_2Cl_2$ (2×100 mL). The combined organic layers were washed with $H_2O$ (3×100 mL) and dried over $MgSO_4$. The solvent was removed in vacuo to afford the desired methanesulfonic acid 3-fluoro-propyl ester (57.2 g, 91% yield) as a yellow oil.

A solution of methanesulfonic acid 3-fluoro-propyl ester (34.5 g, 221 mmol) in 250 mL of anhydrous DMF was treated with solid potassium phthalimide (49 g, 265 mmol, 1.2 equiv) at 25° C. The resulting suspension was warmed to 70-80° C. for 2 hours. When $^1H$ NMR showed that the reaction was complete, the reaction mixture was treated with $H_2O$ (200 mL). The aqueous solution was extracted with EtOAc (3×100 mL). The combined organic layers were washed with $H_2O$ (3×100 mL) and dried over $MgSO_4$. The solvent was removed in vacuo to afford the desired 2-(3-fluoro-propyl)-isoindole-1,3-dione (45.4 g, 45.5 g theoretical, 99.7% yield) as a white powder.

A suspension of 2-(3-fluoro-propyl)-isoindole-1,3-dione (45.4 g, 221 mmol) in 400 mL of 95% aqueous ethanol was treated with hydrazine monohydrate (11.3 g, 11.1 mL, 223 mmol, 1.0 equiv). The solution was refluxed for three hours. When $^1H$ NMR showed the reaction was complete, the reaction mixture was cooled to room temperature before being treated with concentrated aqueous HCl (250 mL) to pH 1-2. The white phthalhydrazide precipitate was collected by filtration and washed with 95% aqueous ethanol (4×100 mL). The combined filtrates were then concentrated to about 100 mL before 250 mL of $H_2O$ was added. The insoluble material was removed by filtration and the filtrates were concentrated to dryness in vacuo. The filtrates were recrystallized from ethanol/diethyl ether and dried in vacuo to afford the desired 3-fluoro-propylamine monohydrochloride salt 113 (20.83 g, 83.8% yield) as white crystals. This product was used directly in subsequent reactions without further purification. $^1H$ NMR (DMSO-$d_6$, 300 MHz) δ 1.89-2.07 (m, 2H), 2.52-2.90 (m, 2H), 4.47 (t, 5.8 Hz), 4.63 (t, 1H, J=5.8 Hz), 8.19 (s, 3H).

ii. Synthesis of Bromide 115

Method A

To a solution of amine 113 (6.0 g, 52.8 mmol, 1.16 equiv) in DMF (200 mL) was added 4-bromobenzalaldehyde 114 (8.50 g, 45.5 mmol) at room temperature. The resulting reaction mixture was then treated with sodium triacetoxyborohydride ($NaB(OAc)_3H$, 16.10 g, 72.0 mmol, 1.6 equiv) at room temperature and stirred for 2 h. When TLC and HPLC/MS showed the reaction was complete, the reaction mixture was quenched with water (100 mL). The resulting aqueous mixture was treated with solid sodium carbonate ($Na_2CO_3$, 99.64 g, 91.0 mmol, 2.0 equiv) and di-tert-butyl dicarbonate ($BOC_2O$, 12.9 g, 59.1 mmol, 1.3 equiv) at room temperature. The mixture was then stirred at room temperature for 1.5 h before being quenched with water (100 mL). The reaction mixture was then extracted with EtOAc (3×60 mL). The combined organic extracts were washed with 0.5 M aqueous HCl (100 mL) and water (3×100 mL), dried over anhydrous sodium sulfate ($Na_2SO_4$) and concentrated in vacuo. The residue was then purified by flash column chromatography (3-4% EtOAc/hexane) to afford the desired (4-bromo-benzyl)-(3-fluoro-propyl)-carbamic acid tert-butyl ester 115 (11.38 g, 72% yield) as a colorless oil. $C_{15}H_{21}BrFNO_2$, HPLC/MS (ESI) m/e 347 ($M^++H$).

Method B

A solution of 4-bromobenzylamine hydrochloride 116 (2.225 g, 10.0 mmol) and potassium carbonate (2.07 g, 15.0 mmol, 1.5 equiv) in THF (20 mL) and water (5 mL) was treated with $BOC_2O$ (2.40 g, 11.0 mmol, 1.1 equiv) at room temperature and stirred for 12 h. When TLC and HPLC/MS showed the reaction was complete, the reaction mixture was treated with water (10 mL) and EtOAc (40 mL). The two layers were separated, and the aqueous layer was extracted with EtOAc (20 mL). The combined organic extracts were washed with water (2×20 mL) and saturated aqueous NaCl (20 mL), dried over MgSO$_4$, and concentrated in vacuo. The residue was further dried in vacuo to afford the desired (4-bromo-benzyl)-carbamic acid tert-butyl ester 117 (2.60 g, 90.9% yield) as a colorless oil.

To a solution of 117 (286 mg, 1.0 mmol) in anhydrous DMF (3.0 mL) was added sodium hydride (NaH, 60% oil dispersion, 48.0 mg, 1.2 mmol, 1.2 equiv) at 0° C. The resulting mixture was stirred at 0° C. for 30 min before 1-bromo-3-fluoropropane 118 (170 mg, 1.2 mmol, 1.2 equiv) was added. The reaction mixture was subsequently warmed to 50-60° C. and stirred for 24 hours. The reaction mixture was then quenched with water (10 mL), and the resulting aqueous solution was extracted with EtOAc (2×20 mL). The combined organic extracts were washed with water (10 mL) and saturated aqueous NaCl (10 mL), dried over MgSO$_4$ and concentrated in vacuo. The residue was purified by column chromatography (10-15% EtOAc/hexane gradient elution) to afford the desired (4-bromo-benzyl)-(3-fluoro-propyl)-carbamic acid tert-butyl ester 115 (158 mg, 46% yield) as a colorless oil.

Method C

A solution of 4-bromobenzylbromide 119 (0.30 g, 1.20 mmol) and amine 113 (0.272 g, 2.40 mmol, 2.0 equiv) in anhydrous DMF (8.0 mL) was treated with diisopropylethylamine (Hunig's base, 2.0 mL) at room temperature. The resulting reaction mixture was warmed to 60° C. for 24 h. When TLC and HPLC showed the reaction was complete, the reaction mixture was cooled to 25° C. before being treated with water (8.0 mL). The resulting aqueous solution was then treated with solid sodium bicarbonate (NaHCO$_3$, 0.30 g, 3.60 mmol, 3.0 equiv) and BOC$_2$O (0.524 g, 2.40 mmol, 2.0 equiv) at 25° C. and stirred for 24 h. When TLC and HPLC/MS showed the reaction was complete, the reaction mixture was treated with water (20 mL) and EtOAc, 20 mL. The two layers were separated, and the aqueous layer was extracted with EtOAc (2×30 mL). The combined organic extracts were washed with H$_2$O (4×10 mL) and saturated aqueous NaCl (10 mL), dried over MgSO$_4$, and concentrated in vacuo. The residue was purified by column chromatography (3% EtOAc/hexanes) to afford the desired (4-bromo-benzyl)-(3-fluoro-propyl)-carbamic acid tert-butyl ester 115 (0.24 g, 57.8% yield) as a colorless oil.

iii. Synthesis of Boronic Acid 120

To a solution of bromide 115 (3.0 g, 8.7 mmol) in anhydrous THF (30 mL) at −78° C. was added a 2.5 M solution of n-BuLi in hexane (3.64 mL, 9.1 mmol, 1.05 equiv). The resulting reaction mixture was stirred at −78° C. for 1 h before trimethyl borate (B(OMe)$_3$, 1.2 mL, 10.4 mmol, 1.2 equiv) was added dropwise. The resulting reaction mixture was stirred at −78° C. for 0.5 h before being gradually warmed to room temperature overnight. The reaction mixture was poured into water (60 mL), and the aqueous solution was treated with 1.0 N aqueous HCl to pH 4.0. The aqueous mixture was then extracted with EtOAc (4×30 mL). The combined organic extracts were washed with saturated aqueous NaCl (30 mL), dried over anhydrous Na$_2$SO$_4$, and concentrated in vacuo to obtain the desired 4-(N-tert-butylcarbonyl-3-fluoropropylaminomethyl)phenyl boronic acid 120 (2.5 g). This product was directly used in subsequent reactions without further purification. C$_{15}$H$_{23}$BFNO$_4$, HPLC/MS (ESI) role 312 (M$^+$+H).

d. Synthesis of Compound 11

Scheme 5 depicts the synthesis of compound 11 from aryl iodide 108 and aryl boronic acid 120.

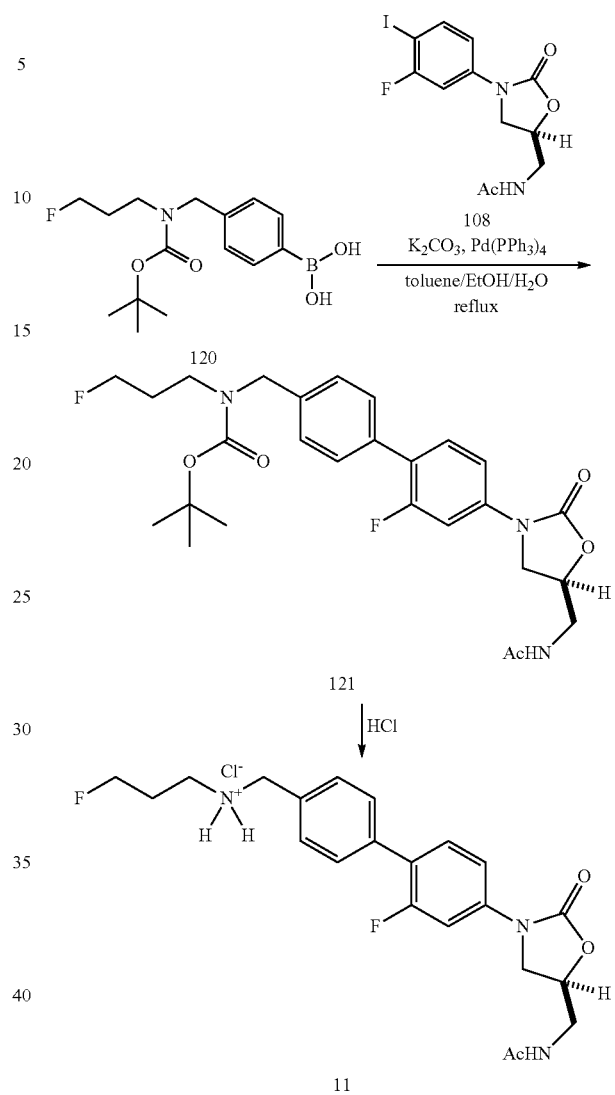

Scheme 5

A suspension of aryl boronic acid 120 (2.50 g, 8.03 mmol) in a mixture of toluene (24 mL), EtOH (8 mL), and water (8 mL) was treated with aryl iodide 108 (2.53 g, 6.7 mmol, 0.83 equiv) and solid K$_2$CO$_3$ (2.80 g, 20.1 mmol, 3.0 equiv) at room temperature. The resulting reaction mixture was degassed three times under a steady stream of argon before tetrakis(triphenylphosphine)palladium (0) (Pd(PPh$_3$)$_4$, 387 mg, 0.335 mmol, 0.05 equiv) was added. The resulting reaction mixture was degassed three times under a steady stream of argon before being warmed to reflux for 8 h. When TLC and HPLC/MS showed the reaction was complete, the reaction mixture was cooled to room temperature before being poured into water (60 mL) and EtOAc (60 mL). The two layers were separated, and the organic phase was washed with water (30 mL) and saturated aqueous NaCl (2×30 mL), dried over anhydrous Na$_2$SO$_4$, and concentrated in vacuo. The product was then recrystallized from EtOAc/hexanes and dried in vacuo to afford the desired (5S)-{4'-[5-(acetylaminomethyl)-2-oxo-oxazolidin-3-yl]-2'-fluoro-biphenyl-4-ylmethyl}-(3-fluoro-propyl)-carbamic acid tert-butyl ester 121 (1.3 g, 30%) as an off-white powder.

A solution of BOC-amine 121 (15.65 g, 30.3 mmol) in CH$_2$Cl$_2$ (30 mL) was treated with a solution of 4 N hydrogen chloride in 1,4-dioxane (37.5 mL, 150.0 mmol, 5.0 equiv) at room temperature and stirred for 12 h. When TLC and HPLC/MS showed that the reaction was complete, the solvents were removed in vacuo. The residue was suspended in a mixture of acetonitrile (CH$_3$CN, 200 mL) and methanol (MeOH, 50 mL), and the resulting slurry was stirred at room temperature for 1 h. The solids were collected by filtration, washed with 20% MeOH/CH$_3$CN (2×50 mL), and dried in vacuo to afford the desired (5S)—N-(3-{2-fluoro-4'-[(3-fluoro-propylamino)-methyl]-biphenyl-4-yl}-2-oxo-oxazolidin-5-ylmethyl)-acetamide mono hydrochloride salt 11 (13.0 g, 95.3% yield) as white crystals. $^1$H NMR (300 MHz, DMSO-d$_6$) δ 1.90 (s, 3H, COCH$_3$), 2.11-2.20 (m, 2H), 3.10 (m, 2H), 3.50 (t, 2H, J=5.4 Hz), 3.87 (dd, 1H, J=6.4, 9.2 Hz), 4.24 (t, 1H, J=9.1 Hz), 4.27 (s, 2H, ArCH$_2$), 4.54 (t, 1H, J=5.8 Hz), 4.70 (t, 1H, J=5.8 Hz), 4.83 (m, 1H), 7.50 (dd, 1H, J=2.2, 8.6 Hz), 7.65-7.74 (m, 6H, aromatic-H), 8.37 (t, 1H, J=5.8 Hz, NHCOCH$_3$), 9.43 (br. s, 2H, RArN$^+$H$_2$). C$_{22}$H$_{25}$F$_2$N$_3$O$_3$HCl, LCMS (EI) m/e 418 (M$^+$+H).

Example 2

Scheme 6 depicts an alternate synthesis of aryl boronic acid 120, which is coupled to aryl iodide 108 to yield compound 11.

A solution of 4-formylphenyl boronic acid 122 (10.0 g, 66.69 mmol) in anhydrous DMF (150 mL) was treated with 3-fluoropropylamine hydrochloride salt 113 (8.70 g, 76.70 mmol, 1.15 equiv, prepared as described in Example 1, above) at room temperature. The resulting mixture was treated with NaB(OAc)$_3$H (28.30 g, 133.39 mmol, 2.0 equiv) at room temperature and stirred for 3 h. When TLC and HPLC/MS showed the reaction was complete, the reaction mixture was treated with water (150 mL), solid Na$_2$CO$_3$ (14.14 g, 133.39 mmol, 2.0 equiv), and BOC$_2$O (22.05 g, 100.04 mmol, 1.5 equiv). The resulting reaction mixture was stirred at room temperature for 3 h. When TLC and HPLC/MS showed the reaction was complete, the reaction mixture was poured into water (500 mL) and EtOAc (500 mL). The two layers were separated and the aqueous layer was treated with a 2 N aqueous HCl (130 mL) to pH 4. The aqueous layer was then extracted with EtOAc (160 mL), and the combined organic layers were washed with water (2×100 mL) and saturated aqueous NaCl (2×100 mL), dried over Na$_2$SO$_4$, and concentrated in vacuo. The residue was further dried in vacuo to afford the desired 4-(N-tert-butylcarbonyl-3-fluoropropylaminomethyl)phenyl boronic acid 120 (25.0 g) as a pale-yellow oil. This product was found to be identical with the material obtained from Example 1 above and was directly used in the subsequent reaction without further purification.

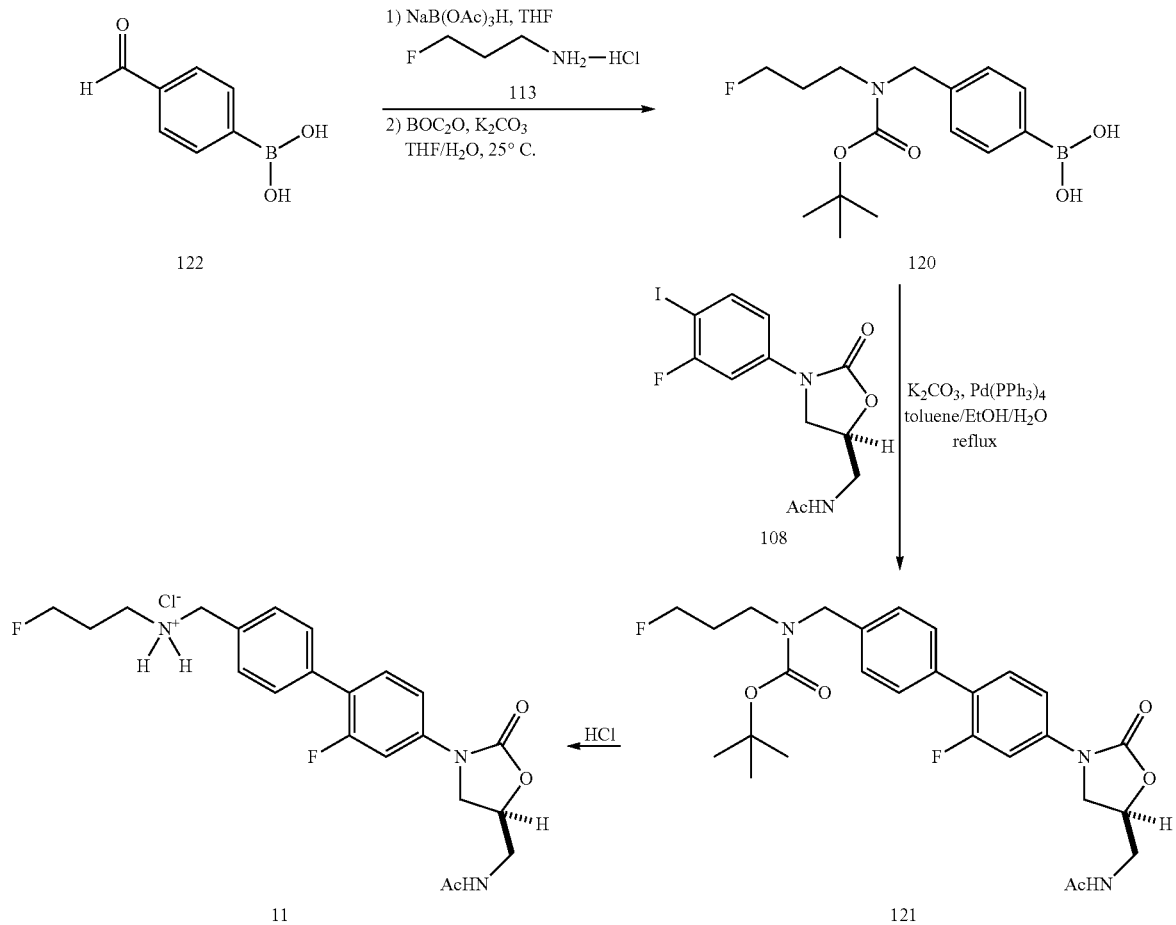

Scheme 6

A suspension of aryl boronic acid 120 (25.0 g, 64.30 mmol, 1.45 equiv) in a mixture of toluene (120 mL), EtOH (40 mL), and water (40 mL) was treated with (5S)—N-[3-(3-fluoro-4-iodo-phenyl)-2-oxo-oxazolidin-5-ylmethyl]-acetamide 108 (16.80 g, 44.44 mmol, prepared as described in Example 1, above) and solid K$_2$CO$_3$ (18.40 g, 133.4 mmol, 3.0 equiv) at room temperature. The resulting reaction mixture was degassed three times under a steady stream of argon before being treated with Pd(PPh$_3$)$_4$ (2.57 g, 2.23 mmol, 0.05 equiv). The resulting reaction mixture was degassed three times under a steady stream of argon before being warmed to reflux for 8 h. When TLC and HPLC/MS showed the reaction was complete, the reaction mixture was cooled to room temperature before being poured into water (300 mL) and ethyl acetate (EtOAc, 300 mL). The two layers were separated, and the organic phase was washed with water (60 mL) and saturated aqueous NaCl (2×50 mL), dried over anhydrous Na$_2$SO$_4$, and concentrated in vacuo. The product was recrystallized from EtOAc/hexanes and dried in vacuo to afford the desired (5S)-{4'-[5-(acetylamino-methyl)-2-oxo-oxazolidin-3-yl]-2'-fluoro-biphenyl-4-ylmethyl}-(3-fluoro-propyl)-carbamic acid tert-butyl ester 121 (21.2 g, 61.5% yield for three steps) as an off-white powder.

BOC-protected amine 121 was subsequently treated with 4 N hydrogen chloride in 1,4-dioxane as in Example 1 to afford compound 11. The product obtained from this process was identical by NMR and LCMS to the material obtained in Example 1.

Example 3

Scheme 7 depicts the synthesis of compound 11 from aryl bromide 115 and aryl boronic ester 123.

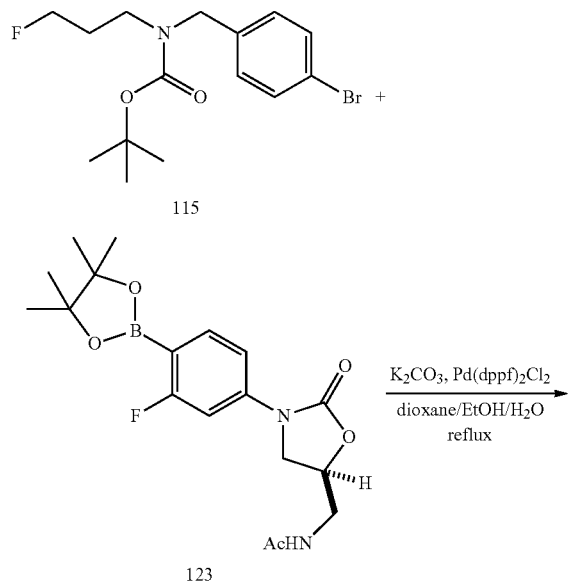

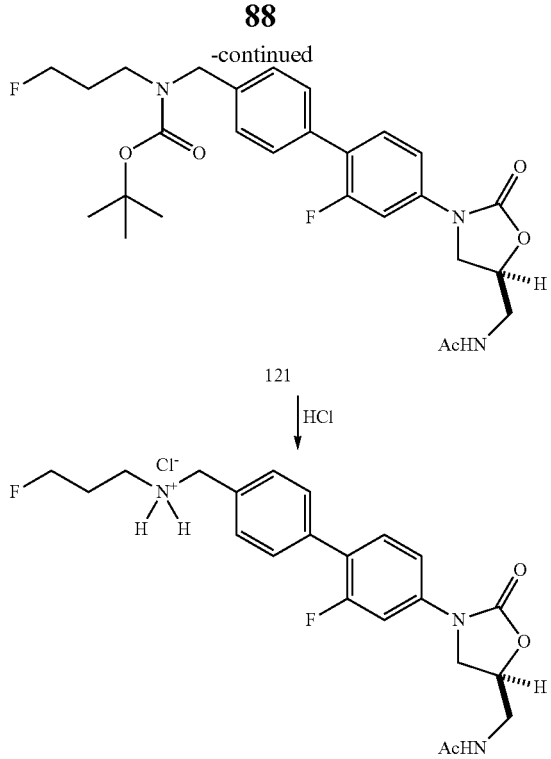

Synthesis of Boronic Ester 123

A suspension of (5S)—N-[3-(3-fluoro-4-iodo-phenyl)-2-oxo-oxazolidin-5-ylmethyl]-acetamide 108 (20.0 g, 52.8 mmol, prepared as described in Example 1, above) in anhydrous 1,4-dioxane (130 mL) was treated with 4,4,5,5-tetramethyl-[1,3,2]dioxaborolane (10.2 g, 11.6 mL, 80.0 mmol, 1.5 equiv) and triethylamine (16.0 g, 22.4 mL, 158.4 mmol, 3.0 equiv) at room temperature. The resulting reaction mixture was degassed three times under a steady stream of argon before being treated with dichloro[1,1'-bis(diphenylphosphino)ferrocene]palladium (II) (Pd(dppf)$_2$Cl$_2$, 1.32 g, 1.6 mmol, 0.03 equiv) at room temperature. The resulting reaction mixture was degassed three times under a steady stream of argon before being warmed to reflux for 7 h. When HPLC/MS showed the reaction was complete, the reaction mixture was cooled to room temperature before being treated with water (100 mL) and ethyl acetate (100 mL). The two layers were separated, and the aqueous layer was extracted with ethyl acetate (2×50 mL). The combined organic extracts were washed with water (2×50 mL) and saturated aqueous NaCl (50 mL), dried over MgSO$_4$, and concentrated in vacuo. The residual brown oil was further dried in vacuo to afford the desired (5S)—N-{3-[3-fluoro-4-(4,4,5,5-tetramethyl-[1,3,2]dioxaborolan-2-yl)-phenyl]-2-oxo-oxazolidin-5-ylmethyl}acetamide 123 (18.8 g, 94%) as brown solids. This product was directly used in subsequent reactions without further purification. C$_{18}$H$_{24}$BFN$_2$O$_5$, HPLC/MS (ESI) m/e 379 (M$^+$+H).

Synthesis of Compound 11

A solution of boronic ester 123 (1.40 g, 3.7 mmol, 1.3 equiv) and (4-bromo-benzyl)-(3-fluoro-propyl)-carbamic acid tert-butyl ester 115 (1.0 g, 2.89 mmol, prepared as described in Example 1, above) in a mixture of 1,4-dioxane (21 mL), EtOH (7.0 mL) and H$_2$O (7.0 mL) was treated with solid potassium carbonate (1.2 g, 8.7 mmol, 3.0 equiv) at room temperature. The resulting reaction mixture was degassed three times under a steady stream of argon before being treated with Pd(dppf)$_2$Cl$_2$ (118 mg, 0.144 mmol, 0.05 equiv) at room temperature. The reaction mixture was degassed three times under a steady stream of argon before being warmed to reflux for 2 h. When TLC and HPLC/MS showed the reaction was complete, the reaction mixture was cooled to room temperature before being treated with water (60 mL). The aqueous solution was then extracted with CH$_2$Cl$_2$ (3×20 mL), and the combined organic extracts were washed with water (2×20 mL) and saturated aqueous NaCl (20 mL), dried over MgSO$_4$, and concentrated in vacuo. The residue was purified by flash column chromatography (0-5% MeOH—CH$_2$Cl$_2$ gradient elution) to afford the desired (5S)-{4'-[5-(acetylamino-methyl)-2-oxo-oxazolidin-3-yl]-2'-fluoro-biphenyl-4-ylmethyl}-(3-fluoro-propyl)-carbamic acid tert-butyl ester 121 (1.36 g, 91% yield) as a colorless oil, which solidified upon standing at room temperature in vacuo.

BOC-protected amine 121 was subsequently treated with 4 N hydrogen chloride in 1,4-dioxane as in Example 1 to afford compound 11. The product obtained from this process was identical by NMR and LCMS to the material obtained in Example 1.

Example 4

Synthesis of Compound 63

Scheme 8 illustrates the synthesis of amide 63. 2,5-Dibromopyridine 124 is converted to activated pyridyl ester 125 which is then treated with histamine 126 to provide amide 127. The Suzuki coupling of 127 and boronate 123 gave the final target amide 63.

Under an argon atmosphere, triethylamine (0.31 mL, 2.25 mmol) was added to a mixture of 2,5-dibromopyridine 124 (355 mg, 1.5 mmol), palladium acetate (16.8 mg. 0.075 mmol), Xantphos (4,5-bis(diphenylphosphino)-9,9-dimethylxanthene, 43.4 mg, 0.075 mmol) and N-hydroxysuccinimide (241.5 mg, 2.1 mmol) in DMSO (2 mL). The solution was purged with carbon monoxide for 15 min and stirred under a carbon monoxide balloon at 80° C. for 16 h. The reaction mixture was then cooled to room temperature, diluted with 20 mL of ethyl acetate and washed with saturated sodium bicarbonate solution and water. The organic phase was dried over sodium sulfate and evaporated to give crude product. Chromatography on silica gel using hexane:acetone (3:1) provided ester 125 (75 mg; 17%). $^1$HNMR (300 MHz, CDCl$_3$) δ 8.85 (m, 1H), 8.06 (m, 2H), 2.90 (s, 4H).

A mixture of active ester 125 (350 mg, 1.17 mmol), histamine dihydrochloride 126 (216 mg, 1.17 mmol) and triethylamine (Et$_3$N, 0.33 mL, 2.34 mmol) in CH$_2$Cl$_2$ (5 mL) was stirred at room temperature for 1 h. The reaction was washed with brine and dried under vacuum. The crude product was purified by chromatography (15:1:0.05/CH$_2$Cl$_2$:MeOH:NH$_3$.H$_2$O) to afford 127 (280 mg; 81%). LCMS (ESI) m/z 295 (M+H)$^+$.

Under an argon atmosphere, a mixture of amide 127 (230 mg, 0.78 mmol), boronate 123 (295 mg, 0.78 mmol), PdCl$_2$(dppf)$_2$ (19 mg, 0.023 mmol) and K$_2$CO$_3$ (323 mg, 2.34 mmol) in 5 mL of a mixture of dioxane:EtOH:H$_2$O (3:1:1) were heated at 100° C. for 12 h. The reaction was concentrated and the residue was dissolved in MeOH (2 mL) and CH$_2$Cl$_2$ (10 mL). Inorganic salts were removed by filtration. The filtrate was concentrated and purified by chromatography (15:1:0.05/CH$_2$Cl$_2$:MeOH:NH$_3$.H$_2$O) to afford amide 63 (106 mg; 29%). LCMS (ESI) m/z 467 (M+H)$^+$.

Scheme 8

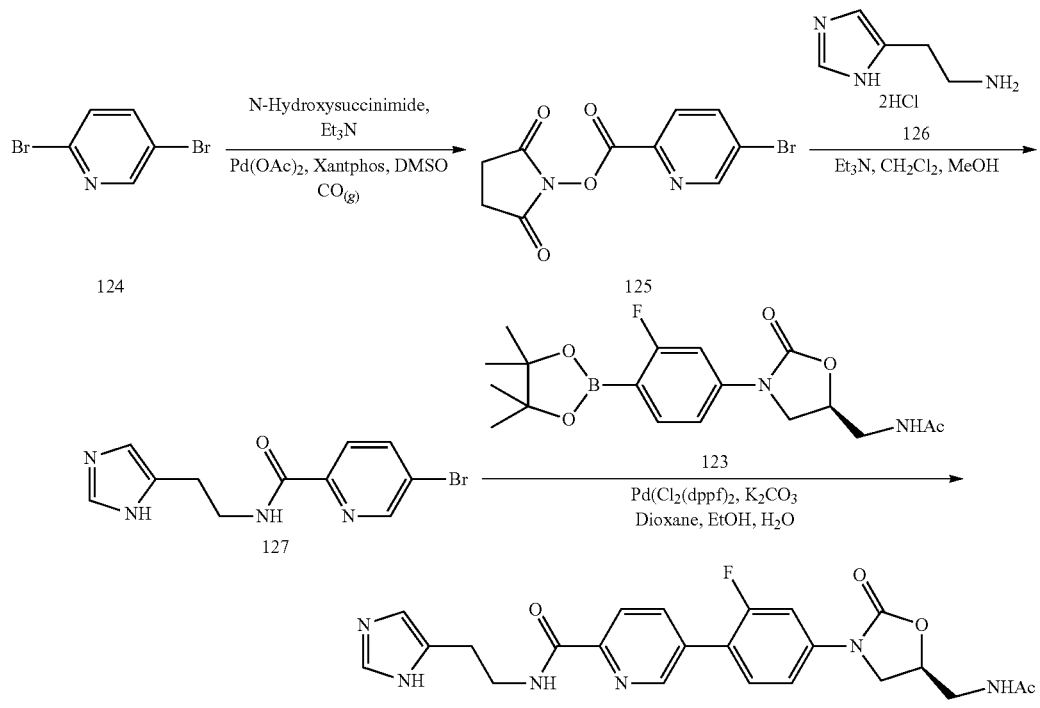

Example 5

Synthesis of Compounds 64 and 65

Scheme 9 illustrates the synthesis of amides 64 and 65. Aryl bromides 128 and 129 were coupled to boronate 123 to afford 64 and 65 respectively.

Scheme 9

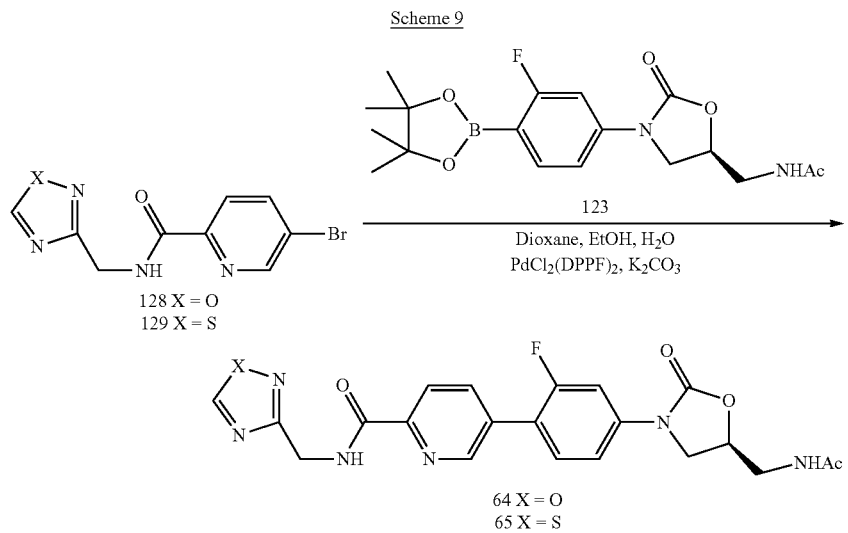

128 X = O
129 X = S

64 X = O
65 X = S

Synthesis of Compound 64

A mixture of 4-bromobenzoyl chloride (110 mg, 0.5 mmol), 1,2,4-oxadiazol-3-yl-methylamine hydrochloride (68 mg, 0.5 mmol), DMF (1 drop) and $Et_3N$ (0.33 mL, 2.34 mmol) in $CH_2Cl_2$ (5 mL) was stirred at room temperature for 4 h. The reaction was washed with brine and dried under vacuum to afford crude amide 128. The resultant amide 128 was added to a mixture of boronate 123 (189 mg, 0.5 mmol), $Pd(dppf)_2Cl_2$ (20 mg, 0.025 mmol) and $K_2CO_3$ (207 mg, 1.5 mmol) in 5 mL of dioxane:EtOH:$H_2O$ (3:1:1) under an argon atmosphere. After being heated at 100° C. for 12 h, the reaction was diluted with water and MeOH, and then filtered through celite. The filtrate was concentrated to remove organic solvent. The crude product was collected by filtration and further purified by chromatography (25:1:0.05/$CH_2Cl_2$:MeOH:$NH_3.H_2O$) to afford compound 246 (45 mg; 32% (2 steps)). LCMS (ESI) m/z 452 (M-H)$^+$.

Synthesis of Compound 65

A mixture of 4-bromobenzoyl chloride (29 mg, 0.132 mmol), 1,2,4-thiadiazol-3-yl-methylamine hydrochloride (20 mg, 0.132 mmol), DMF (1 drop) and $Et_3N$ (27 mg, 0.264 mmol) in THF (4 mL) was stirred at room temperature for 2 h. The reaction was concentrated, dissolved in $CH_2Cl_2$, washed with brine and dried under vacuum to afford crude amide 129. The resultant amide 129 was added to a mixture of boronate 123 (50 mg, 0.132 mmol), $PdCl_2(dppf)_2$ (6 mg, 0.0066 mmol) and $K_2CO_3$ (55 mg, 0.396 mmol) in 2 mL of dioxane:EtOH:$H_2O$ (3:1:1) under an argon atmosphere. After being heated at 100° C. for 12 h, the reaction was concentrated, dissolved in EtOAc, washed with brine and dried under vacuum. The crude product was purified by chromatography on silica gel (25:1:0.05/$CH_2Cl_2$:MeOH:$NH_3.H_2O$) to afford compound 65 (30 mg; 48% (2 steps)). LCMS (ESI) m/z 470 (M+H)$^+$.

Example 6

Synthesis of Compound 66

Scheme 10

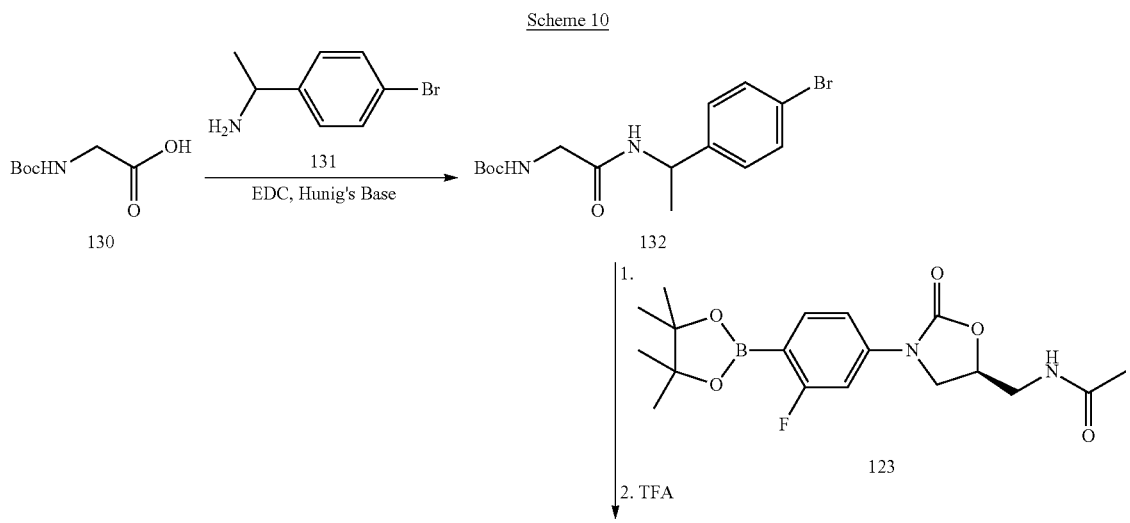

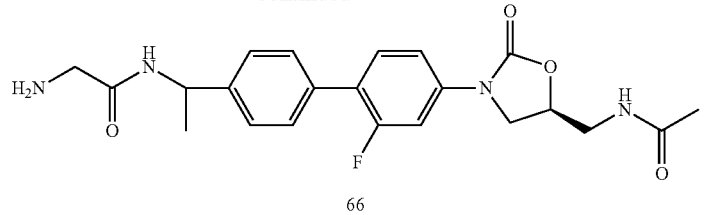

66

To a solution of Boc-glycine 130 (1.04 g, 5.88 mmol) and 4-bromobenzylethylamine 131 (1.00 g, 4.90 mmol) in CH$_2$Cl$_2$ (25 mL) at room temperature was added Hunig's base (1.30 mL, 7.35 mmol). The mixture was stirred at room temperature for 16 h. The mixture was poured into water (40 mL) and sat. NaHCO$_3$ (3 mL), then extracted with CH$_2$Cl$_2$ (60 mL), washed with water (100 mL), and dried with Na$_2$SO$_4$. The residue was isolated by column chromatography (50/50/0.1 EtOAc/Hexane/NH$_4$OH), to give 1.30 g of amide 132 as a white crystalline solid in 69% yield. $^1$HNMR (300 MHz, CDCl$_3$, ppm): δ: 7.37 (d, J=7 Hz, 2H), 7.09 (d, J=7 Hz, 1H), 6.50 (s br, 1H), 5.15 (s br, 1H), 5.01-4.95 (m, 1H), 3.69 (d, J=6 Hz, 2H), 1.39 (d, J=7 Hz, 3H), 1.37 (s, 9H).

yield. The Boc-protected product (200 mg) taken up in 2 mL CH$_2$Cl$_2$ and 2 mL TFA and the mixture was stirred at room temperature for 3 hr. The solvent was removed in vacuo and the residue was purified by column chromatography (15:85:0.1 MeOH/CH$_2$Cl$_2$/NH$_4$OH) to give 168 mg compound 66 in 99% yield. $^1$HNMR (300 MHz, CDCl$_3$, ppm, partial): δ: 7.64-7.33 (m, 7H), 5.13-5.07 (m, 1H), 4.19 (ddd, J=9, 3, 3 Hz, 1H), 3.87 (ddd, J=9, 7, 3 Hz, 1H), 3.77-3.50 (m, 5H), 1.99 (s, 3H), 1.54 (d, J=7 Hz, 3H). LCMS (ESI) m/e 429 (M+H)$^+$.

Example 7

Synthesis of Compound 67

Scheme 11 illustrates the synthesis of compound 67.

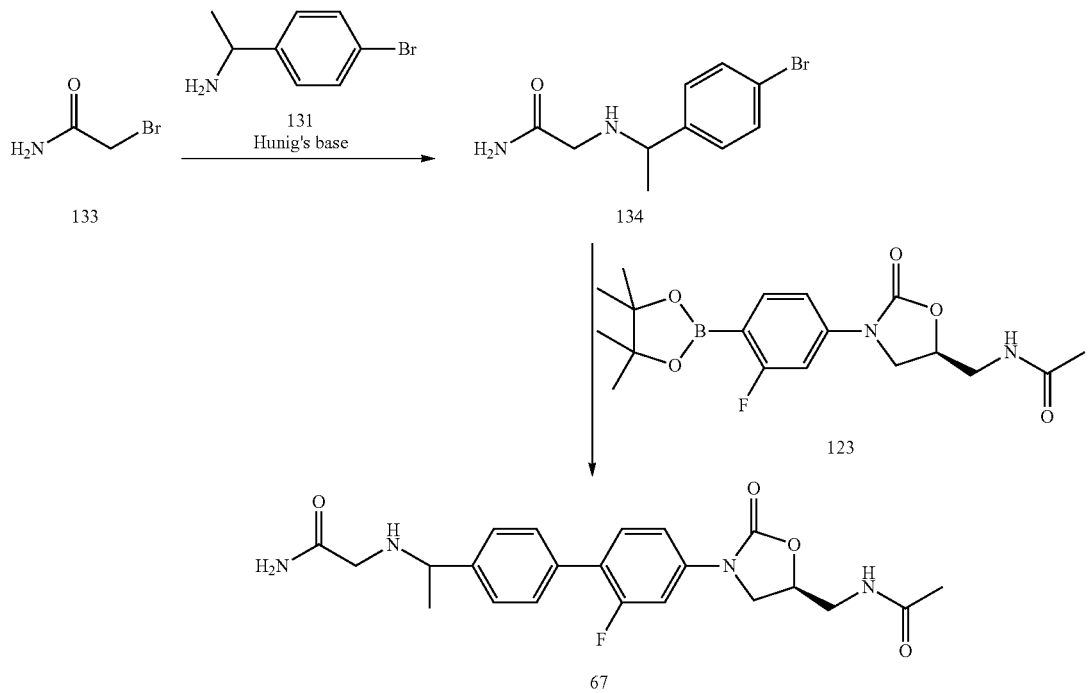

A mixture of amide 132 (143 mg, 0.40 mmol) and boronic ester 123 (168 mg, 0.4 mmol), Pd(dppf)$_2$Cl$_2$ (16 mg, 0.02 mmol) and K$_2$CO$_3$ (221 mg, 1.60 mmol) in dioxane (3 mL), EtOH (1 mL) and H$_2$O (1 mL) was degassed with argon. The mixture was stirred at 90-95° C. for 3 h, then water (10 mL) was added. The mixture was extracted with CH$_2$Cl$_2$ (4×30 mL) and dried over Na$_2$SO$_4$. The residue was purified by column chromatography (5:100:0.1 MeOH/CH$_2$Cl$_2$/NH$_4$OH) to yield 200 mg Boc-protected product in 100%

To a solution of 2-bromoacetamide 133 (827 mg, 5.88 mmol), and 4-bromobenzyl-ethylamine 131 (1.00 g, 4.90 mmol) in MeOH (5 mL) and CH$_2$Cl$_2$ (5 mL) at room temperature was added Hunig's base (5 mL). The mixture was stirred at 50-60° C. for 16 h, then water (30 mL) was added. The mixture was extracted with CH$_2$Cl$_2$ (4×30 mL), dried over Na$_2$SO$_4$, and the solvent was removed in vacuo to provide 1.27 g amide 134 as a white crystalline solid in 100% yield. $^1$HNMR (300 MHz, CDCl$_3$, ppm): δ: 7.38 (d, J=8 Hz, 2H), 7.09 (d, J=8 Hz, 1H), 6.77 (s br, 1H), 5.69 (s br, 1H), 3.67 (q, J=7 Hz, 1H), 3.07 (s, 2H), 1.29 (d, J=7 Hz, 3H).

A mixture of amide 34 (103 mg, 0.40 mmol) and boronic ester 123 (168 mg, 0.4 mmol), Pd(dppf)$_2$Cl$_2$ (16 mg, 0.02 mmol) and K$_2$CO$_3$ (221 mg, 1.60 mmol) in dioxane (3 mL), EtOH (1 mL) and H$_2$O (1 mL) was degassed with argon. The mixture was stirred at 90-95° C. for 3 h, then water (10 mL) was added. The mixture was extracted with CH$_2$Cl$_2$ (4×30 mL), dried over Na$_2$SO$_4$, and the solvent was removed in vacuo. The residue was purified by column chromatography (7:100:0.1 MeOH/CH$_2$Cl$_2$/NH$_4$OH) to yield 85 mg compound 67 in 50% yield. $^1$HNMR (300 MHz, CDCl$_3$, ppm, partial): δ: 7.70-7.30 (m, 7H), 7.09 (s br, 1H), 6.31 (s br, 1H), 5.63 (s br, 1H), 4.96-4.92 (m, 1H), 4.22 (t, J=9 Hz, 1H), 3.33 (s, 2H), 2.13 (s, 3H), 1.55 (d, J=7 Hz, 3H). LCMS (ESI) m/e 451.2 (M+Na)$^+$.

Example 8

Synthesis of Compound 68

Scheme 12 illustrates the synthesis of compound 68.

(25 mL). The two layers were separated, and the aqueous layer was extracted with ethyl acetate (2×20 mL). The combined organic extracts were washed with water (2×15 mL) and saturated aqueous NaCl solution (10 mL), dried over MgSO$_4$, and concentrated in vacuo. The residue was purified by flash column chromatography (5-25% EtOAc-hexane gradient elution) to afford the desired 4-(4-bromo-phenylsulfanylmethyl)pyridine (1.374 g; 82%) as a pale-yellow solid, which was directly used in subsequent reactions.

Synthesis of Compound 68

A solution of boronate 123 (200 mg, 0.53 mmol) and bromide 135 (150 mg, 0.53 mmol) in toluene (9 mL) was treated with solid potassium carbonate (220 mg, 1.6 mmol), ethanol (3.0 mL) and H$_2$O (3.0 mL) at room temperature, and the resulting reaction mixture was degassed three times under a steady stream of argon before being treated with Pd(dppf)$_2$Cl$_2$ (16 mg, 0.013 mmol) at room temperature. The reaction mixture was then degassed three times again under a steady stream of argon before being warmed to reflux for 2 h. When LCMS showed that the reaction was complete, the reaction

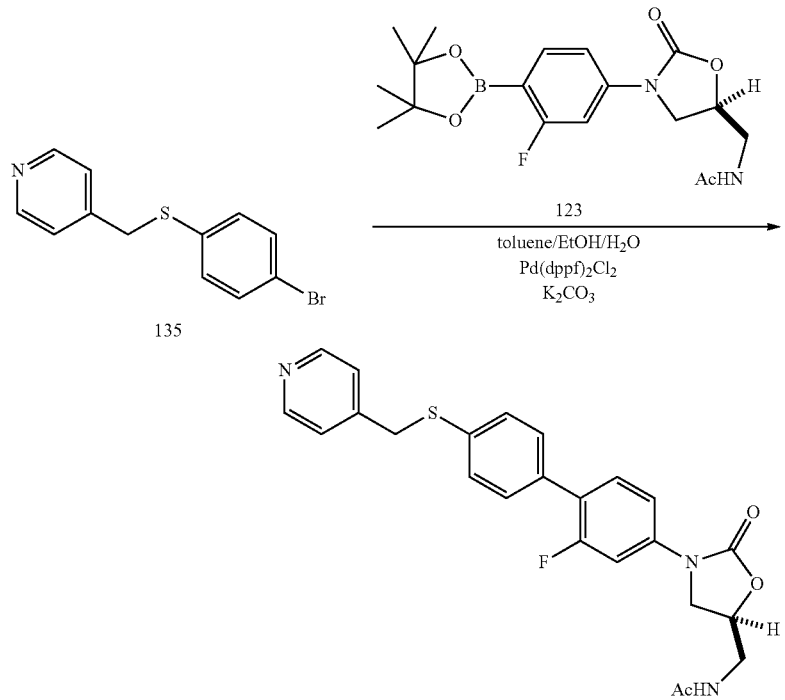

Synthesis of Bromide 135

A suspension of 4-bromomethylpyridine hydrochloride (1.59 g, 6.3 mmol) in THF (10 mL) was treated dropwise with a solution of potassium carbonate (3.33 g, 24.0 mmol) in H$_2$O (6 mL) at 0-5° C., and the resulting mixture was stirred at 0-5° C. for 10 min before being treated dropwise with a solution of 4-bromo-benzenethiol (1.14 g, 6.0 mmol) in THF (5.0 mL) at 0-5° C. under N$_2$. The resulting reaction mixture was subsequently stirred at 0-5° C. for an additional 20 min. When TLC and LCMS showed that the reaction was complete, the reaction mixture was treated with water (15 mL) and ethyl acetate mixture was cooled to room temperature before being treated with water (10 mL) and ethyl acetate (20 mL). The two layers were separated, and the aqueous layer was extracted with ethyl acetate (2×10 mL). The combined organic extracts were washed with water (2×10 mL) and saturated aqueous NaCl (10 mL), dried over MgSO$_4$, and concentrated in vacuo. The residue was then purified by flash column chromatography (0-5% MeOH—CH$_2$Cl$_2$ gradient elution) to afford compound 68 (177 mg; 74%) as a yellow oil, which solidified upon standing at room temperature in vacuo. LCMS (ESI) m/z 452 (M+H)$^+$.

Example 9

Synthesis of Compound 69

Scheme 13 illustrates the synthesis of compound 69.

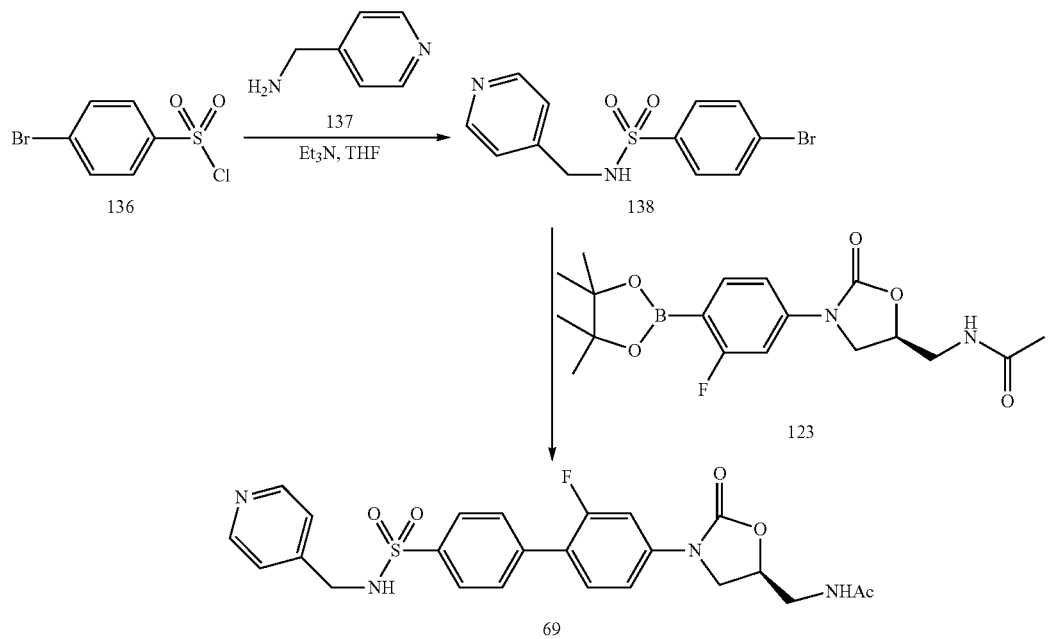

4-bromobenzenesulfonyl chloride 136 (2.56 g, 10 mmol) was added to a solution of 4-aminomethylpyridine 137 (1.08 g, 10 mmol) and triethylamine (2 mL, 14.3 mmol) in THF (20 mL) at 0° C. After stirring at 0° C. for 1 h, 50 mL of water was added. A white solid was collected by filtration, washing with EtOAc and dried in vacuo to give 3.10 g of bromide 138 in a yield of 95%.

Bromide 138 (327 mg, 1 mmol), boronate 123 (378 mg, 1 mmol), Pd(dppf)$_2$Cl$_2$ (40 mg, 0.05 mmol) and K$_2$CO$_3$ (414 mg, 3 mmol) were dissolved 8 mL of a mixture of dioxane:EtOH:H$_2$O (3:1:1) under argon atmosphere. After heating at 100° C. for 12 hours, the reaction mixture was added to 20 mL of cool water. The organic solvent was removed in vacuo and the crude product was collected by filtration. The crude product was treated with active charcoal and recrystallized in a mixed solvent system (1:2:2 MeOH/CH$_2$Cl$_2$/acetone) to give 155 mg of compound 69 in a yield of 31%. MS (ESI): 499.1 (100%, (M+H)$^+$).

Example 10

Synthesis of Compound 70

Scheme 14 depicts the synthesis of compound 70.

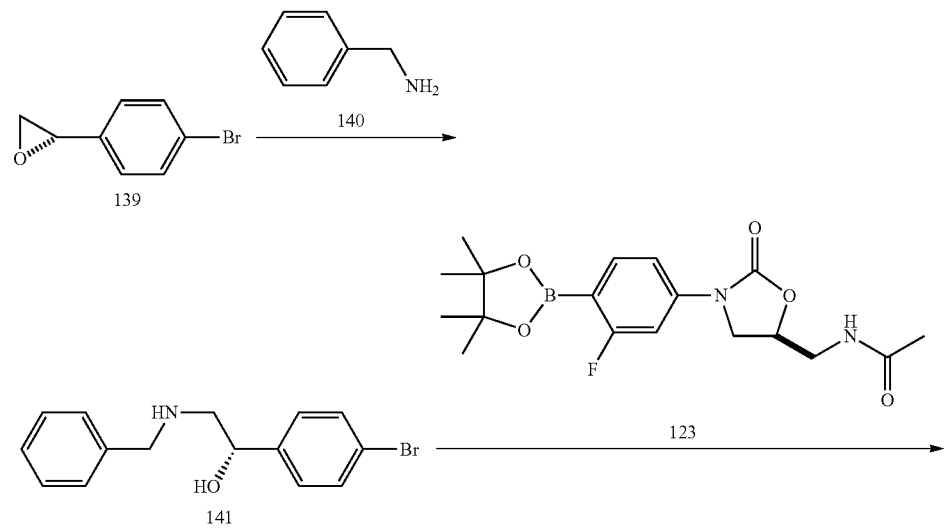

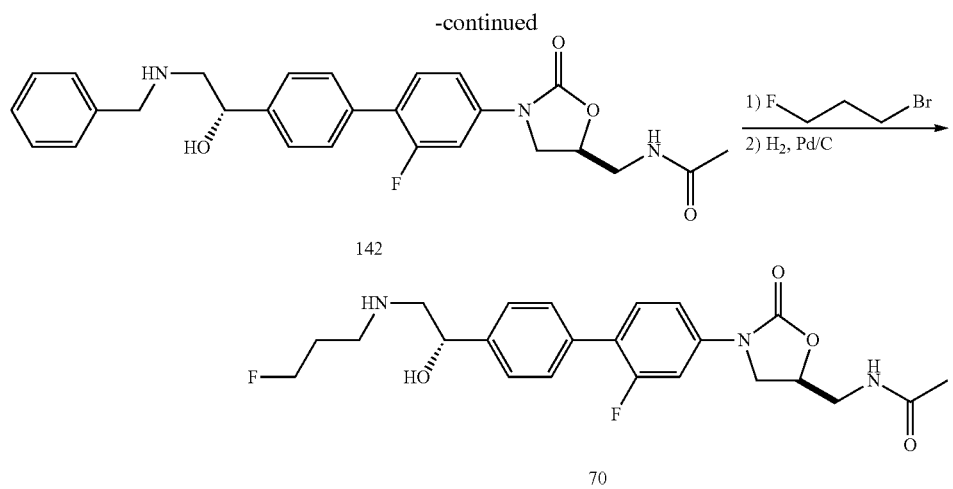

Synthesis of Epoxide 139

To a solution of 4-bromostyrene (5.00 g, 26.8 mmol) in CH$_2$Cl$_2$ (130 mL) was added anhydrous 4-methylmorpholine N-oxide (NMO, 12.90 g, 107.1 mmol) and (1S,2S)-(+)-[1,2-(cyclohexanodiamino-N,N'-bis(3,5-di-t-butyl-saficylidene)] manganese(III) chloride (Jacobsen catalyst, 850 mg, 1.34 mmol). The solution was cooled to −78° C., then 3-chloroperoxybenzoic acid (m-CPBA, 7.40 g, 42.8 mmol) was added in four portions every 10 min. The mixture was stirred at −78° C. for 2 h. The reaction was quenched by addition of aqueous Na$_2$S$_2$O$_3$ (10.0 g in 30 mL water), then the cooling bath was removed and water (70 mL) and 1N NaOH (60 mL) was added. The aqueous phase was extracted with CH$_2$Cl$_2$ (3×30 mL), dried with Na$_2$SO$_4$, and evaporated. The residue was purified by flash chromatography (4:100 Et$_2$O/hexane) to yield 5.20 g epoxide 139 (98% yield).

Synthesis of Compound 70

To a suspension of epoxide 139 (1 mmol) in acetonitrile (3.0 mL) at room temperature was added lithium perchloriate (LiClO$_4$, 1.05 mmol). After the formation of clear solution, benzylamine 140 (1.5 mmol) was added. The mixture was stirred at 80° C. for 4.5 h. The solvent was removed in vacuo and the residue was purified by flash column chromatography (3.5:100 MeOH/CH$_2$Cl$_2$), to afford 141 (460 mg; 50% yield). LCMS (ESI) m/z 307 (M+H)$^+$.

A suspension of 141 (1 eq), boronate ester 123 (1 eq), Pd(dppf)$_2$Cl$_2$ (0.05 eq), and K$_2$CO$_3$ (4 eq) in a 3:1:1 mixture of dioxane/EtOH/H$_2$O was degassed by passing a steady stream of argon through the mixture. The mixture was stirred at 80° C. for 3 h. The solvent was removed in vacuo and the residue was purified by flash column chromatography (3:100 MeOH/CH$_2$Cl$_2$), to yield amine 142 (690 mg; 96% yield). LCMS (ESI) m/z 439 (M+H)$^+$.

A mixture of amine 142 (80 mg, 0.168 mmol), 3-fluoro-1-bromopropane (47 mg, 0.335 mmol) and Hunig's base (117 μL, 0.670 mmol) in DMF (1.5 mL) was stirred at 55-60° C. for 15 h. The solvent was removed in vacuo and residue was purified by flash column chromatography (2:100 MeOH/CH$_2$Cl$_2$), to give 87 mg of the alkylation product (96% yield). LCMS (ESI) m/z 538 (M+H)$^+$.

To a solution of the alkylation product (80 mg, 0.149 mmol), in EtOH (1.5 mL) at room temperature was added 3N aqueous HCl (120 μL, 0.360 mmol), followed by 10% Pd—C (15 mg). The mixture was stirred under the atmosphere of H$_2$ (1 atm.) for 18 h. The mixture was passed through a pad of celite, and the cake was washed with MeOH (3×10 mL). The filtrate was evaporated to give the HCl salt of compound 70 (57 mg; 79% yield). LCMS (ESI) m/z 448 (M+H)$^+$.

Example 11

Synthesis of Compounds 71 and 72

Scheme 15 illustrates the synthesis of compounds 71 and 72. Hydroxyamidine 143 was converted to bromide 144, which was subsequently coupled to boronate 123 to afford compound 71. Hydroxyamidine 143 was transformed to oxadiazole 145, which was coupled to boronate 123 to afford compound 72.

Scheme 15
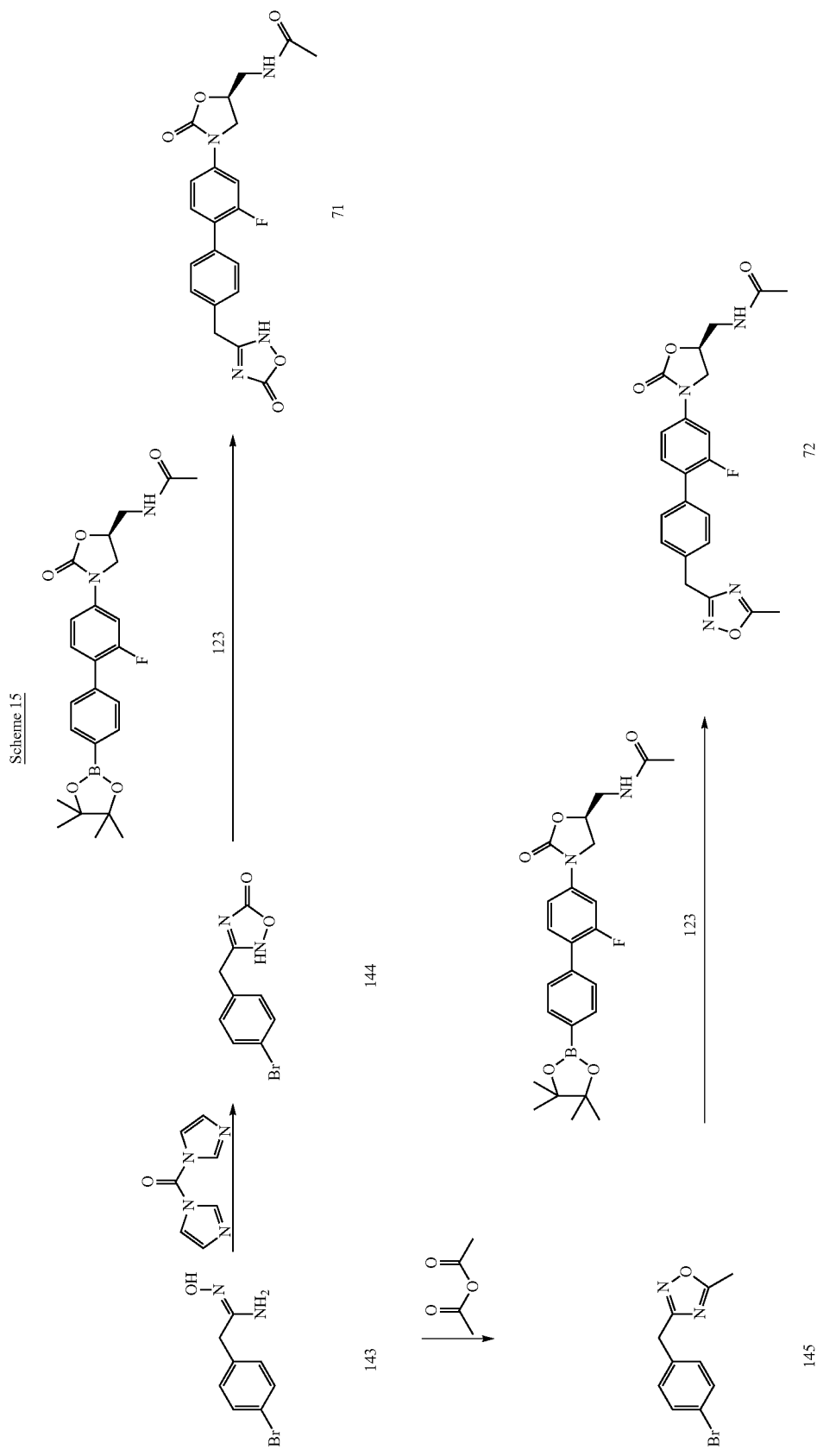

Synthesis of Hydroxamidine 143

A solution of 4-bromophenylacetonitrile (10 g, 54 mmol) in methanol (100 mL) was treated with sodium bicarbonate (2.2 g, 57 mmol) and hydroxylamine hydrochloride (4.0 g, 57 mmol) and refluxed for 1.5 h. Additional sodium bicarbonate (0.21 g, 5.4 mmol) and hydroxylamine hydrochloride (0.38 g, 5.4 mmol) were added, and the reaction mixture was refluxed for 12 h. The reaction mixture was cooled to 23° C. and the solvent removed in vacuo to afford hydroxyamidine 143 as a blue powder (4.0 g; 34%).

Synthesis of Compound 71

A solution of hydroxyamidine 143 (0.20 g, 0.91 mmol) in 1,4-dioxane (1 mL) was treated with 1,1'-carbonyldiimidazole (0.18 g, 1.1 mmol) and 1,8-diazabicyclo[5.4.0]undec-7-ene (DBU, 0.15 mL, 0.97 mmol) and stirred at 105° C. for 1 h. The reaction mixture was diluted with water and extracted with ethyl acetate. The water layer was treated with 1.0 M HCl (aqueous) until the pH was 2, and then extracted with ethyl acetate. The organic layer was dried ($Na_2SO_4$), and the solvent removed in vacuo to afford bromide 144 as a yellow powder (0.11 g; 49%).

A solution of boronate ester 123 (0.085 g, 0.220 mmol), bromide 144 (0.055 g, 0.220 mmol), and potassium carbonate (0.12 g, 0.90 mmol) in dioxane (1.4 mL), ethanol (0.46 mL) and water (0.46 mL) was degassed and treated with Pd(dppf)$Cl_2$ (6.0 mg, 6.7 mmol), degassed again, and heated at 80° C. for 1.5 h. The reaction mixture was diluted with $CH_2Cl_2$ and water, and the precipitate in the water layer was recovered by vacuum filtration to afford compound 71 as a grey powder (0.034 g; 36%). LCMS (ESI) m/z 427 (M+H)$^+$.

Synthesis of Compound 71

A solution of hydroxyamidine 143 (0.25 g, 1.1 mmol) in pyridine (5 mL) was cooled to 0° C. and treated with a solution of acetic anhydride (0.11 mL, 1.1 mmol) in pyridine (5 mL) and then stirred at 120° C. for 1.5 h. The reaction mixture was diluted with ethyl acetate, washed with 1M aqueous HCl and saturated aqueous sodium bicarbonate, dried over $Na_2SO_4$, and the solvent was evaporated in vacuo. The crude product was purified by flash chromatography to afford bromide 145 as a clear film (0.10 g; 36%).

A solution of boronate ester 123 (0.15 g, 0.40 mmol), bromide 145 (0.10 g, 0.40 mmol), and potassium carbonate (0.22 g, 1.6 mmol) in dioxane (2.5 mL), ethanol (0.83 mL) and water (0.83 mL) was degassed and treated with Pd(dppf)$Cl_2$ (10.0 mg, 0.012 mmol), degassed again, and stirred at 80° C. for 2 h. The reaction mixture was diluted with $CH_2Cl_2$ and washed with water. The water layer was extracted with 2×$CH_2Cl_2$, dried ($Na_2SO_4$), and the solvent evaporated in vacuo. The crude product was purified by flash chromatography and preparatory TLC to afford compound 72 as a white powder (0.054 g; 32%). LCMS (ESI) m/z 425 (M+H)$^+$.

Example 12

Synthesis of Compounds 73 and 74

Scheme 16 illustrates the synthesis of compounds 73 and 74. Bromoketone 146 was subjected to alkylation with thioureas 147 and 148 to afford thiazoles 149 and 150 respectively. Coupling of 149 and 150 with boronate 123 yielded thiazoles 73 and 74.

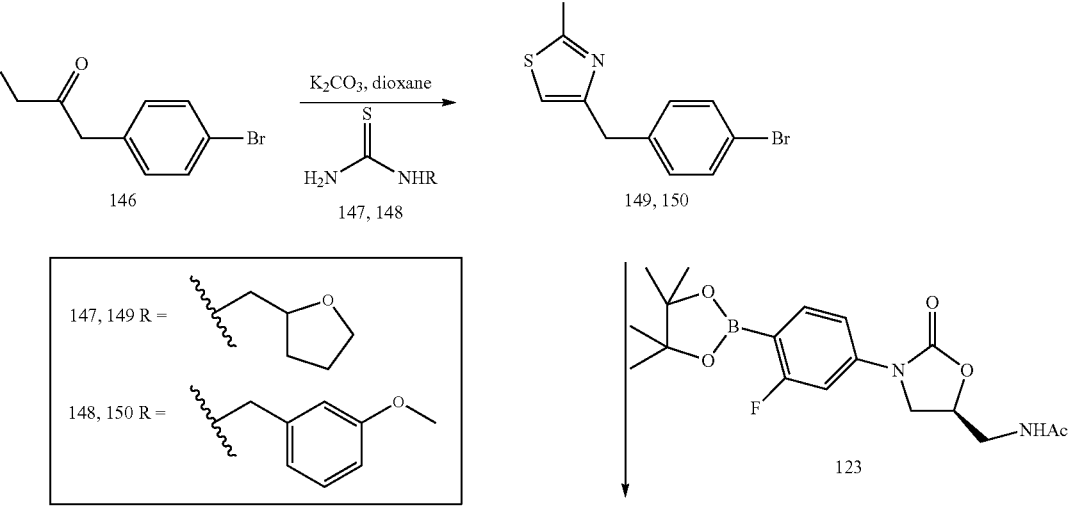

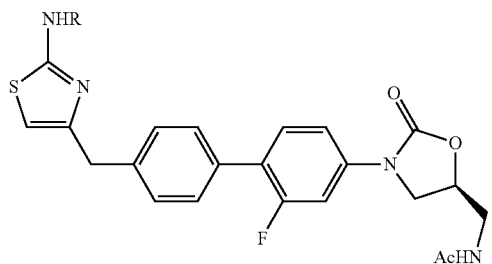

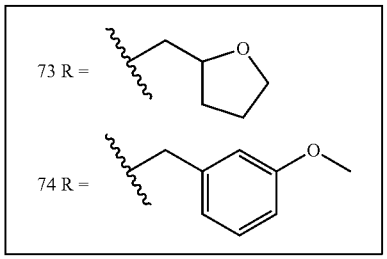

Synthesis of Compound 73

Bromoketone 146 (0.29 g, 1.0 mmol) was dissolved in dioxane (10 mL). Thiourea 147 (0.19 g, 1.2 mmol) and potassium carbonate (0.28 g, 2 mmol) were added sequentially and the resulting slurry stirred at 50° C. for 4 h. The mixture was cooled to room temperature, diluted with 100 mL CH$_2$Cl$_2$, and washed with saturated aqueous NaHCO$_3$ and brine. The aqueous washes were back-extracted with CH$_2$Cl$_2$ (2×50 mL). The combined organic extracts were dried over K$_2$CO$_3$, filtered, and concentrated in vacuo to afford bromide 149 as a yellow solid (0.32 g) which was used without further purification. LCMS (ESI) m/z 353 (M+H)$^+$.

The crude bromide 149 (0.20 g, 0.56 mmol), boronate ester 123 (0.25 g, 0.66 mmol), and K$_2$CO$_3$ (0.14 g, 1.0 mmol) were combined with a 1:1:1 mixture of toluene, ethanol and water (2 mL each). The slurry was degassed by alternately applying high vacuum to the reaction mixture and flushing with dry argon. The reaction vessel was then sealed and heated in an 80° C. oil bath for 14 h. The reaction mixture was cooled to room temperature, diluted with 100 mL 9:1 CH$_2$Cl$_2$/MeOH, and washed with water and brine (50 mL each). The aqueous washes were back-extracted once with 50 mL 9:1 CH$_2$Cl$_2$/MeOH. The combined organic extracts were dried over K$_2$CO$_3$, filtered, and concentrated in vacuo to afford 0.48 g of a brown solid. The solid was purified by flash column chromatography (7:3 acetone/hexane) to yield compound 73 as an off-white solid (0.17 g, 0.32 mmol). LCMS (ESI) m/z 525 (M+H)$^+$.

Synthesis of Compound 74

Compound 74 was synthesized according to the procedure described above for compound 73, using thiourea 148 in place of 147. The coupling reaction of bromide 150 and boronate 123 yielded compound 74 as a white solid (0.12 g, 0.21 mmol). LCMS (ESI) m/z 561 (M+H)$^+$.

Example 13

Synthesis of Compound 75

Scheme 17 depicts the synthesis of compound 75. D-p-Hydroxyphenyl-glycine 151 was converted to triflate 154, which was subsequently coupled to boronate 123 to afford alcohol 155. Mesylation of 155, followed by displacement with the anion of imidazole and deprotection of the BOC group yielded compound 75.

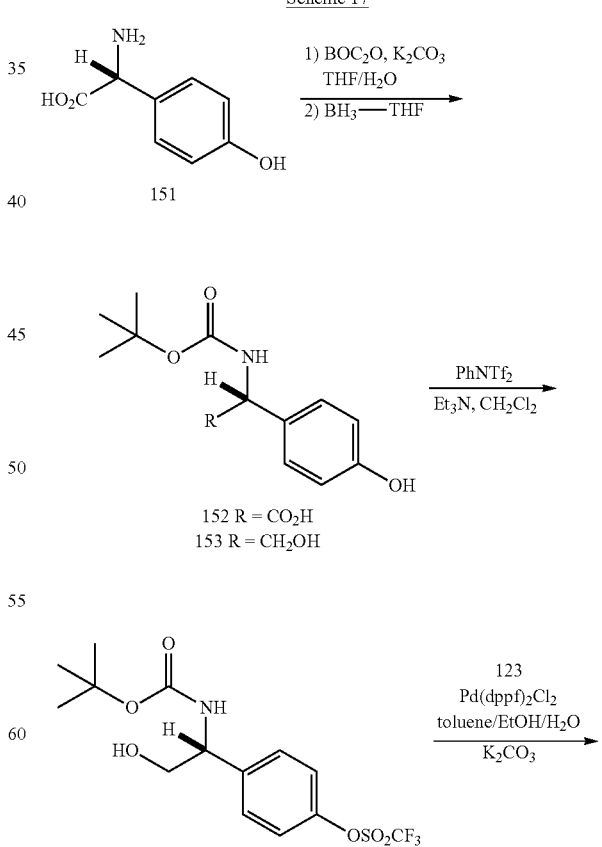

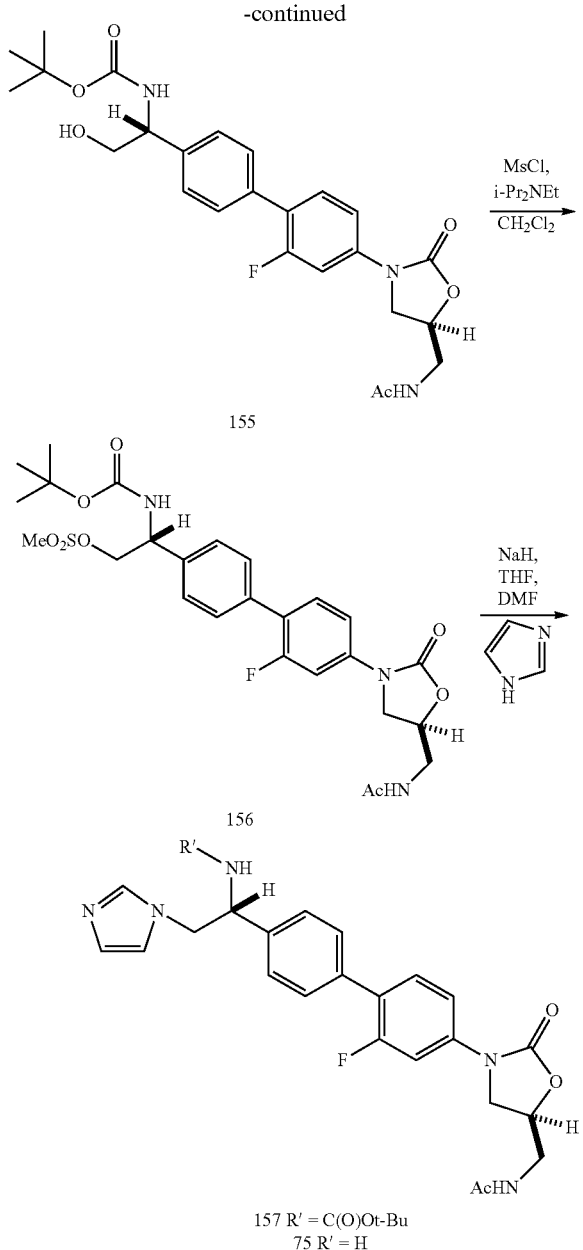

A solution of D-p-hydroxyphenylglycine 151 (23.8 g, 142.3 mmol) and potassium carbonate (39.3 g, 284.6 mmol) in THF (200 mL) and H₂O (200 mL) was treated with BOC₂O (34.14 g, 156.6 mmol) at 25° C., and the resulting reaction mixture was stirred at 25° C. for 2 h. When TLC and LCMS showed that the reaction was complete, the reaction mixture was treated with ethyl acetate (200 mL) and H₂O (200 mL). The two layers were separated, and the aqueous solution was extracted with ethyl acetate (200 mL). The aqueous layer was then acidified with a 2N aqueous HCl to pH 4 before being extracted with ethyl acetate (2×200 mL). The combined organic extracts were then washed with water (2×100 mL) and saturated aqueous NaCl (100 mL), dried over MgSO₄, and concentrated in vacuo. The residual white solids were further dried in vacuo to afford the crude desired acid 152 (36.5 g; 96%), which was of suitable purity for use in subsequent reactions.

A solution of acid 152 (4.005 g, 15 mmol) in anhydrous THF (20 mL) was treated dropwise with a 1 M solution of BH₃-THF in THF (30 mL, 30 mmol) at 0-5° C., and the resulting reaction mixture was stirred at 0-5° C. for an additional 2 h. When TLC and LCMS showed that the reduction reaction was complete, the reaction mixture was treated with water (50 mL) and ethyl acetate (50 mL). The mixture was then stirred at 25° C. for 30 min before being separated, and the aqueous layer was extracted with ethyl acetate (2×50 mL). The combined organic extracts were then washed with water (2×20 ml) and saturated aqueous NaCl (20 mL), dried over MgSO₄, and concentrated in vacuo. The residue was then directly purified by flash column chromatography (0-5% MeOH—CH₂Cl₂ gradient elution) to afford desired alcohol 153 (2.50 g; 66%) as a white powder which was of suitable purity for use in subsequent reactions.

A suspension alcohol 153 (670 mg, 2.65 mmol) in CH₂Cl₂ (10 mL) was treated with N-phenyltrifluoromethane sulfonamide (947 mg, 2.65 mmol) and triethylamine (535.3 mg, 0.74 mL, 5.3 mmol) at 25° C., and the resulting reaction mixture was stirred at 25° C. for an additional 2 h. When TLC and LCMS showed that the reaction was complete, the reaction mixture was quenched with water (10 mL) and CH₂Cl₂ (20 mL). The two layers were then separated, and the aqueous layer was extracted with CH₂Cl₂ (2×20 mL). The combined organic extracts were then washed with water (2×10 mL) and saturated aqueous NaCl (10 mL), dried over MgSO₄, and concentrated in vacuo. The residue was then directly purified by flash column chromatography (0-5% MeOH—CH₂Cl₂ gradient elution) to afford triflate 154 (945 mg; 93%) as a white powder which was of suitable purity for use in subsequent reactions.

A solution of boronate 123 (2.162 g, 5.72 mmol) and triflate 154 (1.70 g, 4.4 mmol) in toluene (24 mL) was treated with solid potassium carbonate (1.82 g, 13.2 mmol), ethanol (8.0 mL) and H₂O (8.0 mL) at room temperature, and the resulting reaction mixture was degassed three times under a steady stream of argon before being treated with Pd(dppf)₂Cl₂ (184 mg, 0.22 mmol) at room temperature. The reaction mixture was then degassed three times again under a steady stream of argon before being warmed to reflux for 2 h. When TLC and LCMS showed that the reaction was complete, the reaction mixture was cooled to room temperature before being treated with water (20 mL) and ethyl acetate (20 mL). The two layers were separated, and the aqueous layer was extracted with ethyl acetate (2×20 mL). The combined organic extracts were washed with water (2×20 mL) and saturated aqueous NaCl (20 mL), dried over MgSO₄, and concentrated in vacuo. The residue was then purified by flash column chromatography (0-5% MeOH—CH₂Cl₂ gradient elution) to afford (1-{4'-[5-(acetylamino-methyl)-2-oxo-oxazolidin-3-yl]-2'-fluoro-biphenyl-4-yl}-2-hydroxyethyl)carbamic acid tert-butyl ester 155 (1.543 g; 72%) as yellow oil, which solidified upon standing at room temperature in vacuo.

A suspension of alcohol 155 (694 mg, 1.43 mmol) in anhydrous CH₂Cl₂ (10 mL) was treated with diisopropylethylamine (388 mg, 0.522 mL, 2.85 mmol) and methanesulfonyl chloride (196 mg, 0.132 mL, 1.71 mmol) at 0-5° C., and the resulting reaction mixture was stirred at 0-5° C. for an additional 2 h. When TLC and LCMS showed that the reaction was complete, the reaction mixture was quenched with water (10 mL). The two layers were separated, and the aqueous layer was extracted with CH₂Cl₂ (2×10 mL). The combined organic extracts were washed with water (2×10 mL) and saturated aqueous NaCl (10 mL), dried over MgSO₄, and concentrated in vacuo. The residue was then purified by flash column chromatography (0-5% MeOH—CH₂Cl₂ gradient elution) to afford mesylate 156 (647 mg; 80%) as a pale-yellow solid, which was of suitable purity for use in subsequent reactions.

A solution of imidazole (41 mg, 0.6 mmol) in anhydrous THF (3 mL) was treated with sodium hydride (NaH, 60% oil dispersion, 29 mg, 0.72 mmol) at 0° C., and the resulting mixture was stirred at 0-5° C. for 30 min before a solution of mesylate 156 (170 mg, 0.3 mmol) in anhydrous DMF (3.0 mL) was added. The resulting reaction mixture was then stirred at 0-5° C. for 30 min before being gradually warmed to room temperature for 12 h. When TLC and LCMS showed that the reaction was complete, the solvents were removed in vacuo, and the residue was directly purified by flash column chromatography (0-5% MeOH—CH$_2$Cl$_2$ gradient elution) to afford imidazole 157 (46 mg; 29%) as a yellow solid.

A solution of imidazole 157 (23 mg, 0.043 mmol) in MeOH (1.0 mL) was treated with 4N HCl in 1,4-dioxane (3.0 mL), and the resulting reaction mixture was stirred at room temperature for 30 min. When TLC and LCMS showed that the reaction was complete, the solvents were removed in vacuo, and the desired N-{3-[4'-(1-amino-2-imidazol-1-yl-ethyl)-2-fluoro-biphenyl-4-yl]-2-oxo-oxazolidin-5-ylm-ethyl]acetamide hydrochloride 75 (18.8 mg; 100%) was obtained as a yellow solid. LCMS (ESI) m/z 438 (M+H)$^+$.

Example 14

Synthesis of Compound 76

Scheme 18 depicts the synthesis of compound 76. Iodide 158 was converted to boronate 159, which was coupled to bromide 160 to afford tetrazole 161. Deprotection of 161 afforded compound 76.

Synthesis of Boronate 160

A solution of known 5-aminomethyl-3-(3-fluoro-4-iodo-phenyl)-oxazolidin-2-one (2.02 g, 6.0 mmol; see U.S. Pat. Nos. 5,523,403 and 5,565,571) and potassium carbonate (1.66 g, 12.0 mmol) in THF (20 mL) and H$_2$O (20 mL) was treated with BOC$_2$O (1.334 g, 6.12 mmol) at 25° C., and the resulting reaction mixture was stirred at 25° C. for 2 h. When TLC and LCMS showed the reaction was complete, the reaction mixture was treated with ethyl acetate (20 mL) and H$_2$O (20 mL). The two layers were separated, and the aqueous solution was extracted with ethyl acetate (20 mL), and the combined organic extracts were then washed with water (2×10 mL) and saturated aqueous NaCl (10 mL), dried over MgSO$_4$, and concentrated in vacuo. The residual white solids were further dried in vacuo to afford the crude, desired iodide 158 (2.40 g; 92%), which was of suitable purity for use in subsequent reactions.

A solution of iodide 158 (1.11 g, 2.55 mmol) in 1,4-diox-ane (25 mL) was treated with 4,4,5,5-tetramethyl-[1,3,2]di-oxaborolane 159 (489 mg, 0.56 mL, 3.82 mmol) and triethy-lamine (772 mg, 1.07 mL, 7.65 mmol) at room temperature, and the resulting reaction mixture was degassed three times under a steady stream of argon before being treated with Pd(dppf)$_2$Cl$_2$ (107 mg, 0.13 mmol) at room temperature. The reaction mixture was then degassed three times again under a steady stream of argon before being warmed to reflux for 6 h. When TLC and LCMS showed that the reaction was com-plete, the reaction mixture was cooled to room temperature before being treated with water (20 mL) and ethyl acetate (20

Scheme 18

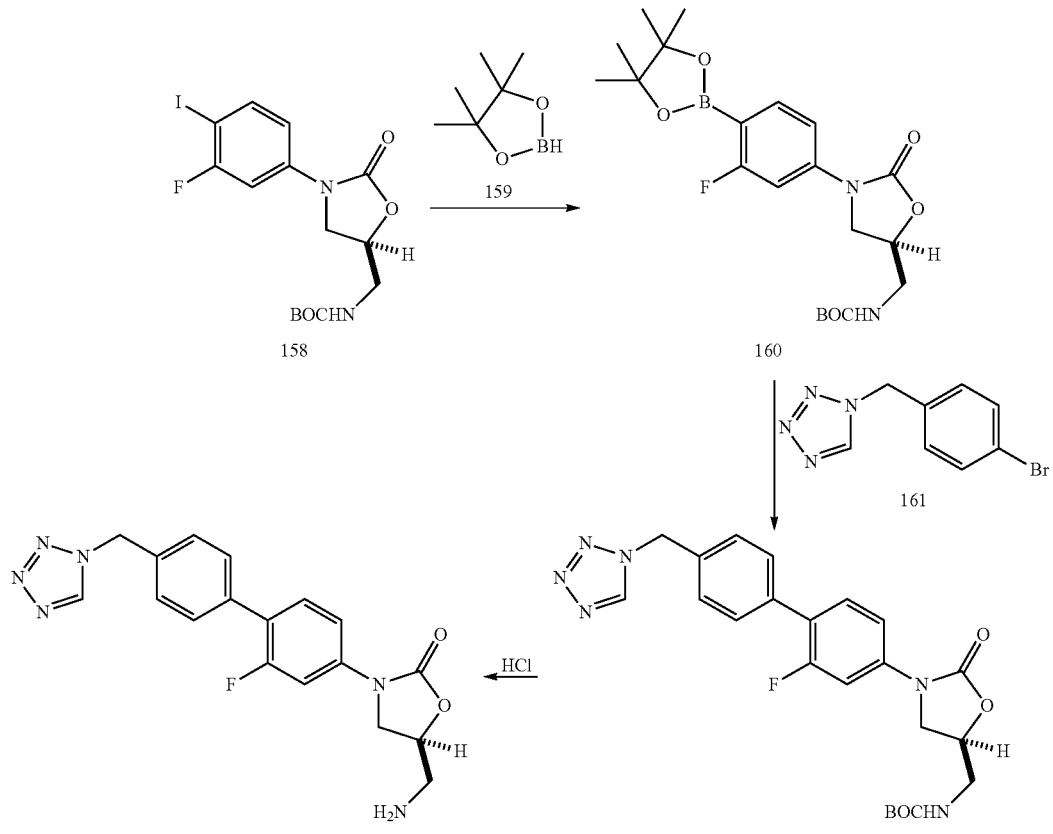

mL). The two layers were separated, and the aqueous layer was extracted with ethyl acetate (2×20 mL). The combined organic extracts were washed with water (2×20 mL) and saturated aqueous NaCl (20 mL), dried over MgSO$_4$, and concentrated in vacuo. The residual brown oil was then purified by flash column chromatography (10-30% EtOAc-hexanes gradient elution) to afford boronate 160 (646 mg; 58%) as a brown oil that solidified upon standing at room temperature in vacuo. The product was of suitable purity for use in subsequent reactions.

Synthesis of Bromide 161

A solution of 4-bromobenzylamine hydrochloride (2.22 g, 10.0 mmol) in acetic acid (30 mL) was treated with triethyl orthoformate (2.964 g, 3.29 mL, 20.0 mmol) and sodium azide (NaN$_3$, 2.30 g, 20.0 mmol) at room temperature, and the resulting reaction mixture was subsequently stirred at reflux for 12 h. When TLC and LCMS showed that the reaction was complete, the reaction mixture was cooled to room temperature, and the cooled reaction mixture was poured into ice water (100 mL). The precipitate was then collected by filtration, washed with water (2×20 mL), and dried in vacuo to afford bromide 161 (460 mg; 19%) as a white solid which was of suitable purity for use in subsequent reactions.

Synthesis of Compound 76

A solution of boronate 160 (658 mg, 1.5 mmol) and bromide 161 (300 mg, 1.25 mmol) in toluene (9.0 mL) was treated with solid potassium carbonate (621 mg, 4.5 mmol), ethanol (3.0 mL) and H$_2$O (3.0 mL) at room temperature, and the resulting reaction mixture was degassed three times under a steady stream of argon before being treated with Pd(dppf)$_2$Cl$_2$ (52.3 mg, 0.063 mmol) at room temperature. The reaction mixture was then degassed three times again under a steady stream of argon before being warmed to reflux for 3 h. When TLC and LCMS showed that the reaction was complete, the reaction mixture was cooled to room temperature before being treated with water (10 mL) and ethyl acetate (20 mL). The two layers were separated, and the aqueous layer was extracted with ethyl acetate (2×10 mL). The combined organic extracts were washed with water (2×5 mL) and saturated aqueous NaCl (5 mL), dried over MgSO$_4$, and concentrated in vacuo. The residue was then purified by flash column chromatography (0-5% MeOH—CH$_2$Cl$_2$ gradient elution) to afford tetrazole 162 (357 mg; 61%) as a yellow oil, which solidified upon standing at room temperature in vacuo.

A solution of tetrazole 162 (350 mg, 0.748 mmol) in EtOAc (5.0 mL) was treated with 4N HCl in 1,4-dioxane (5.0 mL), and the resulting reaction mixture was stirred at room temperature for 30 min. When TLC and LCMS showed that the reaction was complete, the solvents were removed in vacuo, and the residue was treated with aqueous sodium bicarbonate (10 mL) and EtOAc (15 mL). The mixture was stirred at room temperature for 30 min before the two layers were separated. The aqueous layer was extracted with EtOAc (10 mL), and the combined organic extracts were washed with H$_2$O (10 mL) and saturated aqueous NaCl (10 mL), dried over MgSO$_4$, and concentrated in vacuo to afford compound 76 (266 mg; 97%) as a pale-yellow solid. LCMS (ESI) m/z 369 (M+H)$^+$.

Example 15

Synthesis of Compounds 77-79

Scheme 19 depicts the synthesis of aryl bromides 163-165 required for the synthesis of compounds 77-79. Epoxide 139 was treated with 1-formyl piperazine to afford a mixture of bromides 163 and 164. Epoxide ring-opening of 139 with imidazole afforded bromide 165. These bromides were coupled with boronate 123 to afford the target compounds 77-79.

Scheme 19

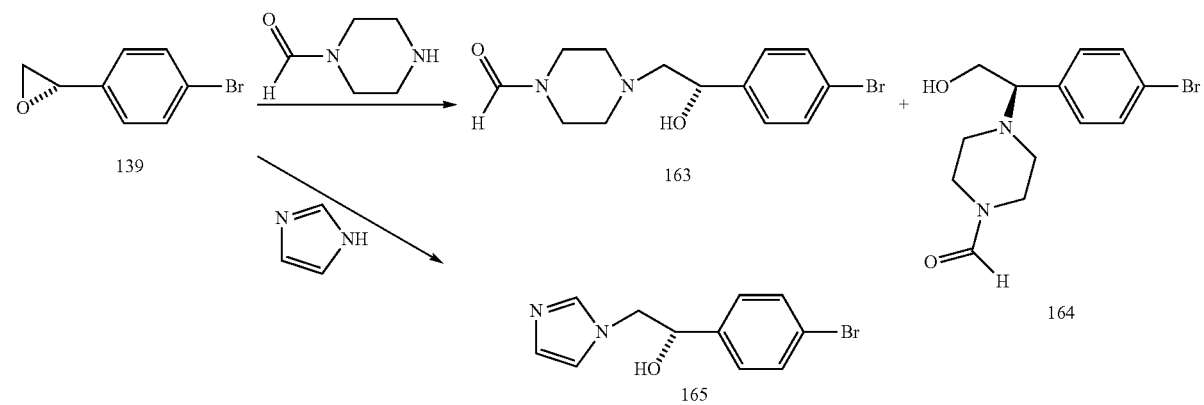

Synthesis of Bromides 163 and 164

To a suspension of epoxide 139 (1 mmol, 1 eq) in acetonitrile (3.0 mL) at room temperature was added LiClO$_4$ (1.05 mmol, 1.05 eq). After the formation of a clear solution, 1-formyl piperazine (1.5 mmol, 1.5 eq) was added. The mixture was stirred at room temperature for 16 h. The solvent was removed in vacuo and the residue was purified by flash chromatography (3:100 MeOH/CH$_2$Cl$_2$) to yield 132 mg of bromide 163 and 42 mg of bromide 164.

Synthesis of Compound 77

A suspension of bromide 163 (1 eq), boronate 123 (1 eq), PdCl$_2$(dppf)$_2$ (0.05 eq), and K$_2$CO$_3$ (4 eq) in a 3:1:1 mixture of dioxane/EtOH/H$_2$O was degassed by a stream of argon. The mixture was stirred at 80° C. for 3.5 h. The solvent was removed in vacuo and the residue was purified by flash chromatography (4:100 MeOH/CH$_2$Cl$_2$) to afford 150 mg compound 77. LCMS (ESI) m/z 485 (M+H)$^+$.

Synthesis of Compound 78

A suspension of bromide 164 (1 eq), boronate 123 (1 eq), PdCl$_2$(dppf)$_2$ (0.05 eq), and K$_2$CO$_3$ (4 eq) in a 3:1:1 mixture of dioxane/EtOH/H$_2$O was degassed by a stream of argon. The mixture was stirred at 80° C. for 3.5 h. The solvent was removed in vacuo and the residue was purified by flash chromatography (5:100 MeOH/CH$_2$Cl$_2$) to afford 52 mg compound 78. LCMS (ESI) m/z 485 (M+H)$^+$.

Synthesis of Bromide 165

To a suspension of epoxide 139 (1 mmol, 1 eq) in acetonitrile (3.0 mL) at room temperature was added LiClO$_4$ (1.05 mmol, 1.05 eq). After the formation of a clear solution, imidazole (1.5 mmol, 1.5 eq) was added. The mixture was stirred at 60° C. for 4 h. The solvent was removed in vacuo and the residue was purified by flash chromatography (3:100 MeOH/CH$_2$Cl$_2$) to yield 103 mg of bromide 165.

Synthesis of Compound 79

A suspension of bromide 165 (1 eq), boronate 123 (1 eq), PdCl$_2$(dppf)$_2$ (0.05 eq), and K$_2$CO$_3$ (4 eq) in a 3:1:1 mixture of dioxane/EtOH/H$_2$O was degassed by a stream of argon. The mixture was stirred at 80° C. for 2.5 h. The solvent was removed in vacuo and the residue was purified by flash chromatography (10:100 MeOH/CH$_2$Cl$_2$) to afford 155 mg compound 79. LCMS (ESI) m/z 439 (M+H)$^+$.

The entire disclosure of each of the patent documents and scientific articles referred to herein is incorporated by reference for all purposes.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A process for preparing a compound having the formula:

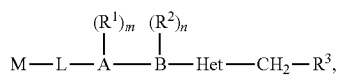

the process comprising the steps of:
combining a compound of formula (I):

(I)

with a compound of formula (II):

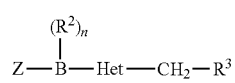

(II)

in a solvent in the presence of a base and a palladium catalyst, wherein

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het-CH$_2$—R$^3$ is selected from the group consisting of:

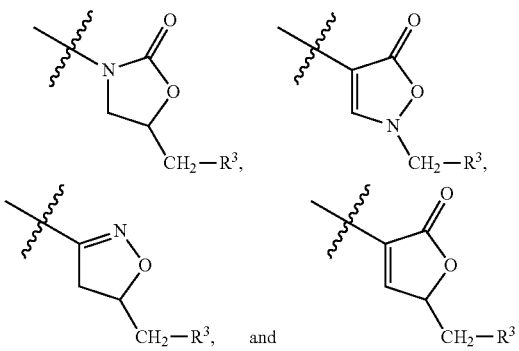

M-L is selected from the group consisting of:
a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X—X—, i) M-L$^1$-X—X—, j) M-X—X-L$^2$, and k) M-L$^1$-X—X-L$^2$, wherein
X, at each occurrence, independently is selected from the group consisting of:
a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N=, i) =N—NR$^4$—, j) —O—N=, k) =N—O—, l) —N=, m) =N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and

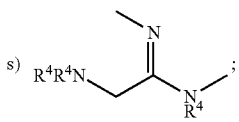

L$^1$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups; and
L$^2$ is selected from the group consisting of:
a) C$_{1-6}$ alkyl, b) C$_{2-6}$ alkenyl, and c) C$_{2-6}$ alkynyl, wherein any of a)-c) optionally is substituted with one or more R$^5$ groups;
alternatively, L in M-L is a bond;
M is selected from the group consisting of:
a) C$_{3-14}$ saturated, unsaturated, or aromatic carbocycle, b) 3-14 membered saturated, unsaturated, or aromatic heterocycle containing one or more heteroatoms selected from the group consisting of nitrogen, oxygen, and sulfur, c) C$_{1-6}$ alkyl, d) C$_{2-6}$ alkenyl, e) C$_{2-6}$ alkynyl, and f) —CN,
wherein any of a)-e) optionally is substituted with one or more R$^5$ groups;
Q is a borane having the formula —BY$_2$, wherein
Y, at each occurrence, independently is selected from the group consisting of:
a) —OH, b) —OC$_{1-6}$ alkyl, c) —OC$_{2-6}$ alkenyl, d) —OC$_{2-6}$ alkynyl, e) —OC$_{1-14}$ saturated, unsaturated, or aromatic carbocycle, f) C$_{1-6}$ alkyl, g) C$_{2-6}$ alkenyl, h) C$_{2-6}$ alkynyl, and i) C$_{1-14}$ saturated, unsaturated, or aromatic carbocycle,
wherein any of b)-i) optionally is substituted with one or more halogens;

alternatively, two Y groups taken together comprise a chemical moiety selected from the group consisting of:
  a) —OC($R^4$)($R^4$)C($R^4$)($R^4$)O—, and b) —OC($R^4$)($R^4$)CH$_2$C($R^4$)($R^4$)O—;
alternatively, Q is a BF$_3$ alkali metal salt or 9-borabicyclo[3.3.1]nonane;

Z is selected from the group consisting of:
  a) I, b) Br, c) Cl, and d) $R^9SO_3$—;

$R^1$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —C(NR$^4$)R$^4$, aa) —C(NR$^4$)OR$^4$, bb) —OC(NR$^4$)R$^4$, cc) —C(NR$^4$)NR$^4$R$^4$, dd) —NR$^4$C(NR$^4$)R$^4$, ee) —OC(NR$^4$)NR$^4$R$^4$, ff) —NR$^4$C(NR$^4$)OR$^4$, gg) —NR$^4$C(NR$^4$)NR$^4$R$^4$, hh) —S(O)$_p$R$^4$, ii) —SO$_2$NR$^4$R$^4$, and jj) R$^4$;

$R^2$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —C(NR$^4$)R$^4$, aa) —C(NR$^4$)OR$^4$, bb) —OC(NR$^4$)R$^4$, cc) —C(NR$^4$)NR$^4$R$^4$, dd) —NR$^4$C(NR$^4$)R$^4$, ee) —OC(NR$^4$)NR$^4$R$^4$, ff) —NR$^4$C(NR$^4$)OR$^4$, gg) —NR$^4$C(NR$^4$)NR$^4$R$^4$, hh) —S(O)$_p$R$^4$, ii) —SO$_2$NR$^4$R$^4$, and jj) R$^4$;

$R^3$ is selected from the group consisting of:
  a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h) —OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q) —NR$^4$C(S)OR$^4$, r) —NR$^4$C(S)NR$^4$R$^4$, s) —C(NR$^4$)R$^4$, t) —C(NR$^4$)OR$^4$, u) —OC(NR$^4$)R$^4$, v) —C(NR$^4$)NR$^4$R$^4$, w) —NR$^4$C(NR$^4$)R$^4$, x) —OC(NR$^4$)NR$^4$R$^4$, y) —NR$^4$C(NR$^4$)OR$^4$, z) —NR$^4$C(NR$^4$)NR$^4$R$^4$, aa) —S(O)$_p$R$^4$, bb) —SO$_2$NR$^4$R$^4$, and cc) R$^4$;

$R^4$, at each occurrence, independently is selected from the group consisting of:
  a) H, b) —OR$^6$, c) an amine protecting group, d) $C_{1-6}$ alkyl, e) $C_{2-6}$ alkenyl, f) $C_{2-6}$ alkynyl, g) $C_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—$C_{1-6}$ alkyl, j) —C(O)—$C_{2-6}$ alkenyl, k) —C(O)—$C_{2-6}$ alkynyl, l) —C(O)—$C_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—$C_{1-6}$ alkyl, o) —C(O)O—$C_{2-6}$ alkenyl, p) —C(O)O—$C_{2-6}$ alkynyl, q) —C(O)O—$C_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur,
  wherein any of d)-r) optionally is substituted with one or more $R^5$ groups;

$R^5$, at each occurrence, is independently selected from the group consisting of:
  a) F, b) Cl, c) Br, d) I, e) =O, f) =S, g) =NR$^6$, h) =NOR$^6$, i) =N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —C(NR$^6$)R$^6$, ff) —C(NR$^6$)OR$^6$, gg) —OC(NR$^6$)R$^6$, hh) —C(NR$^6$)NR$^6$R$^6$, ii) —NR$^6$C(NR$^6$)R$^6$, jj) —OC(NR$^6$)NR$^6$R$^6$, kk) —NR$^6$C(NR$^6$)OR$^6$, ll) —NR$^6$C(NR$^6$)NR$^6$R$^6$, mm) —S(O)$_p$R$^6$, nn) —SO$_2$NR$^6$R$^6$, and oo) R$^6$;

$R^6$, at each occurrence, independently is selected from the group consisting of:
  a) H, b) —OR$^8$, c) an amine protecting group, d) $C_{1-6}$ alkyl, e) $C_{2-6}$ alkenyl, f) $C_{2-6}$ alkynyl, g) $C_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—$C_{1-6}$ alkyl, j) —C(O)—$C_{2-6}$ alkenyl, k) —C(O)—$C_{2-6}$ alkynyl, l) —C(O)—$C_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—$C_{1-6}$ alkyl, o) —C(O)O—$C_{2-6}$ alkenyl, p) —C(O)O—$C_{2-6}$ alkynyl, q) —C(O)O—$C_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur,
  wherein any of d)-r) optionally is substituted with one or more $R^7$ groups;

$R^7$, at each occurrence, independently is selected from the group consisting of:
  a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —C(NR$^8$)R$^8$, ff) —C(NR$^8$)OR$^8$, gg) —OC(NR$^8$)R$^8$, hh) —C(NR$^8$)NR$^8$R$^8$, ii) —NR$^8$C(NR$^8$)R$^8$, jj) —OC(NR$^8$)NR$^8$R$^8$, kk) —NR$^8$C(NR$^8$)OR$^8$, ll) —NR$^8$C(NR$^8$)NR$^8$R$^8$, mm) —S(O)$_p$R$^8$, nn) —SO$_2$NR$^8$R$^8$, oo) $C_{1-6}$ alkyl, pp) $C_{2-6}$ alkenyl, qq) $C_{2-6}$ alkynyl, rr) $C_{3-14}$ saturated, unsaturated, or aromatic carbocycle, and ss) 3-14 membered saturated, unsaturated, or aromatic heterocycle comprising one or more heteroatoms selected from the group consisting of nitrogen, oxygen, and sulfur,
  wherein any of oo)-ss) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S)NR$^8$R$^8$, —C(NR$^8$)R$^8$, —C(NR$^8$)OR$^8$, —OC(NR$^8$)R$^8$, —C(NR$^8$)NR$^8$R$^8$, —NR$^8$C(NR$^8$)R$^8$, —OC(NR$^8$)NR$^8$R$^8$, —NR$^8$C(NR$^8$)OR$^8$, —NR$^8$C(NR$^8$)NR$^8$R$^8$, —SO$_2$NR$^8$R$^8$, and —S(O)$_p$R$^8$;

R$^8$, at each occurrence, independently is selected from the group consisting of:

a) H, b) an amine protecting group, c) C$_{1-6}$ alkyl, d) C$_{2-6}$ alkenyl, e) C$_{2-6}$ alkynyl, f) C$_{3-14}$ saturated, unsaturated, or aromatic carbocycle, g) 3-14 membered saturated, unsaturated, or aromatic heterocycle comprising one or more heteroatoms selected from the group consisting of nitrogen, oxygen, and sulfur, h) —C(O)—C$_{1-6}$ alkyl, i) —C(O)—C$_{2-6}$ alkenyl, j) —C(O)—C$_{2-6}$ alkynyl, k) —C(O)—C$_{3-14}$ saturated, unsaturated, or aromatic carbocycle, l) —C(O)-3-14 membered saturated, unsaturated, or aromatic heterocycle comprising one or more heteroatoms selected from the group consisting of nitrogen, oxygen, and sulfur, m) —C(O)O—C$_{1-6}$ alkyl, n) —C(O)O—C$_{2-6}$ alkenyl, o) —C(O)O—C$_{2-6}$ alkynyl, p) —C(O)O—C$_{3-14}$ saturated, unsaturated, or aromatic carbocycle, and q) —C(O)O-3-14 membered saturated, unsaturated, or aromatic heterocycle comprising one or more heteroatoms selected from the group consisting of nitrogen, oxygen, and sulfur, wherein any of c)-q) optionally is substituted with one or more moieties selected from the group consisting of F, Cl, Br, I, —CF$_3$, —OH, —OC$_{1-6}$ alkyl, —SH, —SC$_{1-6}$ alkyl, —CN, —NO$_2$, —NH$_2$, —NHC$_{1-6}$ alkyl, -N(C$_{1-6}$ alkyl)$_2$, —C(O)C$_{1-6}$ alkyl, —C(O)OC$_{1-6}$ alkyl, —C(O)NH$_2$, —C(O)NHC$_{1-6}$ alkyl, —C(O)N(C$_{1-6}$ alkyl)$_2$, —NHC(O)C$_{1-6}$ alkyl, —SO$_2$NH$_2$—, —SO$_2$NHC$_{1-6}$ alkyl, —SO$_2$N(C$_{1-6}$ alkyl)$_2$, and —S(O)$_p$C$_{1-6}$ alkyl;

R$^9$ is selected from the group consisting of:

a) C$_{1-6}$ alkyl, b) phenyl, and c) toluoyl;

wherein any of a)-c) optionally is substituted with one or more moieties selected from the group consisting of F, Cl, Br, and I;

m is 0, 1, 2, 3, or 4;

n is 0, 1, 2, 3, or 4; and p, at each occurrence, independently is 0, 1, or 2.

2. The process according to claim 1, wherein the compound of formula (II) has the formula:

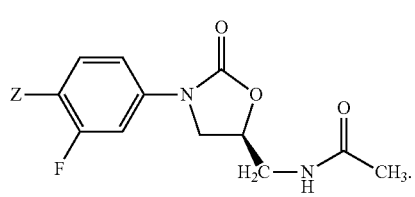

(II)

3. The process according to claim 1, wherein the compound of formula (II) has the formula:

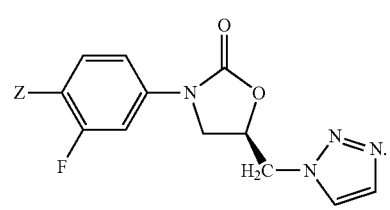

(II)

4. The process according to claim 1, wherein the compound of formula (I) has the formula:

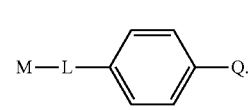

(I)

5. The process according to claim 1, wherein M-L is M-CH$_2$—X—CH$_2$—.

6. The process according to claim 5, wherein X is —NR$^4$—.

7. The process according to claim 6, wherein R$^4$ is H.

8. The process according to claim 6, wherein R$^4$ is an amine protecting group.

9. The process according to claim 8, wherein the amine protecting group is selected from the group consisting of:

a) benzyl, b) t-butyldimethylsilyl, c) t-butdyldiphenylsilyl, d) t-butyloxycarbonyl, e) p-methoxybenzyl, f) methoxymethyl, g) tosyl, h) trifluoroacetyl, i) trimethylsilyl, j) fluorenyl-methyloxycarbonyl, k) 2-trimethylsilylethyoxycarbonyl, l) 1-methyl-1-(4-biphenylyl)ethoxycarbonyl, m) allyloxycarbonyl, and n) benzyloxycarbonyl.

10. The process according to claim 8, further comprising the step of removing the amine protecting group.

11. The process according to claim 5, wherein M comprises a 5-6 membered saturated, unsaturated, or aromatic heterocycle comprising one or more heteroatoms selected from the group consisting of nitrogen, oxygen, and sulfur.

12. The process according to claim 11, wherein M is selected from the group consisting of triazole, tetrazole, oxazole, and isoxazole.

13. The process according to claim 12, wherein M is [1,2,3]triazol-4-yl.

14. The process according to claim 1, wherein M-L is M-X—CH$_2$—.

15. The process according to claim 14, wherein X is —NR$^4$—.

16. The process according to claim 15, wherein R$^4$ is H.

17. The process according to claim 15, wherein R$^4$ is an amine protecting group.

18. The process according to claim 17, wherein the amine protecting group is selected from the group consisting of:

a) benzyl, b) t-butyldimethylsilyl, c) t-butdyldiphenylsilyl, d) t-butyloxycarbonyl, e) p-methoxybenzyl, f) methoxymethyl, g) tosyl, h) trifluoroacetyl, i) trimethylsilyl, j) fluorenyl-methyloxycarbonyl, k) 2-trimethylsilylethyoxycarbonyl, l) 1-methyl-1-(4-biphenylyl)ethoxycarbonyl, m) allyloxycarbonyl, and n) benzyloxycarbonyl.

19. The process according to claim 14, wherein M is selected from the group consisting of:

a) C$_{1-6}$ alkyl, b) C$_{2-6}$ alkenyl, c) C$_{2-6}$ alkynyl, and d) —CN, wherein
i) any of a)-c) is substituted with one or more moieties selected from the group consisting of F, Cl, Br, I, and —CN; and
ii) any of a)-c) optionally is further substituted with one or more R⁵ groups.

20. A process for preparing a compound having the formula:

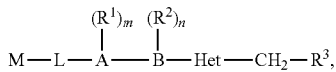

the process comprising the steps of:
combining a compound of formula (I):

(I)

with a compound of formula (II):

(II)

in a solvent in the presence of a base and a palladium catalyst, wherein
A is selected from the group consisting of:
phenyl, pyridyl, pyrazinyl, pyrimidinyl, and pyridazinyl;
B is selected from the group consisting of:
phenyl, pyridyl, pyrazinyl, pyrimidinyl, and pyridazinyl;
Het-CH₂—R³ is selected from the group consisting of:

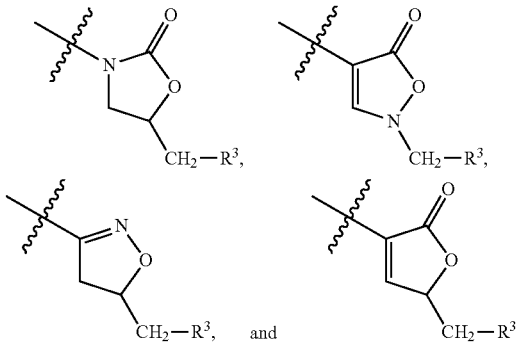

M-L is selected from the group consisting of:
a) M-X, b) M-L¹, c) M-L¹-X, d) M-X-L², e) M-L¹-X-L², f) M-X-L¹-X-L², g) M-L¹-X-L²-X, h) M-X—X—, i) M-L¹-X—X—, j) M-X—X-L², and k) M-L¹-X—X-L², wherein
X, at each occurrence, independently is selected from the group consisting of:
a) —O—, b) —NR⁴—, c) —N(O)13, d) —N(OR⁴)—, e) —S(O)$_p$—, f) —SO₂NR⁴—, g) —NR⁴SO₂—, h) —NR⁴—N=, i) =N—NR⁴—, j) —O—N=, k) =N—O—, l) —N=, m) =N—, n) —NR⁴—NR⁴—, o) —NR⁴C(O)O—, p) —OC(O)NR⁴—, q) —NR⁴C(O)NR⁴— r) —NR⁴C(NR⁴)NR⁴—, and s) 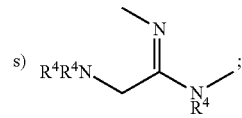;

L¹ is selected from the group consisting of:
a) C$_{1-6}$ alkyl, b) C$_{2-6}$ alkenyl, and c) C$_{2-6}$ alkynyl, wherein any of a)-c) optionally is substituted with one or more R⁵ groups; and
L² is selected from the group consisting of:
a) C$_{1-6}$ alkyl, b) C$_{2-6}$ alkenyl, and c) C$_{2-6}$ alkynyl, wherein any of a)-c) optionally is substituted with one or more R⁵ groups;
alternatively, L in M-L is a bond;
M is selected from the group consisting of:
a) C$_{3-14}$ saturated, unsaturated, or aromatic carbocycle, b) 3-14 membered saturated, unsaturated, or aromatic heterocycle containing one or more heteroatoms selected from the group consisting of nitrogen, oxygen, and sulfur, c) C$_{1-6}$ alkyl, d) C$_{2-6}$ alkenyl, e) C$_{2-6}$ alkynyl, and f) —CN,
wherein any of a)-e) optionally is substituted with one or more R⁵ groups;
Q is a borane having the formula —BY₂, wherein
Y, at each occurrence, independently is selected from the group consisting of:
a) —OH, b) —OC$_{1-6}$ alkyl, c) —OC$_{2-6}$ alkenyl, d) —OC$_{2-6}$ alkynyl, e) —OC$_{1-14}$ saturated, unsaturated, or aromatic carbocycle, f) C$_{1-6}$ alkyl, g) C$_{2-6}$ alkenyl, h) C$_{2-6}$ alkynyl, and i) C$_{1-14}$ saturated, unsaturated, or aromatic carbocycle,
wherein any of b)-i) optionally is substituted with one or more halogens;
alternatively, two Y groups taken together comprise a chemical moiety selected from the group consisting of:
a) —OC(R⁴)(R⁴)C(R⁴)(R⁴)O—, and b) —OC(R⁴)(R⁴)CH₂C(R⁴)(R⁴)O—;
alternatively, Q is a BF₃ alkali metal salt or 9-borabicyclo[3.3.1]nonane;
Z is selected from the group consisting of:
a) I, b) Br, c) Cl, and d) R⁹SO₃—;
R¹, at each occurrence, independently is selected from the group consisting of:
a) F, b) Cl, c) Br, d) I, e) —CF₃, f) —OR⁴, g) —CN, h) —NO₂, i) —NR⁴R⁴, j) —C(O)R⁴, k) —C(O)OR⁴, l) —OC(O)R⁴, m) —C(O)NR⁴R⁴, n) —NR⁴C(O)R⁴, o) —OC(O)NR⁴R⁴, p) —NR⁴C(O)OR⁴, q) —NR⁴C(O)NR⁴R⁴, r) —C(S)R⁴, s) —C(S)OR⁴, t) —OC(S)R⁴, u) —C(S)NR⁴R⁴, v) —NR⁴C(S)R⁴, w) —OC(S)NR⁴R⁴, x) —NR⁴C(S)OR⁴, y) —NR⁴C(S)NR⁴R⁴, z) —C(NR⁴)R⁴, aa) —C(NR⁴)OR⁴, bb) —OC(NR⁴)R⁴, cc) —C(NR⁴)NR⁴R⁴, dd) —NR⁴C(NR⁴)R⁴, ee) —OC(NR⁴)NR⁴R⁴, ff) —NR⁴C(NR⁴)OR⁴, gg) —NR⁴C(NR⁴)NR⁴R⁴, hh) —S(O)$_p$R⁴, ii) —SO₂NR⁴R⁴, and jj) R⁴;
R², at each occurrence, independently is selected from the group consisting of:

a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)O R$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —C(NR$^4$)R$^4$, aa) —C(NR$^4$)OR$^4$, bb) —OC(NR$^4$)R$^4$, cc) —C(NR$^4$)NR$^4$R$^4$, dd) —NR$^4$C(NR$^4$)R$^4$, ee) —OC(NR$^4$)NR$^4$R$^4$, ff) —NR$^4$C(NR$^4$)OR$^4$, gg) —NR$^4$C(NR$^4$)NR$^4$R$^4$, hh) —S(O)$_p$R$^4$, ii) —SO$_2$NR$^4$R$^4$, and jj) R$^4$;

R$^3$ is selected from the group consisting of:
  a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h) —OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q) —NR$^4$C(S)OR$^4$, r) —NR$^4$C(S)NR$^4$R$^4$, s) —C(NR$^4$)R$^4$, t) —C(NR$^4$)OR$^4$, u) —OC(NR$^4$)R$^4$, v) —C(NR$^4$)NR$^4$R$^4$, w) —NR$^4$C(NR$^4$)R$^4$, x) —OC(NR$^4$)NR$^4$R$^4$, y) —NR$^4$C(NR$^4$)OR$^4$, z) —NR$^4$C(NR$^4$)NR$^4$R$^4$, aa) —S(O)$_p$R$^4$, bb) —SO$_2$NR$^4$R$^4$, and cc) R$^4$;

R$^4$, at each occurrence, independently is selected from the group consisting of:
  a) H, b) —OR$^6$, c) an amine protecting group, d) C$_{1-6}$ alkyl, e) C$_{2-6}$ alkenyl, f) C$_{2-6}$ alkynyl, g) C$_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—C$_{1-6}$ alkyl, j) —C(O)—C$_{2-6}$ alkenyl, k) —C(O)—C$_{2-6}$ alkynyl, l) —C(O)—C$_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—C$_{1-6}$ alkyl, o) —C(O)O—C$_{2-6}$ alkenyl, p) —C(O)O—C$_{2-6}$ alkynyl, q) —C(O)O—C$_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur,
    wherein any of d)-r) optionally is substituted with one or more R$^5$ groups;

R$^5$, at each occurrence, is independently selected from the group consisting of:
  a) F, b) Cl, c) Br, d) I, e) =O, f) =S, g) =NR$^6$, h) =NOR$^6$, i) =N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —C(NR$^6$)R$^6$, ff) —C(NR$^6$)OR$^6$, gg) —OC(NR$^6$)R$^6$, hh) —C(NR$^6$)NR$^6$R$^6$, ii) —NR$^6$C(NR$^6$)R$^6$, jj) —OC(NR$^6$)NR$^6$R$^6$, kk) —NR$^6$C(NR$^6$)OR$^6$, ll) —NR$^6$C(NR$^6$)NR$^6$R$^6$, mm) —S(O)$_p$R$^6$, nn) —SO$_2$NR$^6$R$^6$, and oo) R$^6$;

R$^6$, at each occurrence, independently is selected from the group consisting of:
  a) H, b) —OR$^8$, c) an amine protecting group, d) C$_{1-6}$ alkyl, e) C$_{2-6}$ alkenyl, f) C$_{2-6}$ alkynyl, g) C$_{3-14}$ saturated, unsaturated, or aromatic carbocycle, h) 3-14 membered saturated, unsaturated, or aromatic heterocycle comprising one or more heteroatoms selected from the group consisting of nitrogen, oxygen, and sulfur, i) —C(O)—C$_{1-6}$ alkyl, j) —C(O)—C$_{2-6}$ alkenyl, k) —C(O)—C$_{2-6}$ alkynyl, l) —C(O)—C$_{3-14}$ saturated, unsaturated, or aromatic carbocycle, m) —C(O)-3-14 membered saturated, unsaturated, or aromatic heterocycle comprising one or more heteroatoms selected from the group consisting of nitrogen, oxygen, and sulfur, n) —C(O)O—C$_{1-6}$ alkyl, o) —C(O)O—C$_{2-6}$ alkenyl, p) —C(O)O—C$_{2-6}$ alkynyl, q) —C(O)O—C$_{3-14}$ saturated, unsaturated, or aromatic carbocycle, and r) —C(O)O-3-14 membered saturated, unsaturated, or aromatic heterocycle comprising one or more heteroatoms selected from the group consisting of nitrogen, oxygen, and sulfur,
    wherein any of d)-r) optionally is substituted with one or more R$^7$ groups;

R$^7$, at each occurrence, independently is selected from the group consisting of:
  a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —C(NR$^8$)R$^8$, ff) —C(NR$^8$)OR$^8$, gg) —OC(NR$^8$)R$^8$, hh) —C(NR$^8$)NR$^8$R$^8$, ii) —NR$^8$C(NR$^8$)R$^8$, jj) —OC(NR$^8$)NR$^8$R$^8$, kk) —NR$^8$C(NR$^8$)OR$^8$, ll) —NR$^8$C(NR$^8$)NR$^8$R$^8$, mm) —S(O)$_p$R$^8$, nn) —SO$_2$NR$^8$R$^8$, oo) C$_{1-6}$ alkyl, pp) C$_{2-6}$ alkenyl, qq) C$_{2-6}$ alkynyl, rr) C$_{3-14}$ saturated, unsaturated, or aromatic carbocycle, and ss) 3-14 membered saturated, unsaturated, or aromatic heterocycle comprising one or more heteroatoms selected from the group consisting of nitrogen, oxygen, and sulfur,
    wherein any of oo)-ss) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S)NR$^8$R$^8$, —C(NR$^8$)R$^8$, —C(NR$^8$)OR$^8$, —OC(NR$^8$)R$^8$, —C(NR$^8$)NR$^8$R$^8$, —NR$^8$C(NR$^8$)R$^8$, —OC(NR$^8$)NR$^8$R$^8$, —NR$^8$C(NR$^8$)OR$^8$, —NR$^8$C(NR$^8$)NR$^8$R$^8$, —SO$_2$NR$^8$R$^8$, and —S(O)$_p$R$^8$;

R$^8$, at each occurrence, independently is selected from the group consisting of:
  a) H, b) an amine protecting group, c) C$_{1-6}$ alkyl, d) C$_{2-6}$ alkenyl, e) C$_{2-6}$ alkynyl, f) C$_{3-14}$ saturated, unsaturated, or aromatic carbocycle, g) 3-14 membered saturated, unsaturated, or aromatic heterocycle comprising one or more heteroatoms selected from the group consisting of nitrogen, oxygen, and sulfur, h) —C(O)—C$_{1-6}$ alkyl, i) —C(O)—C$_{2-6}$ alkenyl, j) —C(O)—C$_{2-6}$ alkynyl, k) —C(O)—C$_{3-14}$ saturated, unsaturated, or aromatic carbocycle, l) —C(O)-3-14 membered saturated, unsaturated, or aromatic heterocycle comprising one or more heteroatoms selected from the group consisting of nitrogen, oxygen, and sulfur, m) —C(O)O—C$_{1-6}$ alkyl, n) —C(O)O—C$_{2-6}$ alkenyl, o) —C(O)O—$C_{2-6}$ alkynyl, p) —C(O)O—$C_{3-14}$ saturated, unsaturated, or aromatic carbocycle, and q) —C(O)O-3-14 membered saturated, unsaturated, or aromatic heterocycle comprising one or more heteroatoms selected from the group consisting of nitrogen, oxygen, and sulfur, wherein any of c)-q) optionally is substituted with one or more moieties selected from the group consisting of F, Cl, Br, I, —$CF_3$, —OH, —$OC_{1-6}$ alkyl, —SH, —$SC_{1-6}$ alkyl, —CN, —$NO_2$, —$NH_2$, —$NHC_{1-6}$ alkyl, —$N(C_{1-6}$ alkyl$)_2$, —$C(O)C_{1-6}$ alkyl, —$C(O)OC_{1-6}$ alkyl, —$C(O)NH_2$, —$C(O)NHC_{1-6}$ alkyl, —$C(O)N(C_{1-6}$ alkyl$)_2$, —NHC(O)$C_{1-6}$ alkyl, —$SO_2NH_2$—, —$SO_2NHC_{1-6}$ alkyl, —$SO_2N(C_{1-6}$ alkyl$)_2$, and —$S(O)_pC_{1-6}$ alkyl;

$R^9$ is selected from the group consisting of:
a) $C_{1-6}$ alkyl, b) phenyl, and c) toluoyl;
wherein any of a)-c) optionally is substituted with one or more moieties selected from the group consisting of F, Cl, Br, and I;

m is 0, 1, 2, 3, or 4;
n is 0, 1, 2, 3, or 4; and
p, at each occurrence, independently is 0, 1, or 2.

* * * * *